(12) United States Patent
Degnan et al.

(10) Patent No.: US 11,548,870 B2
(45) Date of Patent: Jan. 10, 2023

(54) COMPOUNDS USEFUL AS INHIBITORS OF HELIOS PROTEIN

(71) Applicant: Bristol-Myers Squibb Company, Princeton, NJ (US)

(72) Inventors: Andrew P. Degnan, Jamison, PA (US); Godwin Kwame Kumi, Morrisville, PA (US); Audris Huang, New Hope, PA (US); James Aaron Balog, Lambertville, NJ (US); Ashok Vinayak Purandare, Pennington, NJ (US); Weifang Shan, Princeton, NJ (US); Guo Li, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 120 days.

(21) Appl. No.: 16/950,978

(22) Filed: Nov. 18, 2020

(65) Prior Publication Data
US 2021/0147383 A1 May 20, 2021

Related U.S. Application Data

(60) Provisional application No. 62/937,350, filed on Nov. 19, 2019.

(51) Int. Cl.
| | | |
|---|---|---|
| *C07D 407/14* | (2006.01) | |
| *C07D 401/14* | (2006.01) | |
| *C07D 413/14* | (2006.01) | |
| *C07D 417/14* | (2006.01) | |
| *C07D 487/04* | (2006.01) | |
| *C07D 491/107* | (2006.01) | |
| *A61K 31/4439* | (2006.01) | |
| *A61P 35/00* | (2006.01) | |
| *C07D 405/14* | (2006.01) | |
| *C07D 498/18* | (2006.01) | |

(52) U.S. Cl.
CPC ......... *C07D 401/14* (2013.01); *C07D 405/14* (2013.01); *C07D 417/14* (2013.01); *C07D 487/04* (2013.01); *C07D 498/18* (2013.01)

(58) Field of Classification Search
CPC .. C07D 407/14; C07D 401/14; C07D 413/14; C07D 417/14; C07D 487/04; C07D 491/107; A61K 31/4439; A61P 35/00
See application file for complete search history.

(56) References Cited

U.S. PATENT DOCUMENTS

| 9,523,126 | B2 | 12/2016 | Drake et al. |
| 10,040,804 | B2 | 8/2018 | Chan et al. |
| 10,669,260 | B2 | 6/2020 | Chan et al. |
| 2018/0015087 | A1 | 1/2018 | Liu et al. |
| 2018/0099940 | A1 | 4/2018 | Crew et al. |

(Continued)

FOREIGN PATENT DOCUMENTS

| JP | 2011012014 A2 | 1/2011 |
| WO | 199803502 A1 | 1/1998 |

(Continued)

OTHER PUBLICATIONS

International Search Report PCTUS2020060937, 29012021, ISA/EP, WO.

(Continued)

*Primary Examiner* — Bruck Kifle
(74) *Attorney, Agent, or Firm* — Gary Greenblatt

(57) ABSTRACT

Disclosed are compounds of Formula (I):

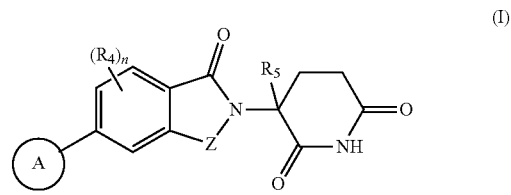

or a salt thereof, wherein: Z is $CR_6R_6$ or $C=O$; Ring A is:

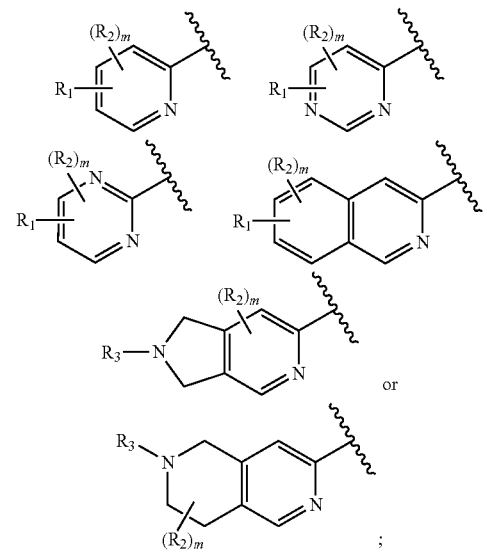

and $R_1$, $R_2$, $R_3$, $R_4$, $R_5$, m, and n are defined herein. Also disclosed are methods of using such compounds to inhibit Helios protein, and pharmaceutical compositions comprising such compounds. These compounds are useful in the treatment of viral infections and proliferative disorders, such as cancer.

12 Claims, No Drawings
Specification includes a Sequence Listing.

(56) References Cited

U.S. PATENT DOCUMENTS

| | | |
|---|---|---|
| 2018/0125821 A1 | 5/2018 | Crew et al. |
| 2019/0017998 A1 | 1/2019 | Cathers et al. |
| 2020/0016143 A1 | 1/2020 | Beckwith et al. |
| 2020/0017461 A1 | 1/2020 | Adcock et al. |
| 2020/0148663 A1 | 5/2020 | Chan et al. |

FOREIGN PATENT DOCUMENTS

| | | |
|---|---|---|
| WO | 2002059106 A1 | 8/2002 |
| WO | 2003014315 A2 | 2/2003 |
| WO | 2015107196 A1 | 7/2015 |
| WO | 2016197032 A1 | 12/2016 |
| WO | 2017046036 A1 | 3/2017 |
| WO | 2017161119 A1 | 9/2017 |
| WO | 2017176957 A1 | 10/2017 |
| WO | 2017185034 A1 | 10/2017 |
| WO | 2017197051 A1 | 11/2017 |
| WO | 2017197055 A1 | 11/2017 |
| WO | 2017197056 A1 | 11/2017 |
| WO | 2018052945 A1 | 3/2018 |
| WO | 2018102725 A1 | 6/2018 |
| WO | 2018118598 A1 | 6/2018 |
| WO | 2018119441 A9 | 6/2018 |
| WO | 2018119448 A1 | 6/2018 |
| WO | 2019038717 A1 | 2/2019 |
| WO | 2019079569 A1 | 4/2019 |
| WO | 2019148055 A9 | 8/2019 |
| WO | 2019191112 A1 | 10/2019 |
| WO | 2019241271 A1 | 12/2019 |
| WO | 2020128972 A1 | 6/2020 |
| WO | 2021087093 A1 | 5/2021 |

OTHER PUBLICATIONS

Kronke et al., "Lenalidomide Causes Selective Degradaton of IKZF1 and IKZF3 in Multiple Myeloma Cells", Science 343 301-305 (2014).

Lu et al., "The Myeloma Drug Lenalidomide Promotes Cereblon-Dependent Destruction of Ikaros Proteins", Science 343 305-309 (2014).

Petzold et al., Structural basis of lenalidomide-induced CK1α degradation by the CRL4CRBN ubiquitin ligase, Nature 532, 127-130 (2016).

Stewart et al., "New thalidomide analogues derived through Sonogashira or Suzuki reactions and their TNF expression inhibition profiles" Bioorganic & Medicinal Chemistry, 18(2) 650-662 (2010).

Stewart et al., "Synthesis and TNF expression inhibitory properties of new thalidomide analogues derived via Heck cross coupling" Bioorganic & Medicinal Chemistry Letters, 17 5819-5824 (2007).

Thornton et al., "CD4+CD25+ Immunoregulatory T Cells Suppress Polyclonal T Cell Activation In Vitro by Inhibiting Interleukin 2 Production" J Experimental Medicine 188(2) 287-296 (1998).

Yu et al., "Intratumor depletion of CD4+ cells unmasks tumor immunogenicity leading to the rejection of late-stage tumors" J. Experimental Medicine 201(5) 779-791 (2005).

SEQUENCE LISTING

<160> NUMBER OF SEQ ID NOS: 8

<210> SEQ ID NO 1
<211> LENGTH: 526
<212> TYPE: PRT
<213> ORGANISM: Homo sapiens

<400> SEQUENCE: 1

```
Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Lys Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Lys Leu
            100                 105                 110

Lys Cys Asp Val Cys Gly Met Val Cys Ile Gly Pro Asn Val Leu Met
        115                 120                 125

Val His Lys Arg Ser His Thr Gly Glu Arg Pro Phe His Cys Asn Gln
130                 135                 140

Cys Gly Ala Ser Phe Thr Gln Lys Gly Asn Leu Leu Arg His Ile Lys
145                 150                 155                 160

Leu His Ser Gly Glu Lys Pro Phe Lys Cys Pro Phe Cys Ser Tyr Ala
                165                 170                 175

Cys Arg Arg Arg Asp Ala Leu Thr Gly His Leu Arg Thr His Ser Val
            180                 185                 190

Gly Lys Pro His Lys Cys Asn Tyr Cys Gly Arg Ser Tyr Lys Gln Arg
        195                 200                 205

Ser Ser Leu Glu Glu His Lys Glu Arg Cys His Asn Tyr Leu Gln Asn
    210                 215                 220

Val Ser Met Glu Ala Ala Gly Gln Val Met Ser His His Val Pro Pro
225                 230                 235                 240

Met Glu Asp Cys Lys Glu Gln Glu Pro Ile Met Asp Asn Asn Ile Ser
```

```
                    245                 250                 255
Leu Val Pro Phe Glu Arg Pro Ala Val Ile Glu Lys Leu Thr Gly Asn
                260                 265                 270

Met Gly Lys Arg Lys Ser Ser Thr Pro Gln Lys Phe Val Gly Glu Lys
            275                 280                 285

Leu Met Arg Phe Ser Tyr Pro Asp Ile His Phe Asp Met Asn Leu Thr
290                 295                 300

Tyr Glu Lys Glu Ala Glu Leu Met Gln Ser His Met Met Asp Gln Ala
305                 310                 315                 320

Ile Asn Asn Ala Ile Thr Tyr Leu Gly Ala Glu Ala Leu His Pro Leu
                325                 330                 335

Met Gln His Pro Pro Ser Thr Ile Ala Glu Val Ala Pro Val Ile Ser
            340                 345                 350

Ser Ala Tyr Ser Gln Val Tyr His Pro Asn Arg Ile Glu Arg Pro Ile
        355                 360                 365

Ser Arg Glu Thr Ala Asp Ser His Glu Asn Asn Met Asp Gly Pro Ile
    370                 375                 380

Ser Leu Ile Arg Pro Lys Ser Arg Pro Gln Glu Arg Glu Ala Ser Pro
385                 390                 395                 400

Ser Asn Ser Cys Leu Asp Ser Thr Asp Ser Glu Ser Ser His Asp Asp
                405                 410                 415

His Gln Ser Tyr Gln Gly His Pro Ala Leu Asn Pro Lys Arg Lys Gln
            420                 425                 430

Ser Pro Ala Tyr Met Lys Glu Asp Val Lys Ala Leu Asp Thr Thr Lys
        435                 440                 445

Ala Pro Lys Gly Ser Leu Lys Asp Ile Tyr Lys Val Phe Asn Gly Glu
    450                 455                 460

Gly Glu Gln Ile Arg Ala Phe Lys Cys Glu His Cys Arg Val Leu Phe
465                 470                 475                 480

Leu Asp His Val Met Tyr Thr Ile His Met Gly Cys His Gly Tyr Arg
                485                 490                 495

Asp Pro Leu Glu Cys Asn Ile Cys Gly Tyr Arg Ser Gln Asp Arg Tyr
            500                 505                 510

Glu Phe Ser Ser His Ile Val Arg Gly Glu His Thr Phe His
        515                 520                 525

<210> SEQ ID NO 2
<211> LENGTH: 500
<212> TYPE: PRT
<213> ORGANISM: Homo sapiens

<400> SEQUENCE: 2

Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Lys Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95
```

```
Gln Glu Leu Gln Gly Glu Gly Gly Ile Arg Leu Pro Asn Gly Glu Arg
                100                 105                 110

Pro Phe His Cys Asn Gln Cys Gly Ala Ser Phe Thr Gln Lys Gly Asn
            115                 120                 125

Leu Leu Arg His Ile Lys Leu His Ser Gly Glu Lys Pro Phe Lys Cys
        130                 135                 140

Pro Phe Cys Ser Tyr Ala Cys Arg Arg Arg Asp Ala Leu Thr Gly His
145                 150                 155                 160

Leu Arg Thr His Ser Val Gly Lys Pro His Lys Cys Asn Tyr Cys Gly
                165                 170                 175

Arg Ser Tyr Lys Gln Arg Ser Ser Leu Glu Glu His Lys Glu Arg Cys
            180                 185                 190

His Asn Tyr Leu Gln Asn Val Ser Met Glu Ala Ala Gly Gln Val Met
        195                 200                 205

Ser His His Val Pro Pro Met Glu Asp Cys Lys Glu Gln Glu Pro Ile
210                 215                 220

Met Asp Asn Asn Ile Ser Leu Val Pro Phe Glu Arg Pro Ala Val Ile
225                 230                 235                 240

Glu Lys Leu Thr Gly Asn Met Gly Lys Arg Lys Ser Ser Thr Pro Gln
                245                 250                 255

Lys Phe Val Gly Glu Lys Leu Met Arg Phe Ser Tyr Pro Asp Ile His
            260                 265                 270

Phe Asp Met Asn Leu Thr Tyr Glu Lys Glu Ala Glu Leu Met Gln Ser
        275                 280                 285

His Met Met Asp Gln Ala Ile Asn Asn Ala Ile Thr Tyr Leu Gly Ala
290                 295                 300

Glu Ala Leu His Pro Leu Met Gln His Pro Pro Ser Thr Ile Ala Glu
305                 310                 315                 320

Val Ala Pro Val Ile Ser Ser Ala Tyr Ser Gln Val Tyr His Pro Asn
                325                 330                 335

Arg Ile Glu Arg Pro Ile Ser Arg Glu Thr Ala Asp Ser His Glu Asn
            340                 345                 350

Asn Met Asp Gly Pro Ile Ser Leu Ile Arg Pro Lys Ser Arg Pro Gln
        355                 360                 365

Glu Arg Glu Ala Ser Pro Ser Asn Ser Cys Leu Asp Ser Thr Asp Ser
370                 375                 380

Glu Ser Ser His Asp Asp His Gln Ser Tyr Gln Gly His Pro Ala Leu
385                 390                 395                 400

Asn Pro Lys Arg Lys Gln Ser Pro Ala Tyr Met Lys Glu Asp Val Lys
                405                 410                 415

Ala Leu Asp Thr Thr Lys Ala Pro Lys Gly Ser Leu Lys Asp Ile Tyr
            420                 425                 430

Lys Val Phe Asn Gly Glu Gly Glu Gln Ile Arg Ala Phe Lys Cys Glu
        435                 440                 445

His Cys Arg Val Leu Phe Leu Asp His Val Met Tyr Thr Ile His Met
450                 455                 460

Gly Cys His Gly Tyr Arg Asp Pro Leu Glu Cys Asn Ile Cys Gly Tyr
465                 470                 475                 480

Arg Ser Gln Asp Arg Tyr Glu Phe Ser Ser His Ile Val Arg Gly Glu
                485                 490                 495

His Thr Phe His
            500
```

```
<210> SEQ ID NO 3
<211> LENGTH: 452
<212> TYPE: PRT
<213> ORGANISM: Homo sapiens

<400> SEQUENCE: 3

Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Lys Pro
50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Glu Arg
            100                 105                 110

Pro Phe His Cys Asn Gln Cys Gly Ala Ser Phe Thr Gln Lys Gly Asn
        115                 120                 125

Leu Leu Arg His Ile Lys Leu His Ser Gly Glu Lys Pro Phe Lys Cys
130                 135                 140

Pro Phe Cys Ser Tyr Ala Cys Arg Arg Arg Asp Ala Leu Thr Gly His
145                 150                 155                 160

Leu Arg Thr His Ser Val Gly Lys Pro His Lys Cys Asn Tyr Cys Gly
                165                 170                 175

Arg Ser Tyr Lys Gln Arg Ser Ser Leu Glu Glu His Lys Glu Arg Cys
            180                 185                 190

His Asn Tyr Leu Gln Asn Val Ser Met Glu Ala Ala Gly Gln Val Met
        195                 200                 205

Ser His His Gly Glu Lys Leu Met Arg Phe Ser Tyr Pro Asp Ile His
210                 215                 220

Phe Asp Met Asn Leu Thr Tyr Glu Lys Glu Ala Glu Leu Met Gln Ser
225                 230                 235                 240

His Met Met Asp Gln Ala Ile Asn Asn Ala Ile Thr Tyr Leu Gly Ala
                245                 250                 255

Glu Ala Leu His Pro Leu Met Gln His Pro Ser Thr Ile Ala Glu
            260                 265                 270

Val Ala Pro Val Ile Ser Ser Ala Tyr Ser Gln Val Tyr His Pro Asn
        275                 280                 285

Arg Ile Glu Arg Pro Ile Ser Arg Glu Thr Ala Asp Ser His Glu Asn
290                 295                 300

Asn Met Asp Gly Pro Ile Ser Leu Ile Arg Pro Lys Ser Arg Pro Gln
305                 310                 315                 320

Glu Arg Glu Ala Ser Pro Ser Asn Ser Cys Leu Asp Ser Thr Asp Ser
                325                 330                 335

Glu Ser Ser His Asp Asp His Gln Ser Tyr Gln Gly His Pro Ala Leu
            340                 345                 350

Asn Pro Lys Arg Lys Gln Ser Pro Ala Tyr Met Lys Glu Asp Val Lys
        355                 360                 365

Ala Leu Asp Thr Thr Lys Ala Pro Lys Gly Ser Leu Lys Asp Ile Tyr
370                 375                 380
```

```
Lys Val Phe Asn Gly Glu Gly Glu Gln Ile Arg Ala Phe Lys Cys Glu
385                 390                 395                 400

His Cys Arg Val Leu Phe Leu Asp His Val Met Tyr Thr Ile His Met
            405                 410                 415

Gly Cys His Gly Tyr Arg Asp Pro Leu Glu Cys Asn Ile Cys Gly Tyr
        420                 425                 430

Arg Ser Gln Asp Arg Tyr Glu Phe Ser Ser His Ile Val Arg Gly Glu
        435                 440                 445

His Thr Phe His
        450

<210> SEQ ID NO 4
<211> LENGTH: 239
<212> TYPE: PRT
<213> ORGANISM: Homo sapiens

<400> SEQUENCE: 4

Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Cys Asp Arg Lys Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Lys Leu
            100                 105                 110

Lys Cys Asp Val Cys Gly Met Val Cys Ile Gly Pro Asn Val Leu Met
        115                 120                 125

Val His Lys Arg Ser His Thr Gly Glu Arg Pro Phe His Cys Asn Gln
130                 135                 140

Cys Gly Ala Ser Phe Thr Gln Lys Gly Asn Leu Leu Arg His Ile Lys
145                 150                 155                 160

Leu His Ser Gly Glu Lys Pro Phe Lys Cys Pro Phe Cys Ser Tyr Ala
                165                 170                 175

Cys Arg Arg Arg Asp Ala Leu Thr Gly His Leu Arg Thr His Ser Val
            180                 185                 190

Gly Lys Pro His Lys Cys Asn Tyr Cys Gly Arg Ser Tyr Lys Gln Arg
        195                 200                 205

Ser Ser Leu Glu Glu His Lys Glu Arg Cys His Asn Tyr Leu Gln Asn
    210                 215                 220

Val Ser Met Glu Ala Ala Gly Gln Val Met Ser His His Asp Ser
225                 230                 235

<210> SEQ ID NO 5
<211> LENGTH: 454
<212> TYPE: PRT
<213> ORGANISM: Homo sapiens

<400> SEQUENCE: 5

Met Glu Thr Glu Ala Ile Asp Gly Tyr Ile Thr Cys Asp Asn Glu Leu
1               5                   10                  15
```

```
Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
            35                  40                  45

Ser Val Lys Leu Glu Met Gln Ser Asp Glu Cys Asp Arg Lys Pro
 50                  55                  60

Leu Ser Arg Glu Asp Glu Ile Arg Gly His Asp Gly Ser Ser Leu
65                  70                  75                  80

Glu Glu Pro Leu Ile Glu Ser Ser Glu Val Ala Asp Asn Arg Lys Val
            85                  90                  95

Gln Glu Leu Gln Gly Glu Gly Gly Ile Arg Leu Pro Asn Gly Glu Arg
            100                 105                 110

Pro Phe His Cys Asn Gln Cys Gly Ala Ser Phe Thr Gln Lys Gly Asn
            115                 120                 125

Leu Leu Arg His Ile Lys Leu His Ser Gly Glu Lys Pro Phe Lys Cys
            130                 135                 140

Pro Phe Cys Ser Tyr Ala Cys Arg Arg Arg Asp Ala Leu Thr Gly His
145                 150                 155                 160

Leu Arg Thr His Ser Val Pro Pro Met Glu Asp Cys Lys Glu Gln Glu
                165                 170                 175

Pro Ile Met Asp Asn Asn Ile Ser Leu Val Pro Phe Glu Arg Pro Ala
                180                 185                 190

Val Ile Glu Lys Leu Thr Gly Asn Met Gly Lys Arg Lys Ser Ser Thr
            195                 200                 205

Pro Gln Lys Phe Val Gly Glu Lys Leu Met Arg Phe Ser Tyr Pro Asp
            210                 215                 220

Ile His Phe Asp Met Asn Leu Thr Tyr Glu Lys Glu Ala Glu Leu Met
225                 230                 235                 240

Gln Ser His Met Met Asp Gln Ala Ile Asn Asn Ala Ile Thr Tyr Leu
                245                 250                 255

Gly Ala Glu Ala Leu His Pro Leu Met Gln His Pro Pro Ser Thr Ile
            260                 265                 270

Ala Glu Val Ala Pro Val Ile Ser Ser Ala Tyr Ser Gln Val Tyr His
            275                 280                 285

Pro Asn Arg Ile Glu Arg Pro Ile Ser Arg Glu Thr Ala Asp Ser His
            290                 295                 300

Glu Asn Asn Met Asp Gly Pro Ile Ser Leu Ile Arg Pro Lys Ser Arg
305                 310                 315                 320

Pro Gln Glu Arg Glu Ala Ser Pro Ser Asn Ser Cys Leu Asp Ser Thr
            325                 330                 335

Asp Ser Glu Ser Ser His Asp Asp His Gln Ser Tyr Gln Gly His Pro
            340                 345                 350

Ala Leu Asn Pro Lys Arg Lys Gln Ser Pro Ala Tyr Met Lys Glu Asp
            355                 360                 365

Val Lys Ala Leu Asp Thr Thr Lys Ala Pro Lys Gly Ser Leu Lys Asp
            370                 375                 380

Ile Tyr Lys Val Phe Asn Gly Glu Gly Glu Gln Ile Arg Ala Phe Lys
385                 390                 395                 400

Cys Glu His Cys Arg Val Leu Phe Leu Asp His Val Met Tyr Thr Ile
                405                 410                 415

His Met Gly Cys His Gly Tyr Arg Asp Pro Leu Glu Cys Asn Ile Cys
            420                 425                 430

Gly Tyr Arg Ser Gln Asp Arg Tyr Glu Phe Ser Ser His Ile Val Arg
```

-continued

```
                435                 440                 445
Gly Glu His Thr Phe His
    450

<210> SEQ ID NO 6
<211> LENGTH: 23
<212> TYPE: PRT
<213> ORGANISM: Homo sapiens

<400> SEQUENCE: 6

Phe His Cys Asn Gln Cys Gly Ala Ser Phe Thr Gln Lys Gly Asn Leu
1               5                   10                  15

Leu Arg His Ile Lys Leu His
            20

<210> SEQ ID NO 7
<211> LENGTH: 585
<212> TYPE: PRT
<213> ORGANISM: Homo sapiens

<400> SEQUENCE: 7

Met His Thr Pro Pro Ala Leu Pro Arg Phe Gln Gly Gly Gly Arg
1               5                   10                  15

Val Arg Thr Pro Gly Ser His Arg Gln Gly Lys Asp Asn Leu Glu Arg
            20                  25                  30

Asp Pro Ser Gly Gly Cys Val Pro Asp Phe Leu Pro Gln Ala Gln Asp
        35                  40                  45

Ser Asn His Phe Ile Met Glu Ser Leu Phe Cys Glu Ser Ser Gly Asp
    50                  55                  60

Ser Ser Leu Glu Lys Glu Phe Leu Gly Ala Pro Val Gly Pro Ser Val
65                  70                  75                  80

Ser Thr Pro Asn Ser Gln His Ser Ser Pro Ser Arg Ser Leu Ser Ala
                85                  90                  95

Asn Ser Ile Lys Val Glu Met Tyr Ser Asp Glu Glu Ser Ser Arg Leu
            100                 105                 110

Leu Gly Pro Asp Glu Arg Leu Leu Glu Lys Asp Asp Ser Val Ile Val
        115                 120                 125

Glu Asp Ser Leu Ser Glu Pro Leu Gly Tyr Cys Asp Gly Ser Gly Pro
    130                 135                 140

Glu Pro His Ser Pro Gly Gly Ile Arg Leu Pro Asn Gly Lys Leu Lys
145                 150                 155                 160

Cys Asp Val Cys Gly Met Val Cys Ile Gly Pro Asn Val Leu Met Val
                165                 170                 175

His Lys Arg Ser His Thr Gly Glu Arg Pro Phe His Cys Asn Gln Cys
            180                 185                 190

Gly Ala Ser Phe Thr Gln Lys Gly Asn Leu Leu Arg His Ile Lys Leu
        195                 200                 205

His Ser Gly Glu Lys Pro Phe Lys Cys Pro Phe Cys Asn Tyr Ala Cys
    210                 215                 220

Arg Arg Arg Asp Ala Leu Thr Gly His Leu Arg Thr His Ser Val Ser
225                 230                 235                 240

Ser Pro Thr Val Gly Lys Pro Tyr Lys Cys Asn Tyr Cys Gly Arg Ser
                245                 250                 255

Tyr Lys Gln Gln Ser Thr Leu Glu Glu His Lys Glu Arg Cys His Asn
            260                 265                 270

Tyr Leu Gln Ser Leu Ser Thr Glu Ala Gln Ala Leu Ala Gly Gln Pro
```

```
            275                 280                 285
Gly Asp Glu Ile Arg Asp Leu Glu Met Val Pro Asp Ser Met Leu His
290                 295                 300

Ser Ser Ser Glu Arg Pro Thr Phe Ile Asp Arg Leu Ala Asn Ser Leu
305                 310                 315                 320

Thr Lys Arg Lys Arg Ser Thr Pro Gln Lys Phe Val Gly Glu Lys Gln
                325                 330                 335

Met Arg Phe Ser Leu Ser Asp Leu Pro Tyr Asp Val Asn Ser Gly Gly
            340                 345                 350

Tyr Glu Lys Asp Val Glu Leu Val Ala His His Ser Leu Glu Pro Gly
        355                 360                 365

Phe Gly Ser Ser Leu Ala Phe Val Gly Ala Glu His Leu Arg Pro Leu
    370                 375                 380

Arg Leu Pro Pro Thr Asn Cys Ile Ser Glu Leu Thr Pro Val Ile Ser
385                 390                 395                 400

Ser Val Tyr Thr Gln Met Gln Pro Leu Pro Gly Arg Leu Glu Leu Pro
                405                 410                 415

Gly Ser Arg Glu Ala Gly Glu Gly Pro Glu Asp Leu Ala Asp Gly Gly
            420                 425                 430

Pro Leu Leu Tyr Arg Pro Arg Gly Pro Leu Thr Asp Pro Gly Ala Ser
        435                 440                 445

Pro Ser Asn Gly Cys Gln Asp Ser Thr Asp Thr Glu Ser Asn His Glu
    450                 455                 460

Asp Arg Val Ala Gly Val Val Ser Leu Pro Gln Gly Pro Pro Pro Gln
465                 470                 475                 480

Pro Pro Pro Thr Ile Val Val Gly Arg His Ser Pro Ala Tyr Ala Lys
                485                 490                 495

Glu Asp Pro Lys Pro Gln Glu Gly Leu Leu Arg Gly Thr Pro Gly Pro
            500                 505                 510

Ser Lys Glu Val Leu Arg Val Val Gly Glu Ser Gly Glu Pro Val Lys
        515                 520                 525

Ala Phe Lys Cys Glu His Cys Arg Ile Leu Phe Leu Asp His Val Met
    530                 535                 540

Phe Thr Ile His Met Gly Cys His Gly Phe Arg Asp Pro Phe Glu Cys
545                 550                 555                 560

Asn Ile Cys Gly Tyr His Ser Gln Asp Arg Tyr Glu Phe Ser Ser His
                565                 570                 575

Ile Val Arg Gly Glu His Lys Val Gly
            580                 585

<210> SEQ ID NO 8
<211> LENGTH: 544
<212> TYPE: PRT
<213> ORGANISM: Homo sapiens

<400> SEQUENCE: 8

Met Asp Ser Arg Tyr Leu Gln Leu Gln Leu Tyr Leu Pro Ser Cys Ser
1               5                   10                  15

Leu Leu Gln Gly Ser Gly Asp Ser Ser Leu Glu Lys Glu Phe Leu Gly
            20                  25                  30

Ala Pro Val Gly Pro Ser Val Ser Thr Pro Asn Ser Gln His Ser Ser
        35                  40                  45

Pro Ser Arg Ser Leu Ser Ala Asn Ser Ile Lys Val Glu Met Tyr Ser
    50                  55                  60
```

```
Asp Glu Glu Ser Ser Arg Leu Leu Gly Pro Asp Glu Arg Leu Leu Glu
 65                  70                  75                  80

Lys Asp Asp Ser Val Ile Val Glu Asp Ser Leu Ser Glu Pro Leu Gly
                 85                  90                  95

Tyr Cys Asp Gly Ser Gly Pro Glu Pro His Ser Pro Gly Gly Ile Arg
            100                 105                 110

Leu Pro Asn Gly Lys Leu Lys Cys Asp Val Cys Gly Met Val Cys Ile
        115                 120                 125

Gly Pro Asn Val Leu Met Val His Lys Arg Ser His Thr Gly Glu Arg
    130                 135                 140

Pro Phe His Cys Asn Gln Cys Gly Ala Ser Phe Thr Gln Lys Gly Asn
145                 150                 155                 160

Leu Leu Arg His Ile Lys Leu His Ser Gly Glu Lys Pro Phe Lys Cys
                165                 170                 175

Pro Phe Cys Asn Tyr Ala Cys Arg Arg Arg Asp Ala Leu Thr Gly His
            180                 185                 190

Leu Arg Thr His Ser Val Ser Ser Pro Thr Val Gly Lys Pro Tyr Lys
        195                 200                 205

Cys Asn Tyr Cys Gly Arg Ser Tyr Lys Gln Gln Ser Thr Leu Glu Glu
    210                 215                 220

His Lys Glu Arg Cys His Asn Tyr Leu Gln Ser Leu Ser Thr Glu Ala
225                 230                 235                 240

Gln Ala Leu Ala Gly Gln Pro Gly Asp Glu Ile Arg Asp Leu Glu Met
                245                 250                 255

Val Pro Asp Ser Met Leu His Ser Ser Ser Glu Arg Pro Thr Phe Ile
            260                 265                 270

Asp Arg Leu Ala Asn Ser Leu Thr Lys Arg Lys Arg Ser Thr Pro Gln
        275                 280                 285

Lys Phe Val Gly Glu Lys Gln Met Arg Phe Ser Leu Ser Asp Leu Pro
    290                 295                 300

Tyr Asp Val Asn Ser Gly Gly Tyr Glu Lys Asp Val Glu Leu Val Ala
305                 310                 315                 320

His His Ser Leu Glu Pro Gly Phe Gly Ser Ser Leu Ala Phe Val Gly
                325                 330                 335

Ala Glu His Leu Arg Pro Leu Arg Leu Pro Pro Thr Asn Cys Ile Ser
            340                 345                 350

Glu Leu Thr Pro Val Ile Ser Ser Val Tyr Thr Gln Met Gln Pro Leu
        355                 360                 365

Pro Gly Arg Leu Glu Leu Pro Gly Ser Arg Glu Ala Gly Glu Gly Pro
    370                 375                 380

Glu Asp Leu Ala Asp Gly Gly Pro Leu Leu Tyr Arg Pro Arg Gly Pro
385                 390                 395                 400

Leu Thr Asp Pro Gly Ala Ser Pro Ser Asn Gly Cys Gln Asp Ser Thr
                405                 410                 415

Asp Thr Glu Ser Asn His Glu Asp Arg Val Ala Gly Val Val Ser Leu
            420                 425                 430

Pro Gln Gly Pro Pro Gln Pro Pro Thr Ile Val Val Gly Arg
        435                 440                 445

His Ser Pro Ala Tyr Ala Lys Glu Asp Pro Lys Pro Gln Glu Gly Leu
    450                 455                 460

Leu Arg Gly Thr Pro Gly Pro Ser Lys Glu Val Leu Arg Val Val Gly
465                 470                 475                 480
```

```
Glu Ser Gly Glu Pro Val Lys Ala Phe Lys Cys Glu His Cys Arg Ile
            485                 490                 495
Leu Phe Leu Asp His Val Met Phe Thr Ile His Met Gly Cys His Gly
            500                 505                 510
Phe Arg Asp Pro Phe Glu Cys Asn Ile Cys Gly Tyr His Ser Gln Asp
            515                 520                 525
Arg Tyr Glu Phe Ser Ser His Ile Val Arg Gly Glu His Lys Val Gly
            530                 535                 540
```

COMPOUNDS USEFUL AS INHIBITORS OF HELIOS PROTEIN

CROSS REFERENCE

This application claims the benefit of U.S. Provisional Application Ser. No. 62/937,350 filed Nov. 19, 2019 which is incorporated herein in its entirety.

DESCRIPTION

The present invention generally relates to compounds that inhibit Helios protein. Provided herein are compounds, compositions comprising such compounds, and methods of their use. The invention further pertains to pharmaceutical compositions comprising at least one compound according to the invention that are useful for the treatment of proliferative disorders, such as cancer, and viral infections.

BACKGROUND OF THE INVENTION

Regulatory T cells (Tregs) play an essential role in controlling self-tolerance and immune homeostasis via maintenance of inhibitory activity and anergy in the face of vigorous immune and inflammatory responses. Through the preservation of a stable, anergic and suppressive phenotype, Tregs attenuate excessive immune responses and prevent or ameliorate autoimmunity. A number of reports have documented the presence of Tregs within human tumor tissues. Studies demonstrated a clear negative correlation between the number of Tregs and T cell infiltration into the tumor and survival (Curiel et al., 2004, *Nat. Med.* 10: 942-949; Viguier et al., 2004, *J Immuno.* 1173:1444-1453; Beyer et al., 2006, *Blood* 108: 804-811; Zou et al., 2006, *Nat. Rev. Immunol.* 6: 295-307), implying a potential critical role of Tregs in preventing the development of effective anti-tumor immunity. Accumulated evidence indicates that Foxp3+CD25+CD4+Tregs dominantly infiltrate into tumors and apparently hinder immune responses to tumor cells in rodents and humans. Once activated by a specific antigen, Tregs suppress responder T cells in an antigen-nonspecific and bystander manner in vitro (Takahashi et al., 1998, *Int Immunol.* 10:1969-80; Thornton et al., 1998, *J Exp. Med.* 188:287-96). Foxp3+CD25+CD4+Tregs are apparently capable of suppressing a wide range of antitumor immune responses involving CD4+ helper T cells, CD8+ T cells, natural killer cells, and natural killer T cells (Tanaka et al., 2017, *Cell Research* 27:109-118). Intratumoral depletion of CD25+CD4+Tregs induced regression of established tumors with a change in the cytokine milieu at tumor sites (Yu et al., 2005, *J Exp Med.* 201: 779-91). In addition, transfer of Treg-depleted CD4+ T cells markedly augmented antitumor immune responses compared with Tregs containing T-cell transfer (Antony et al., 2005, *J Immunol* 174:2591-601). Tumor-infiltrating Tregs activated by either tumor-derived self-antigens or tumor-associated antigens can similarly suppress specific antitumor immune responses. Modulation of the activities of key factors to control Treg differentiation could represent a potential therapeutic strategy for the treatment of certain diseases, including cancer and viral infections.

FoxP3+CD4 Tregs are remarkably stable. Studies are still evolving to understand the genetic mechanisms that ensure their phenotypic stability after expansion during inflammation, infection or autoimmunity. Transcription factors (TF) responsible for maintaining the stable immunosuppressive phenotype of Tregs likely contribute to this process. The Helios (IKZF2) gene, a member of the Ikaros family of TFs, differs from other Ikaros family members based on its selective expression by thymocytes undergoing negative selection, as well as by regulatory lineages of CD4 and CD8 T cells. Helios is expressed by two regulatory T-cell lineages, FoxP3+CD4+ and Ly49+CD8+Tregs, which are essential to maintain self-tolerance (Kim et al., 2015, *Science* 350:334-339; Sebastian et al., 2016, *J Immunol* 196: 144-155). Interestingly, recent studies suggest that although Helios is largely dispensable for Treg activity in the steady state, control of the genetic program of FoxP3+CD4 Tregs by Helios in the context of inflammation is essential to maintain a stable phenotype and potentiate suppressive function (Thornton et al., 2010, *J Immunol.* 184:3433-3441; Kim et al., 2015). Helios expression by Tregs was demonstrated to be crucial in their capability to maintain a suppressive and anergic phenotype in the face of intense inflammatory responses. Activation of the IL-2Rα-STAT5 pathway was demonstrated to be a key contributor by ensuring Treg survival and stability (Kim et al., 2015). Helios plays an indispensable role in maintaining the phenotype of FoxP3+ CD4 Tregs by exerting dominant, lymphocyte-intrinsic inhibition to prevent autoimmune disease in the presence of highly activated self-reactive T cells from scurfy mice, which have no FoxP3 fork head domain. Bone marrow (BM) chimeras reconstituted with Helios−/−/Scurfy BM but not Helios+/+/Scurfy BM cells rapidly developed autoimmunity (Kim et al., 2015). These observations indicate the critical contribution of Helios to self-reactive T cell selection, differentiation, and function. Immune suppression exerted by Tregs can impede antitumor immune responses. A selective deficiency of Helios in FoxP3+CD4 Tregs results in increased Treg instability and conversion of intratumoral CD4 Treg to effector T cells (Teff). Instability of intratumoral Tregs may increase the numbers of Teff cells within tumors as a combined result of Treg conversion and reduced Treg suppressive activities. In addition, defective IL-2 responses were observed in Helios-deficient intratumoral Tregs, which results in decreased numbers of activated Tregs and may also contribute to the increased intratumoral Teff activities. Interaction between tumor cells and infiltrating immune cells leads to secretion of inflammatory mediators, including TNF-α, IL-6, IL-17, IL-1, and TGF-β, and the formation of a local inflammatory environment (Kim et al., 2015).

Lineage instability of Helios-deficient Tregs is also accompanied by diminished FoxP3 expression and results in the acquisition of an effector phenotype by producing proinflammatory cytokines. Effector cell conversion of Helios-deficient Tregs within the tumor-tissue microenvironment is associated with increased expression of genes that control Teff phenotype (Yates et al., 2018, *PNAS*, 2018, 115: 2162-2167). Acquisition of an unstable phenotype by Helios deficiency only occurs within the tumor microenvironment (TME), but not in peripheral lymphoid organs (Nakagawa et al., 2016, *PNAS* 113: 6248-6253). Within the chronic inflammatory TME, Helios deficiency in Tregs could drastically alleviate the repressed genetic programs associated with T helper cell differentiation by up-regulating T helper cell associated TFs and effector cytokines. These genetic changes of Helios-deficient Tregs are most apparent in a Treg subpopulation with high affinity for self-antigens, as shown by enhanced GITR/PD-1 expression and increased responsiveness to self-antigens. Their combined effects may promote a phenotype conversion of Tregs into Teff within the TME with increased T-cell receptor (TCR) engagement and costimulatory receptor expression by Tregs, suggesting that the alterations in gene expression, as a central feature of Treg conversion, are immune milieu dependent (Yates et al., 2018).

Reduced Helios expression in FoxP3+CD4 Tregs may allow conversion of memory Tregs into Teff cells that express self-reactive T-cell receptors with specificity for tumor antigens. An altered Treg signature might be selectively induced within the chronic inflammatory conditions of growing tumor. Helios-deficient Tregs may display a TCR repertoire skewed toward high-affinity against self-peptides/MHC, which can promote robust activation in TME (Yates et al., 2018). In view of the increased self-reactivity of TCR in CD4 Tregs compared with conventional T cells, conversion of Tregs could generate highly potent effector CD4 T cells accompanied by attenuated Treg-mediated suppression within the TME. A more effective strategy may depend on approaches that selectively convert intratumoral Tregs into Teff cells without affecting the systemic Treg population. As a key player in the maintenance of Treg size and functional stability in response to diverse immunological perturbations, pharmacological intervention of Helios could be relevant to the strategies that strengthen current tumor immunotherapy. Since Treg to Teff conversion may be confined to inflammatory intratumoral microenvironments, antibody or small molecule-based approaches that target Helios may lead to improved Treg dependent cancer immunotherapy. Importantly, conversion of Helios-deficient Tregs only occurs within the local inflammatory environment of the tumor. This approach may not provoke the autoimmune side effects associated with systemic reduction of Tregs. Therefore, strategies that specifically harness Helios-dependent control of the intratumoral Treg phenotype represent a significant promise to improve cancer immunotherapy. Furthermore, removal of Foxp3+Tregs was also reported to enhance vaccine-induced antitumor T-cell responses (Nishikawa et al., 2010, *Int. J. Cancer* 127: 759-767), suggesting that decreasing Helios levels could be beneficial in boosting the efficacy of cancer vaccines.

Besides anti-tumor immunotherapy, during viral infections, Treg cells can limit the immunopathology resulting from excessive inflammation, yet potentially inhibit effective antiviral T cell responses and promote virus persistence (Schmitz et al., 2013, *PLOS Pathogens* 9: e1003362). Chronic, but not acute, infection of mice with lymphocytic choriomeningitis virus results in a marked expansion of Foxp3+Tregs, implying a potential mechanism that certain infectious agents could evade host immune responses by activation and expansion of Tregs (Punkosdy et al., 2011, *PNAS* 108: 3677-3682). Treatment benefits could be achieved by decreasing Helios levels in activated Tregs in the context relevant to chronic viral infections.

There is a need for compounds useful as inhibitors of Helios protein.

SUMMARY OF THE INVENTION

The present invention provides compounds of Formula (I) or salts thereof, which are useful to decrease Helios protein levels, decrease Helios activity levels and/or inhibit Helios expression levels in the cells.

The present invention also provides pharmaceutical compositions comprising a compound of Formula (I) and/or a pharmaceutically acceptable salt thereof; and a pharmaceutically acceptable carrier.

The present invention also provides a method of treating a disease or disorder by decreasing the activity of Helios protein, the method comprising administering to a patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament to decrease Helios protein levels, decrease Helios activity levels and/or inhibit Helios expression levels in cells to control Treg differentiation, for the treatment of certain diseases, including cancer and viral infections.

The compounds of Formula (I) and compositions comprising the compounds of Formula (I) may be used in treating, preventing, or curing viral infections and various proliferative disorders, such as cancer. Pharmaceutical compositions comprising these compounds are useful in treating, preventing, or slowing the progression of diseases or disorders in a variety of therapeutic areas, such as viral infections and cancer.

These and other features of the invention will be set forth in expanded form as the disclosure continues.

DETAILED DESCRIPTION

Applicants have found compounds that inhibit Helios protein by facilitating the interaction of Helios protein and the corresponding E3 ubiquitin ligase complex (Cullin4-Cereblon, CUL4-CRBN). These compounds decrease Helios protein levels, decrease Helios activity levels and/or inhibit Helios expression levels in the cells to control Treg differentiation. These compounds are useful for the treatment of certain diseases, including cancer and viral infections. The compounds are provided to be useful as pharmaceuticals with desirable stability, bioavailability, therapeutic index, and toxicity values that are important to their drugability.

The first aspect of the present invention provides at least one compound of Formula (I):

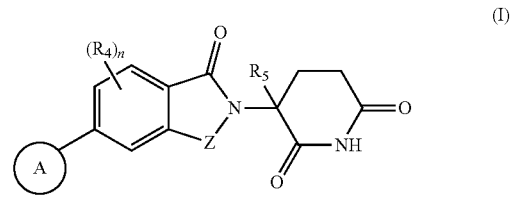

or a salt thereof, wherein:
Z is $CR_6R_6$ or C=O;
Ring A is:

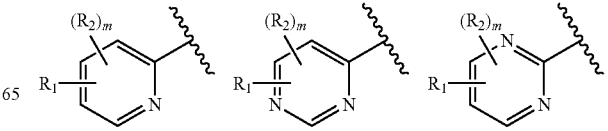

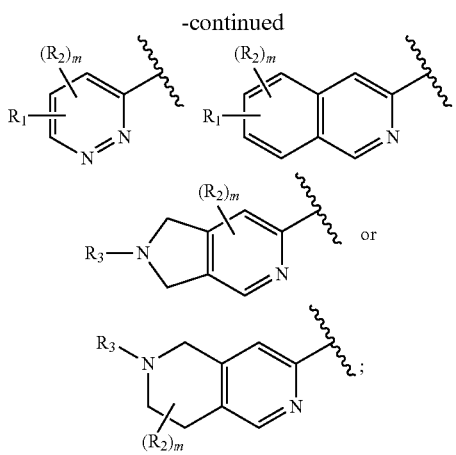

R₁ is —(CR$_z$R$_z$)$_{1-2}$NR$_{1a}$R$_{1b}$;

R$_{1a}$ is hydrogen, C$_{1-6}$ alkyl, C$_{1-4}$ fluoroalkyl, C$_{1-3}$ cyanoalkyl, C$_{1-6}$ hydroxyalkyl, —(CH$_2$)$_{1-3}$O(C$_{1-3}$ alkyl), —(CH$_2$)$_{1-3}$S(O)$_2$(C$_{1-3}$ alkyl), —(CH$_2$)$_{1-3}$C(O)O(C$_{1-3}$ alkyl), —(CH$_2$)$_{1-3}$NR$_x$R$_x$, —(CH$_2$)$_{1-3}$C(O)NR$_x$R$_x$, —(CH$_2$)$_{1-3}$NR$_x$C(O)(C$_{1-3}$ alkyl), —C(O)(C$_{1-3}$ alkyl), —CH(phenyl)(C$_{1-2}$ hydroxyalkyl), —CR$_x$R$_x$CR$_x$(phenyl)$_2$, R$_{1c}$, —(CR$_x$R$_x$)$_{1-3}$R$_{1c}$, —(CR$_x$R$_x$)$_{1-3}$OR$_{1c}$, or —C(O)R$_{1c}$;

R$_{1b}$ is hydrogen, C$_{1-3}$ alkyl, or —CH$_2$(phenyl);

or R$_{1a}$ and R$_{1b}$ along with the nitrogen atom to which they are attached, are joined together to form a cyclic group selected from azaspiro[2.5]octanyl, azepanyl, azetidinyl, azocanyl, diazepanyl, dioxidothiomorpholinyl, isoindolinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinonyl, piperidinyl, pyrrolidinyl, pyrrolidinonyl, and tetrahydroisoquinolinyl, each substituted with zero to 1 R$_{1d}$ and zero to 2 R$_{1e}$;

R$_{1c}$ is C$_{3-7}$ cycloalkyl, phenyl, oxetanyl, azetidinyl, furanyl, pyranyl, pyrrolyl, pyrrolidinyl, pyrrolidinonyl, pyrazolyl, imidazolyl, indazolyl, thiazolyl, piperidinyl, pyridinyl, tetrahydrofuranyl, tetrahydropyranyl, morpholinyl, dioxotetrahydrothiopyranyl, dioxidotetrahydrothiophenyl, benzo[d]thiazolyl, naphthalenyl, quinolinyl, or quinoxalinyl, each substituted with zero to 2 substituents independently selected from F, Cl, —CN, —OH, C$_{1-3}$ alkyl, C$_{1-3}$ fluoroalkyl, C$_{1-3}$ hydroxyalkyl, C$_{1-3}$ alkoxy, C$_{1-3}$ fluoroalkoxy, —C(O)O(C$_{1-3}$ alkyl), —NR$_y$R$_y$, —S(O)$_2$(C$_{1-3}$ alkyl), —S(O)$_2$NR$_x$R$_x$, —CH$_2$(phenyl), —NO$_2$, C$_{3-6}$ cycloalkyl, imidazolyl, and phenyl;

R$_{1d}$ is C$_{1-4}$ alkyl, C$_{1-2}$ fluoroalkyl, C$_{1-3}$ alkoxy, —NR$_y$R$_y$, —NR$_x$C(O)(C$_{1-3}$ alkyl), —C(O)(C$_{1-3}$ alkyl), —C(O)NR$_y$R$_y$, —CH$_2$(phenyl), —CH$_2$(methylpyrrolidinyl), —CH$_2$(benzo[d][1,3]dioxolyl), —CH(phenyl)$_2$, —C(O)(tetrahydrofuranyl), —C(O)(furanyl), —S(O)$_2$(methylphenyl), phenyl, methylphenyl, aminophenyl, piperidinyl, pyrazinyl, pyridinyl, pyrimidinyl, pyrrolidinyl, or dihydrobenzo[d]imidazolonyl;

R$_{1e}$ is —CH$_3$;

each R$_2$ is independently halogen, —CN, C$_{1-3}$ alkyl, C$_{1-3}$ fluoroalkyl, C$_{1-3}$ alkoxy, or C$_{1-3}$ fluoroalkoxy; NR2 (R=H, C1-3 alkyl), optionally substituted phenyl, optionally substituted heteroaryl;

R$_3$ is R$_{1a}$;

each R$_4$ is independently halogen, —CN, C$_{1-3}$ alkyl, C$_{1-3}$ fluoroalkyl, C$_{1-3}$ alkoxy, or C$_{1-3}$ fluoroalkoxy;

R$_5$ is hydrogen, F, or C$_{1-3}$ alkyl;

each R$_6$ is independently hydrogen or C$_{1-3}$ alkyl;

each R$_x$ is independently H or —CH$_3$;

each R$_y$ is independently H or C$_{1-4}$ alkyl;

each R$_z$ is independently H or —CH$_3$; or two R$_z$ attached to the same carbon atom, form a 3- to 6-membered carbocyclic ring or 3- to 6-membered heterocyclic ring;

m is zero, 1, or 2; and n is zero, 1, 2, or 3.

One embodiment provides a compound of Formula (I) or a salt thereof, wherein:

R$_{1a}$ is hydrogen, C$_{1-6}$ alkyl, C$_{1-3}$ fluoroalkyl, C$_{1-2}$ cyanoalkyl, C$_{1-4}$ hydroxyalkyl, —(CH$_2$)$_{1-3}$OCH$_3$, —(CH$_2$)$_{1-3}$S(O)$_2$(C$_{1-2}$ alkyl), —(CH$_2$)$_{1-2}$C(O)O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-3}$NR$_x$C(O)(C$_{1-3}$ alkyl), —C(O)(C$_{1-3}$ alkyl), —CH(phenyl)(C$_{1-2}$ hydroxyalkyl), —CR$_x$R$_x$CR$_x$(phenyl)$_2$, R$_{1c}$, —(CR$_x$R$_x$)$_{1-3}$R$_{1c}$, —(CR$_x$R$_x$)$_{1-3}$OR$_{1c}$, or —C(O)R$_{1c}$;

or R$_{1a}$ and R$_{1b}$ along with the nitrogen atom to which they are attached, are joined together to form a cyclic group selected from azaspiro[2.5]octanyl, azepanyl, azetidinyl, azocanyl, diazepanyl, dioxidothiomorpholinyl, isoindolinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinyl, pyrrolidinyl, and tetrahydroisoquinolinyl, each substituted with zero to 1 R$_{1d}$ and zero to 2 R$_{1e}$;

R$_{1c}$ is C$_{3-6}$ cycloalkyl, phenyl, oxetanyl, furanyl, pyrrolyl, pyrrolidinyl, pyrrolidinonyl, imidazolyl, indazolyl, thiazolyl, piperidinyl, pyridinyl, tetrahydrofuranyl, tetrahydropyranyl, morpholinyl, dioxotetrahydrothiopyranyl, dioxidotetrahydrothiophenyl, benzo[d]thiazolyl, naphthalenyl, quinolinyl, or quinoxalinyl, each substituted with zero to 2 substituents independently selected from F, Cl, —CN, —OH, C$_{1-2}$ alkyl, C$_{1-2}$ fluoroalkyl, C$_{1-2}$ hydroxyalkyl, C$_{1-2}$ alkoxy, C$_{1-2}$ fluoroalkoxy, —C(O)O(C$_{1-2}$ alkyl), —NR$_x$R$_y$, —S(O)$_2$(C$_{1-2}$ alkyl), —S(O)$_2$NR$_x$R$_x$, —CH$_2$(phenyl), —NO$_2$, C$_{3-6}$ cycloalkyl, imidazolyl, and phenyl;

R$_{1d}$ is C$_{1-3}$ alkyl, C$_{1-2}$ fluoroalkyl, C$_{1-3}$ alkoxy, —NR$_x$R$_y$, —NR$_x$C(O)(C$_{1-2}$ alkyl), —C(O)(C$_{1-2}$ alkyl), —C(O)NR$_y$R$_y$, —CH$_2$(phenyl), —CH$_2$(methylpyrrolidinyl), —CH$_2$(benzo[d][1,3]dioxolyl), —CH(phenyl)$_2$, —C(O)(tetrahydrofuranyl), —C(O)(furanyl), —S(O)$_2$(methylphenyl), phenyl, methylphenyl, aminophenyl, piperidinyl, pyrazinyl, pyridinyl, pyrimidinyl, pyrrolidinyl, or dihydrobenzo[d]imidazolonyl;

each R$_4$ is independently F, Cl, —CN, —CH$_3$, —CHF$_2$, —CF$_3$, —OCH$_3$, or —OCF$_3$;

R$_5$ is hydrogen, F, or —CH$_3$;

m is zero or 1; and n is zero, 1, or 2.

One embodiment provides a compound of Formula (I) or a salt thereof, having the structure:

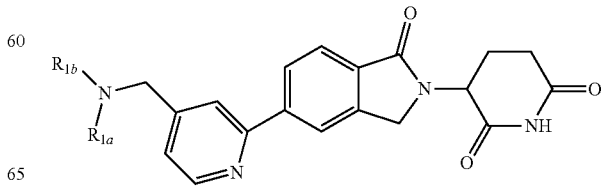

wherein:

$R_{1a}$ is hydrogen, $C_{1-6}$ alkyl, —CH₂CH₂CF₃, —CH₂CN, —CH₂CH₂OH, —CH(CH₃)CH₂OH, —CH₂CH₂CH₂CH₂OH, —CH(CH₃)CH₂CH₂OH, —CH₂CH₂OCH₃, —CH₂CH₂C(O)OCH₃, —CH₂CH₂N(CH₃)₂, —CH₂C(O)NH₂, —CH₂C(O)N(CH₃)₂, —CH₂CH₂C(O)NH₂, —CH₂CH₂NHC(O)CH₃, —CH(phenyl)(CH₂CH₂OH), —CH₂CH(phenyl)₂, $R_{1c}$, —CR$_x$R$_x$R$_{1c}$, —CH₂CH₂R$_{1c}$, —CH₂CH₂CH₂R$_{1c}$, or —CH₂CH₂OR$_{1c}$;

or $R_{1a}$ and $R_{1b}$ along with the nitrogen atom to which they are attached, are joined together to form a cyclic group selected from azaspiro[2.5]octanyl, azepanyl, azetidinyl, diazepanyl, dioxidothiomorpholinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinyl, pyrrolidinyl, and tetrahydroisoquinolinyl, each substituted with zero to 1 $R_{1d}$ and zero to 1 $R_{1e}$;

$R_{1c}$ is $C_{3-6}$ cycloalkyl, phenyl, oxetanyl, furanyl, pyrrolidinyl, pyrrolidinonyl, imidazolyl, indazolyl, thiazolyl, piperidinyl, pyridinyl, tetrahydrofuranyl, tetrahydropyranyl, morpholinyl, benzo[d]thiazolyl, naphthalenyl, quinolinyl, or quinoxalinyl, each substituted with zero to 2 substituents independently selected from F, Cl, —CN, —OH, —CH₃, —CF₃, —OCH₃, —OCF₃, —C(O)OCH₃, —NH(CH₃), —N(CH₃)₂, —S(O)₂CH₃, —S(O)₂N(CH₃)₂, —CH₂(phenyl), —NO₂, cyclopropyl, imidazolyl, and phenyl;

$R_{1d}$ is —CH₃, —CH(CH₃)₂, —OCH(CH₃)₂, —N(CH₃)₂, —NHC(O)CH₃, —C(O)CH₃, —C(O)NH₂, —C(O)N(CH₂CH₃)₂, —CH₂(phenyl), —CH₂(methylpyrrolidinyl), —CH₂(benzo[d][1,3]dioxolyl), —CH(phenyl)₂, —C(O)(tetrahydrofuranyl), —C(O)(furanyl), —S(O)₂(methylphenyl), phenyl, methylphenyl, aminophenyl, piperidinyl, pyrazinyl, pyridinyl, pyrimidinyl, pyrrolidinyl, or dihydrobenzo[d]imidazolonyl; and $R_{1e}$ is —CH₃.

One embodiment provides a compound of Formula (I) or a salt thereof, having the structure:

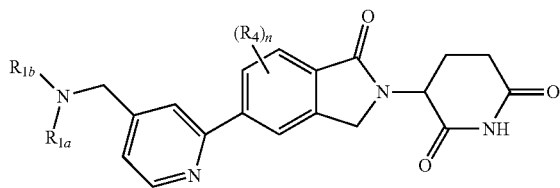

wherein:

$R_{1a}$ is hydrogen, $C_{1-6}$ alkyl, —CH₂CH₂CF₃, —CH₂CN, —CH₂CH₂OH, —CH(CH₃)CH₂OH, —CH₂CH₂CH₂CH₂OH, —CH(CH₃)CH₂CH₂OH, —CH₂CH₂OCH₃, —CH₂CH₂C(O)OCH₃, —CH₂CH₂N(CH₃)₂, —CH₂C(O)NH₂, —CH₂C(O)N(CH₃)₂, —CH₂CH₂C(O)NH₂, —CH₂CH₂NHC(O)CH₃, —CH(phenyl)(CH₂CH₂OH), —CH₂CH(phenyl)₂, $R_{1c}$, —CR$_x$R$_x$R$_{1c}$, —CH₂CH₂R$_{1c}$, —CH₂CH₂CH₂R$_{1c}$, or —CH₂CH₂OR$_{1c}$;

or $R_{1a}$ and $R_{1b}$ along with the nitrogen atom to which they are attached, are joined together to form a cyclic group selected from azaspiro[2.5]octanyl, azepanyl, azetidinyl, diazepanyl, dioxidothiomorpholinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinyl, pyrrolidinyl, and tetrahydroisoquinolinyl, each substituted with zero to 1 $R_{1d}$ and zero to 1 $R_{1e}$;

$R_{1c}$ is $C_{3-6}$ cycloalkyl, phenyl, oxetanyl, furanyl, pyrrolidinyl, pyrrolidinonyl, imidazolyl, indazolyl, thiazolyl, piperidinyl, pyridinyl, tetrahydrofuranyl, tetrahydropyranyl, morpholinyl, benzo[d]thiazolyl, naphthalenyl, quinolinyl, or quinoxalinyl, each substituted with zero to 2 substituents independently selected from F, Cl, —CN, —OH, —CH₃, —CF₃, —OCH₃, —OCF₃, —C(O)OCH₃, —NH(CH₃), —N(CH₃)₂, —S(O)₂CH₃, —S(O)₂N(CH₃)₂, —CH₂(phenyl), —NO₂, cyclopropyl, imidazolyl, and phenyl;

$R_{1d}$ is —CH₃, —CH(CH₃)₂, —OCH₃, —OCH₂CH₃, —OCH(CH₃)₂, —N(CH₃)₂, —NHC(O)CH₃, —C(O)CH₃, —C(O)NH₂, —C(O)N(CH₃)₂, —C(O)N(CH₂CH₃)₂, —CH₂(phenyl), —CH₂(methylpyrrolidinyl), —CH₂(benzo[d][1,3]dioxolyl), —CH(phenyl)₂, —C(O)(tetrahydrofuranyl), —C(O)(furanyl), —S(O)₂(methylphenyl), phenyl, methylphenyl, aminophenyl, piperidinyl, pyrazinyl, pyridinyl, pyrimidinyl, pyrrolidinyl, or dihydrobenzo[d]imidazolonyl; and $R_{1e}$ is —CH₃;

$R_4$ is —CH₃; and n is zero or 1.

One embodiment provides a compound of Formula (I) or a salt thereof, wherein Z is CR₆R₆. Compounds of this embodiment have the structure:

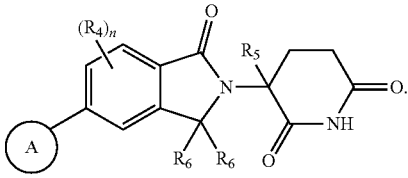

Included in this embodiment are compounds in which each $R_6$ is independently hydrogen or —CH₃. Also included in this embodiment are compounds in which each $R_6$ is hydrogen.

One embodiment provides a compound of Formula (I) or a salt thereof, wherein Z is C=O. Compounds of this embodiment have the structure:

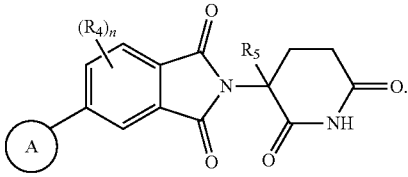

One embodiment provides a compound of Formula (I) or a salt thereof, wherein $R_{1a}$ is hydrogen, $C_{1-6}$ alkyl, $C_{1-4}$ fluoroalkyl, $C_{1-3}$ cyanoalkyl, $C_{1-6}$ hydroxyalkyl, —(CH₂)$_{1-3}$O($C_{1-3}$ alkyl), —(CH₂)$_{1-3}$S(O)₂($C_{1-3}$ alkyl), —(CH₂)$_{1-3}$C(O)O($C_{1-3}$ alkyl), —(CH₂)$_{1-3}$NR$_x$R$_x$, —(CH₂)$_{1-3}$C(O)NR$_x$R$_x$, —(CH₂)$_{1-3}$NR$_x$C(O)($C_{1-3}$ alkyl), —C(O)($C_{1-3}$ alkyl), —CH(phenyl)($C_{1-2}$ hydroxyalkyl), —CR$_x$R$_x$CR$_x$(phenyl)₂, R$_{1c}$, —(CR$_x$R$_x$)$_{1-3}$R$_{1c}$, —(CR$_x$R$_x$)$_{1-3}$OR$_{1c}$, or —C(O)R$_{1c}$; and $R_{1b}$ is hydrogen, $C_{1-3}$ alkyl, or —CH₂(phenyl).

One embodiment provides a compound of Formula (I) or a salt thereof, wherein $R_{1a}$ is hydrogen, $C_{1-6}$ alkyl, $C_{1-3}$ fluoroalkyl, $C_{1-2}$ cyanoalkyl, $C_{1-4}$ hydroxyalkyl, —$(CH_2)_{1-3}OCH_3$, —$(CH_2)_{1-3}S(O)_2(C_{1-2}$ alkyl), —$(CH_2)_{1-2}C(O)O(C_{1-3}$ alkyl), —$(CH_2)_{1-3}NR_xR_x$, —$(CH_2)_{1-2}C(O)NR_xR_x$, —$(CH_2)_{1-3}NR_xC(O)(C_{1-3}$ alkyl), —$C(O)(C_{1-3}$ alkyl), —$CH(phenyl)(C_{1-2}$ hydroxyalkyl), —$CR_xR_xCR_x(phenyl)_2$, $R_{1c}$, —$(CR_xR_x)_{1-3}R_{1c}$, —$(CR_xR_x)_{1-3}OR_{1c}$, or —$C(O)R_{1c}$; and $R_{1b}$ is hydrogen, $C_{1-3}$ alkyl, or —$CH_2(phenyl)$.

One embodiment provides a compound of Formula (I) or a salt thereof, wherein $R_{1a}$ is hydrogen, $C_{1-6}$ alkyl, —$CH_2CH_2CF_3$, —$CH_2CN$, —$CH_2CH_2OH$, —$CH(CH_3)CH_2OH$, —$CH_2CH_2CH_2CH_2OH$, —$CH(CH_3)CH_2CH_2OH$, —$CH_2CH_2OCH_3$, —$CH_2CH_2C(O)OCH_3$, —$CH_2CH_2N(CH_3)_2$, —$CH_2C(O)NH_2$, —$CH_2C(O)N(CH_3)_2$, —$CH_2CH_2C(O)NH_2$, —$CH_2CH_2NHC(O)CH_3$, —$CH(phenyl)(CH_2CH_2OH)$, —$CH_2CH(phenyl)_2$, $R_{1c}$, —$CR_xR_xR_{1c}$, —$CH_2CH_2R_{1c}$, —$CH_2CH_2CH_2R_{1c}$, or —$CH_2CH_2OR_{1c}$; and $R_{1b}$ is hydrogen, $C_{1-3}$ alkyl, or —$CH_2(phenyl)$.

One embodiment provides a compound of Formula (I) or a salt thereof, wherein $R_{1a}$ and $R_{1b}$ along with the nitrogen atom to which they are attached, are joined together to form a cyclic group selected from azaspiro[2.5]octanyl, azepanyl, azetidinyl, azocanyl, diazepanyl, dioxidothiomorpholinyl, isoindolinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinonyl, piperidinyl, pyrrolidinyl, pyrrolidinonyl, and tetrahydroisoquinolinyl, each substituted with zero to 1 $R_{1d}$ and zero to 2 $R_{1e}$. Included in this embodiment are compounds in which $R_{1d}$ is $C_{1-3}$ alkyl, $C_{1-2}$ fluoroalkyl, $C_{1-3}$ alkoxy, —$NR_xR_y$, —$NR_xC(O)(C_{1-2}$ alkyl), —$C(O)(C_{1-2}$ alkyl), —$C(O)NR_yR_y$, —$CH_2(phenyl)$, —$CH_2(methylpyrrolidinyl)$, —$CH_2(benzo[d][1,3]dioxolyl)$, —$CH(phenyl)_2$, —$C(O)(tetrahydrofuranyl)$, —$C(O)(furanyl)$, —$S(O)_2(methylphenyl)$, phenyl, methylphenyl, aminophenyl, piperidinyl, pyrazinyl, pyridinyl, pyrimidinyl, pyrrolidinyl, or dihydrobenzo[d]imidazolonyl. Also included in this embodiment are compounds in which $R_{1d}$ is —$CH_3$, —$CH(CH_3)_2$, —$OCH(CH_3)_2$, —$N(CH_3)_2$, —$NHC(O)CH_3$, —$C(O)CH_3$, —$C(O)NH_2$, —$C(O)N(CH_2CH_3)_2$, —$CH_2(phenyl)$, —$CH_2(methylpyrrolidinyl)$, —$CH_2(benzo[d][1,3]dioxolyl)$, —$CH(phenyl)_2$, —$C(O)(tetrahydrofuranyl)$, —$C(O)(furanyl)$, —$S(O)_2(methylphenyl)$, phenyl, methylphenyl, aminophenyl, piperidinyl, pyrazinyl, pyridinyl, pyrimidinyl, pyrrolidinyl, or dihydrobenzo[d]imidazolonyl.

One embodiment provides a compound of Formula (I) or a salt thereof, wherein $R_{1a}$ and $R_{1b}$ along with the nitrogen atom to which they are attached, are joined together to form a cyclic group selected from azaspiro[2.5]octanyl, azepanyl, azetidinyl, azocanyl, diazepanyl, dioxidothiomorpholinyl, isoindolinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinyl, pyrrolidinyl, and tetrahydroisoquinolinyl, each substituted with zero to 1 $R_{1d}$ and zero to 2 $R_{1e}$. Included in this embodiment are compounds in which $R_{1d}$ is $C_{1-3}$ alkyl, $C_{1-2}$ fluoroalkyl, $C_{1-3}$ alkoxy, —$NR_xR_y$, —$NR_xC(O)(C_{1-2}$ alkyl), —$C(O)(C_{1-2}$ alkyl), —$C(O)NR_yR_y$, —$CH_2(phenyl)$, —$CH_2(methylpyrrolidinyl)$, —$CH_2(benzo[d][1,3]dioxolyl)$, —$CH(phenyl)_2$, —$C(O)(tetrahydrofuranyl)$, —$C(O)(furanyl)$, —$S(O)_2(methylphenyl)$, phenyl, methylphenyl, aminophenyl, piperidinyl, pyrazinyl, pyridinyl, pyrimidinyl, pyrrolidinyl, or dihydrobenzo[d]imidazolonyl. Also included in this embodiment are compounds in which $R_{1d}$ is —$CH_3$, —$CH(CH_3)_2$, —$OCH(CH_3)_2$, —$N(CH_3)_2$, —$NHC(O)CH_3$, —$C(O)CH_3$, —$C(O)NH_2$, —$C(O)N(CH_2CH_3)_2$, —$CH_2(phenyl)$, —$CH_2(methylpyrrolidinyl)$, —$CH_2(benzo[d][1,3]dioxolyl)$, —$CH(phenyl)_2$, —$C(O)(tetrahydrofuranyl)$, —$C(O)(furanyl)$, —$S(O)_2(methylphenyl)$, phenyl, methylphenyl, aminophenyl, piperidinyl, pyrazinyl, pyridinyl, pyrimidinyl, pyrrolidinyl, or dihydrobenzo[d]imidazolonyl.

One embodiment provides a compound of Formula (I) or a salt thereof, wherein $R_{1a}$ and $R_{1b}$ along with the nitrogen atom to which they are attached, are joined together to form a cyclic group selected from azaspiro[2.5]octanyl, azepanyl, azetidinyl, diazepanyl, dioxidothiomorpholinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinyl, pyrrolidinyl, and tetrahydroisoquinolinyl, each substituted with zero to 1 $R_{1d}$ and zero to 1 $R_{1e}$. Included in this embodiment are compounds in which $R_{1d}$ is $C_{1-3}$ alkyl, $C_{1-2}$ fluoroalkyl, $C_{1-3}$ alkoxy, —$NR_xR_y$, —$NR_xC(O)(C_{1-2}$ alkyl), —$C(O)(C_{1-2}$ alkyl), —$C(O)NR_yR_y$, —$CH_2(phenyl)$, —$CH_2(methylpyrrolidinyl)$, —$CH_2(benzo[d][1,3]dioxolyl)$, —$CH(phenyl)_2$, —$C(O)(tetrahydrofuranyl)$, —$C(O)(furanyl)$, —$S(O)_2(methylphenyl)$, phenyl, methylphenyl, aminophenyl, piperidinyl, pyrazinyl, pyridinyl, pyrimidinyl, pyrrolidinyl, or dihydrobenzo[d]imidazolonyl. Also included in this embodiment are compounds in which $R_{1d}$ is —$CH_3$, —$CH(CH_3)_2$, —$OCH(CH_3)_2$, —$N(CH_3)_2$, —$NHC(O)CH_3$, —$C(O)CH_3$, —$C(O)NH_2$, —$C(O)N(CH_2CH_3)_2$, —$CH_2(phenyl)$, —$CH_2(methylpyrrolidinyl)$, —$CH_2(benzo[d][1,3]dioxolyl)$, —$CH(phenyl)_2$, —$C(O)(tetrahydrofuranyl)$, —$C(O)(furanyl)$, —$S(O)_2(methylphenyl)$, phenyl, methylphenyl, aminophenyl, piperidinyl, pyrazinyl, pyridinyl, pyrimidinyl, pyrrolidinyl, or dihydrobenzo[d]imidazolonyl.

One embodiment provides a compound of Formula (I) or a salt thereof, wherein Ring A is:

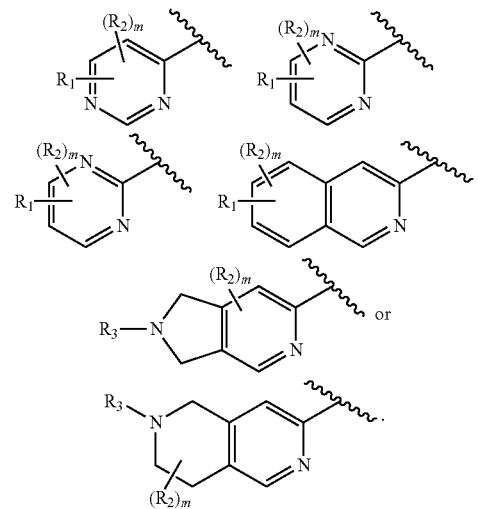

One embodiment provides a compound of Formula (I) or a salt thereof, wherein Ring A is:

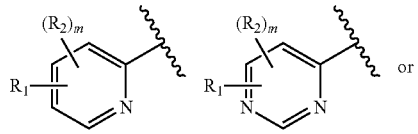

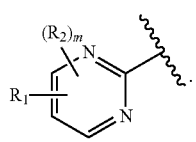

One embodiment provides a compound of Formula (I) or a salt thereof, wherein Ring A is:

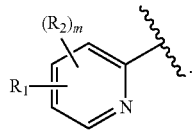

Included in this embodiment are compounds in which $R_{1a}$ is hydrogen, $C_{1-6}$ alkyl, —CH$_2$CH$_2$CF$_3$, —CH$_2$CN, —CH$_2$CH$_2$OH, —CH(CH$_3$)CH$_2$OH, —CH$_2$CH$_2$CH$_2$CH$_2$OH, —CH(CH$_3$)CH$_2$CH$_2$OH, —CH$_2$CH$_2$OCH$_3$, —CH$_2$CH$_2$C(O)OCH$_3$, —CH$_2$CH$_2$N(CH$_3$)$_2$, —CH$_2$C(O)NH$_2$, —CH$_2$C(O)N(CH$_3$)$_2$, —CH$_2$CH$_2$C(O)NH$_2$, —CH$_2$CH$_2$NHC(O)CH$_3$, —CH(phenyl)(CH$_2$CH$_2$OH), —CH$_2$CH(phenyl)$_2$, $R_{1c}$, —CR$_x$R$_x$R$_{1c}$, —CH$_2$CH$_2$R$_{1c}$, —CH$_2$CH$_2$CH$_2$R$_{1c}$, or —CH$_2$CH$_2$OR$_{1c}$; or $R_{1a}$ and $R_{1b}$ along with the nitrogen atom to which they are attached, are joined together to form a cyclic group selected from azaspiro[2.5]octanyl, azepanyl, azetidinyl, diazepanyl, dioxidothiomorpholinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinyl, pyrrolidinyl, and tetrahydroisoquinolinyl, each substituted with zero to 1 $R_{1d}$ and zero to 1 $R_{1c}$; $R_{1c}$ is $C_{3-6}$ cycloalkyl, phenyl, oxetanyl, furanyl, pyrrolidinyl, pyrrolidinonyl, imidazolyl, indazolyl, thiazolyl, piperidinyl, pyridinyl, tetrahydrofuranyl, tetrahydropyranyl, morpholinyl, benzo[d]thiazolyl, naphthalenyl, quinolinyl, or quinoxalinyl, each substituted with zero to 2 substituents independently selected from F, Cl, —CN, —OH, —CH$_3$, —CF$_3$, —OCH$_3$, —OCF$_3$, —C(O)OCH$_3$, —NH(CH$_3$), —N(CH$_3$)$_2$, —S(O)$_2$CH$_3$, —S(O)$_2$N(CH$_3$)$_2$, —CH$_2$(phenyl), —NO$_2$, cyclopropyl, imidazolyl, and phenyl; $R_{1d}$ is —CH$_3$, —CH(CH$_3$)$_2$, —OCH(CH$_3$)$_2$, —N(CH$_3$)$_2$, —NHC(O)CH$_3$, —C(O)CH$_3$, —C(O)NH$_2$, —C(O)N(CH$_2$CH$_3$)$_2$, —CH$_2$(phenyl), —CH$_2$(methylpyrrolidinyl), —CH$_2$(benzo[d][1,3]dioxolyl), —CH(phenyl)$_2$, —C(O)(tetrahydrofuranyl), —C(O)(furanyl), —S(O)$_2$(methylphenyl), phenyl, methylphenyl, aminophenyl, piperidinyl, pyrazinyl, pyridinyl, pyrimidinyl, pyrrolidinyl, or dihydrobenzo[d]imidazolonyl; and $R_{1e}$ is —CH$_3$.

One embodiment provides a compound of Formula (I) or a salt thereof, wherein Ring A is:

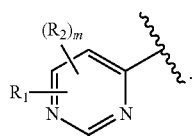

One embodiment provides a compound of Formula (I) or a salt thereof, wherein Ring A is:

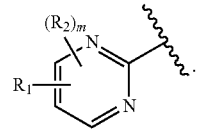

One embodiment provides a compound of Formula (I) or a salt thereof, wherein Ring A is:

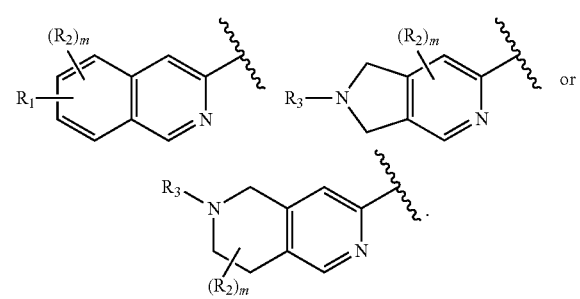

One embodiment provides a compound of Formula (I) or a salt thereof, wherein each $R_4$ is independently F, Cl, —CN, $C_{1-2}$ alkyl, $C_{1-2}$ fluoroalkyl, $C_{1-2}$ alkoxy, or $C_{1-2}$ fluoroalkoxy. Included in this embodiment are compounds in which each $R_4$ is independently F, Cl, —CN, —CH$_3$, —CF$_3$, —OCH$_3$, or —OCF$_3$. Also, included in this embodiment are compounds in which each $R_4$ is independently F, —CN, —CH$_3$, or —CF$_3$.

One embodiment provides a compound of Formula (I) or a salt thereof, wherein $R_5$ is hydrogen, deuterium, $C_{1-2}$ alkyl, or F.

One embodiment provides a compound of Formula (I) or a salt thereof, wherein $R_5$ is hydrogen, deuterium, —CH$_3$, or F.

One embodiment provides a compound of Formula (I) or a salt thereof, wherein $R_5$ is hydrogen, deuterium, or —CH$_3$.

One embodiment provides a compound of Formula (I) or a salt thereof, wherein $R_5$ is hydrogen, deuterium, or F.

One embodiment provides a compound of Formula (I) or a salt thereof, wherein $R_5$ is F.

One embodiment provides a compound of Formula (I) or a salt thereof, wherein $R_5$ is —CH$_3$.

One embodiment provides a compound of Formula (I) or a salt thereof, wherein $R_5$ is hydrogen or deuterium.

One embodiment provides a compound of Formula (I) or a salt thereof, wherein $R_5$ is deuterium.

One embodiment provides a compound of Formula (I) or a salt thereof, wherein each $R_6$ is independently hydrogen or $C_{1-2}$ alkyl. Included in this embodiment are compounds in which each $R_6$ is independently hydrogen or —CH$_3$. Also, included in this embodiment are compounds in which each $R_6$ is hydrogen.

One embodiment provides a compound of Formula (I) or a salt thereof, wherein m is zero, 1, or 2. Included in this embodiment are compounds in which m is zero or 1. Also, included in this embodiment are compounds in which m is zero.

One embodiment provides a compound of Formula (I) or a salt thereof, wherein n is zero, 1, or 2. Included in this embodiment are compounds in which n is zero or 1. Also, included in this embodiment are compounds in which n is zero.

One embodiment provides a compound of Formula (I) or a salt thereof, wherein said compound is 3-(5-{4-[(dimethylamino)methyl]pyridin-2-yl}-1-oxo-2,3-dihydro-1H-isoindol-2-yl) piperidine-2,6-dione (1); 3-(5-(4-((benzylamino)methyl)pyridin-2-yl)-1-oxoisoindolin-2-yl)piperidine-2,6-dione (2); 3-(5-(4-((methyl(propyl)amino)methyl)pyridin-2-yl)-1-oxoisoindolin-2-yl)piperidine-2,6-dione (3); 3-(5-(4-((ethyl(methyl)amino)methyl)pyridin-2-yl)-1-oxoisoindolin-2-yl)piperidine-2,6-dione (4); 3-(5-(4-((ethyl(methyl)amino)methyl)pyridin-2-yl)-1-oxoisoindolin-2-yl)piperidine-2,6-dione (5); 3-(5-(4-(((2-methoxyethyl)(methyl)amino)methyl)pyridin-2-yl)-1-oxoisoindolin-2-yl)piperidine-2,6-dione (7); 3-(5-(4-((butyl(methyl)amino)methyl)pyridin-2-yl)-1-oxoisoindolin-2-yl)piperidine-2,6-dione (9); 3-(5-(4-(((cyclopropylmethyl)(propyl)amino)methyl)pyridin-2-yl)-1-oxoisoindolin-2-yl)piperidine-2,6-dione (10); 3-(5-(4-((methyl(2-(pyridin-2-yl)ethyl)amino)methyl)pyridin-2-yl)-1-oxoisoindolin-2-yl) piperidine-2,6-dione (16); 3-(5-(4-((benzyl(isopropyl)amino)methyl)pyridin-2-yl)-1-oxoisoindolin-2-yl)piperidine-2,6-dione (19); 3-(5-(4-(((2-(dimethylamino)ethyl) (methyl)amino)methyl)pyridin-2-yl)-1-oxoisoindolin-2-yl)piperidine-2,6-dione (21); 3-(5-(4-((ethyl(pyridin-4-ylmethyl)amino)methyl)pyridin-2-yl)-1-oxoisoindolin-2-yl) piperidine-2,6-dione (22); 3-(5-(4-((methyl(1-methylpyrrolidin-3-yl)amino)methyl)pyridin-2-yl)-1-oxoisoindolin-2-yl) piperidine-2,6-dione (29); 2-(((2-(2-(2,6-dioxopiperidin-3-yl)-1-oxoisoindolin-5-yl)pyridin-4-yl)methyl)(methyl)amino)-N,N-dimethylacetamide (34); 3-(5-(4-((methyl(1-methylpyrrolidin-3-yl)amino)methyl)pyridin-2-yl)-1-oxoisoindolin-2-yl)piperidine-2,6-dione (49); 3-(5-(4-((diethylamino)methyl)pyridin-2-yl)-1-oxoisoindolin-2-yl)piperidine-2,6-dione (50); 3-(5-(4-(((cyclohexylmethyl)amino)methyl)pyridin-2-yl)-1-oxoisoindolin-2-yl)piperidine-2,6-dione (54); 3-(1-oxo-5-(4-(((1-phenylethyl)amino)methyl)pyridin-2-yl)isoindolin-2-yl) piperidine-2,6-dione (55); 3-(5-(4-(((2-methylbenzyl)amino)methyl)pyridin-2-yl)-1-oxoisoindolin-2-yl)piperidine-2,6-dione (56); 3-(5-(4-(((3-methylbenzyl)amino)methyl)pyridin-2-yl)-1-oxoisoindolin-2-yl)piperidine-2,6-dione (57); 3-(5-(4-(((4-methylbenzyl)amino)methyl)pyridin-2-yl)-1-oxoisoindolin-2-yl)piperidine-2,6-dione (58); 3-(5-(4-(((cyclohexylmethyl)(methyl)amino)methyl)pyridin-2-yl)-1-oxoisoindolin-2-yl) piperidine-2,6-dione (59); 3-(5-(4-((butylamino)methyl)pyridin-2-yl)-1-oxoisoindolin-2-yl)piperidine-2,6-dione (61); 3-(1-oxo-5-(4-((propylamino)methyl)pyridin-2-yl) isoindolin-2-yl)piperidine-2,6-dione (62); 3-(1-oxo-5-(4-((phenethylamino)methyl)pyridin-2-yl)isoindolin-2-yl)piperidine-2,6-dione (63); 3-(5-(4-(((cyclopropylmethyl)amino)methyl)pyridin-2-yl)-1-oxoisoindolin-2-yl)piperidine-2,6-dione (64); 3-(5-(4-((neopentylamino)methyl)pyridin-2-yl)-1-oxoisoindolin-2-yl)piperidine-2,6-dione (65); 3-(1-oxo-5-(4-((((tetrahydrofuran-2-yl)methyl)amino)methyl)pyridin-2-yl)isoindolin-2-yl)piperidine-2,6-dione (66); 3-(5-(4-(((4-methoxybenzyl)amino)methyl)pyridin-2-yl)-1-oxoisoindolin-2-yl)piperidine-2,6-dione (67); 3-(5-(4-(((2-methoxyethyl)amino)methyl)pyridin-2-yl)-1-oxoisoindolin-2-yl)piperidine-2,6-dione (68); 3-(5-(4-(((1-cyclopropylcyclobutyl)amino)methyl)pyridin-2-yl)-1-oxoisoindolin-2-yl)piperidine-2,6-dione (77); 3-(5-(4-(((2-methyltetrahydro-2H-pyran-4-yl)amino)methyl)pyridin-2-yl)-1-oxoisoindolin-2-yl)piperidine-2,6-dione (80); 3-(1-oxo-5-(4-((((1R,2R)-2-phenylcyclopentyl)amino)methyl)pyridin-2-yl)isoindolin-2-yl)piperidine-2,6-dione (84); 3-(5-(4-((cyclopentylamino)methyl)pyridin-2-yl)-1-oxoisoindolin-2-yl)piperidine-2,6-dione (86); 3-(5-(4-((cyclohexylamino)methyl)pyridin-2-yl)-1-oxoisoindolin-2-yl) piperidine-2,6-dione (87); 3-(5-(4-(((2-morpholinoethyl)amino)methyl)pyridin-2-yl)-1-oxoisoindolin-2-yl)piperidine-2,6-dione (88); 3-(5-(4-((tert-butylamino)methyl)pyridin-2-yl)-1-oxoisoindolin-2-yl)piperidine-2,6-dione (89); 3-(5-(4-(((2,2-diphenylethyl)amino)methyl)pyridin-2-yl)-1-oxoisoindolin-2-yl)piperidine-2,6-dione (90); N-(2-(((2-(2-(2,6-dioxopiperidin-3-yl)-1-oxoisoindolin-5-yl)pyridin-4-yl)methyl)amino)ethyl)acetamide (91); 3-(5-(4-(((2-hydroxyethyl)amino)methyl)pyridin-2-yl)-1-oxoisoindolin-2-yl) piperidine-2,6-dione (92); 3-(5-(4-(((2-chlorophenethyl)amino)methyl)pyridin-2-yl)-1-oxoisoindolin-2-yl)piperidine-2,6-dione (93); 3-(5-(4-(((4-chlorophenethyl)amino)methyl)pyridin-2-yl)-1-oxoisoindolin-2-yl)piperidine-2,6-dione (94); 3-(5-(4-(((4-methoxyphenethyl)amino)methyl)pyridin-2-yl)-1-oxoisoindolin-2-yl)piperidine-2,6-dione (95); 3-(5-(4-(((4-hydroxyphenethyl)amino)methyl)pyridin-2-yl)-1-oxoisoindolin-2-yl) piperidine-2,6-dione (96); 3-(5-(4-((isopentylamino)methyl)pyridin-2-yl)-1-oxoisoindolin-2-yl)piperidine-2,6-dione (97); 3-(1-oxo-5-(4-(((3-phenylpropyl)amino)methyl)pyridin-2-yl)isoindolin-2-yl) piperidine-2,6-dione (98); 2-(((2-(2-(2,6-dioxopiperidin-3-yl)-1-oxoisoindolin-5-yl)pyridin-4-yl)methyl)amino) acetonitrile (99); 2-(((2-(2-(2,6-dioxopiperidin-3-yl)-1-oxoisoindolin-5-yl)pyridin-4-yl)methyl)amino) acetamide (100); 3-(5-(4-(((4-hydroxycyclohexyl)amino)methyl)pyridin-2-yl)-1-oxoisoindolin-2-yl)piperidine-2,6-dione (101); 3-(5-(4-(((3-chlorophenethyl)amino)methyl)pyridin-2-yl)-1-oxoisoindolin-2-yl)piperidine-2,6-dione (102); 3-(1-oxo-5-(4-(((2-phenoxyethyl)amino)methyl)pyridin-2-yl)isoindolin-2-yl)piperidine-2,6-dione (103); 3-(5-(4-(((1-benzylpyrrolidin-3-yl)amino)methyl)pyridin-2-yl)-1-oxoisoindolin-2-yl) piperidine-2,6-dione (104); 3-(((2-(2-(2,6-dioxopiperidin-3-yl)-1-oxoisoindolin-5-yl)pyridin-4-yl) methyl)amino)propanamide (105); 3-(5-(4-(((2-(benzo[d]thiazol-2-yl)ethyl)amino)methyl)pyridin-2-yl)-1-oxoisoindolin-2-yl)piperidine-2,6-dione (106); 3-(5-(4-(((4-(dimethylamino)cyclohexyl)amino)methyl)pyridin-2-yl)-1-oxoisoindolin-2-yl) piperidine-2,6-dione (107); 3-(5-(4-((cyclobutylamino)methyl)pyridin-2-yl)-1-oxoisoindolin-2-yl)piperidine-2,6-dione (108); 3-(5-(4-((cyclopropylamino)methyl)pyridin-2-yl)-1-oxoisoindolin-2-yl)piperidine-2,6-dione (109); 3-(1-oxo-5-(4-((((2-phenylthiazol-4-yl)methyl)amino)methyl)pyridin-2-yl)isoindolin-2-yl)piperidine-2,6-dione (110); 3-(1-oxo-5-(4-(((((1R,2S)-2-phenylcyclopropyl)amino)methyl)pyridin-2-yl) isoindolin-2-yl)piperidine-2,6-dione (111); methyl 3-(((2-(2-(2,6-dioxopiperidin-3-yl)-1-oxoisoindolin-5-yl)pyridin-4-yl)methyl)amino)propanoate (112); 3-(5-(4-(((3-(1H-imidazol-1-yl)propyl)amino)methyl)pyridin-2-yl)-1-oxoisoindolin-2-yl)piperidine-2,6-dione (113); 3-(5-(4-(((3-morpholinopropyl)amino)methyl)pyridin-2-yl)-1-oxoisoindolin-2-yl)piperidine-2,6-dione (114); 3-(1-oxo-5-(4-(((3-(2-oxopyrrolidin-1-yl)propyl)amino)methyl)pyridin-2-yl)isoindolin-2-yl)piperidine-2,6-dione (115); 3-(5-(4-((ethylamino)methyl)pyridin-2-yl)-1-oxoisoindolin-2-yl)piperidine-2,6-dione (116); 3-(1-oxo-5-(4-((((R)-1-phenylethyl)amino)methyl)pyridin-2-yl) isoindolin-2-yl)piperidine-2,6-dione (122); 3-(1-oxo-5-(4-(((((S)-1-phenylethyl)amino)methyl)pyridin-2-yl)isoindolin-2-yl) piperidine-2,6-dione (123); 3-(5-(4-((((1-hydroxycyclohexyl)methyl)amino)methyl)pyridin-2-yl)-1-oxoisoindolin-2-yl)piperidine-2,6-dione (124); 3-(5-(4-(((2-methyltetrahydro-2H-pyran-4-yl)amino)methyl)pyridin-2-yl)-1-oxoisoindolin-2-yl) piperidine-2,6-dione (126); 3-(5-

(4-(((4-hydroxybutyl)amino)methyl)pyridin-2-yl)-1-oxoisoindolin-2-yl)piperidine-2,6-dione (128); 3-(5-(4-(((oxetan-2-ylmethyl)amino)methyl)pyridin-2-yl)-1-oxoisoindolin-2-yl)piperidine-2,6-dione (129); 3-(5-(4-((((R)-3-hydroxy-1-phenylpropyl)amino)methyl)pyridin-2-yl)-1-oxoisoindolin-2-yl)piperidine-2,6-dione (131); 3-(5-(4-((methyl((S)-1-phenylethyl)amino)methyl)pyridin-2-yl)-1-oxoisoindolin-2-yl)piperidine-2,6-dione (136); 3-(5-(4-((methyl((R)-1-phenylethyl)amino)methyl)pyridin-2-yl)-1-oxoisoindolin-2-yl)piperidine-2,6-dione (137); 3-(5-(4-((methyl((1R,2R)-2-(methylamino)cyclohexyl)amino)methyl)pyridin-2-yl)-1-oxoisoindolin-2-yl)piperidine-2,6-dione (140); 3-(5-(4-((methyl(2-phenylpropan-2-yl)amino)methyl)pyridin-2-yl)-1-oxoisoindolin-2-yl)piperidine-2,6-dione (142); 3-(1-oxo-5-(4-((3-phenylpiperidin-1-yl)methyl)pyridin-2-yl)isoindolin-2-yl)piperidine-2,6-dione (144); 3-(5-{4-[(methylamino)methyl]pyridin-2-yl}-1-oxo-2,3-dihydro-1H-isoindol-2-yl) piperidine-2,6-dione (145); 4-{[({2-[2-(2,6-dioxopiperidin-3-yl)-1-oxo-2,3-dihydro-1H-isoindol-5-yl]pyridin-4-yl}methyl)(methyl)amino]methyl}-N,N-dimethylbenzene-1-sulfonamide (146); 3-(5-(4-(((4-fluorobenzyl)(methyl)amino)methyl)pyridin-2-yl)-1-oxoisoindolin-2-yl)piperidine-2,6-dione (147); 3-(5-(4-((methyl(3-(trifluoromethyl)benzyl)amino)methyl)pyridin-2-yl)-1-oxoisoindolin-2-yl)piperidine-2,6-dione (148); 3-(5-(4-((methyl(4-(trifluoromethyl)benzyl)amino)methyl)pyridin-2-yl)-1-oxoisoindolin-2-yl)piperidine-2,6-dione (149); 4-((((2-(2-(2,6-dioxopiperidin-3-yl)-1-oxoisoindolin-5-yl)pyridin-4-yl)methyl)(methyl)amino)methyl)benzonitrile (150); 3-(5-(4-((methyl(4-nitrobenzyl)amino)methyl)pyridin-2-yl)-1-oxoisoindolin-2-yl)piperidine-2,6-dione (151); 3-(5-(4-(((3,4-difluorobenzyl)(methyl)amino)methyl)pyridin-2-yl)-1-oxoisoindolin-2-yl)piperidine-2,6-dione (152); methyl 4-((((2-(2-(2,6-dioxopiperidin-3-yl)-1-oxoisoindolin-5-yl)pyridin-4-yl)methyl)(methyl)amino)methyl)benzoate (153); 3-(5-(4-(((4-chlorobenzyl)(methyl)amino)methyl)pyridin-2-yl)-1-oxoisoindolin-2-yl)piperidine-2,6-dione (154); 3-(5-(4-((methyl(quinolin-8-ylmethyl)amino)methyl)pyridin-2-yl)-1-oxoisoindolin-2-yl)piperidine-2,6-dione (155); 3-(5-(4-((methyl(3-(trifluoromethoxy)benzyl)amino)methyl)pyridin-2-yl)-1-oxoisoindolin-2-yl)piperidine-2,6-dione (156); 3-(5-(4-((methyl(4-(methylsulfonyl)benzyl)amino)methyl)pyridin-2-yl)-1-oxoisoindolin-2-yl)piperidine-2,6-dione (157); 3-(5-(4-(((3-methoxybenzyl)(methyl)amino)methyl)pyridin-2-yl)-1-oxoisoindolin-2-yl)piperidine-2,6-dione (158); 3-(5-(4-((methyl(pyridin-3-ylmethyl)amino)methyl)pyridin-2-yl)-1-oxoisoindolin-2-yl)piperidine-2,6-dione (159); 3-(5-(4-((methyl(pyridin-4-ylmethyl)amino)methyl)pyridin-2-yl)-1-oxoisoindolin-2-yl) piperidine-2,6-dione (160); 3-(5-(4-((methyl(4-methylbenzyl)amino)methyl)pyridin-2-yl)-1-oxoisoindolin-2-yl)piperidine-2,6-dione (161); 3-(5-(4-((methyl(naphthalen-2-ylmethyl)amino)methyl)pyridin-2-yl)-1-oxoisoindolin-2-yl)piperidine-2,6-dione (162); 3-(5-{4-[(dibenzylamino)methyl]pyridin-2-yl}-1-oxo-2,3-dihydro-1H-isoindol-2-yl) piperidine-2,6-dione (163); 3-[5-(4-{[benzyl(methyl)amino]methyl}pyridin-2-yl)-1-oxo-2,3-dihydro-1H-isoindol-2-yl]piperidine-2,6-dione (164); 3-{5-[4-({[(6-methoxypyridin-3-yl)methyl](methyl)amino}methyl)pyridin-2-yl]-1-oxo-2,3-dihydro-1H-isoindol-2-yl}piperidine-2,6-dione (168); 3-(5-(4-((((1H-indazol-4-yl)methyl)(methyl)amino)methyl)pyridin-2-yl)-1-oxoisoindolin-2-yl)piperidine-2,6-dione (169); 3-(5-(4-((methyl (1-methylpiperidin-4-yl)amino)methyl)pyridin-2-yl)-1-oxoisoindolin-2-yl)piperidine-2,6-dione (170); 3-(5-(4-((methyl(phenethyl)amino)methyl)pyridin-2-yl)-1-oxoisoindolin-2-yl)piperidine-2,6-dione (171); 3-(5-(4-(((furan-3-ylmethyl)(methyl)amino)methyl)pyridin-2-yl)-1-oxoisoindolin-2-yl)piperidine-2,6-dione (172); 3-(5-(4-(((cyclopropylmethyl)(methyl)amino)methyl)pyridin-2-yl)-1-oxoisoindolin-2-yl) piperidine-2,6-dione (173); 3-(5-(4-((methyl((1-methyl-1H-imidazol-5-yl)methyl)amino)methyl)pyridin-2-yl)-1-oxoisoindolin-2-yl)piperidine-2,6-dione (174); 3-(5-(4-((((cyclopentylmethyl)(methyl)amino)methyl)pyridin-2-yl)-1-oxoisoindolin-2-yl) piperidine-2,6-dione (175); 3-(5-(4-((methyl(thiazol-2-ylmethyl)amino)methyl)pyridin-2-yl)-1-oxoisoindolin-2-yl)piperidine-2,6-dione (176); 3-(5-(4-(((4-(1H-imidazol-1-yl)benzyl)(methyl)amino)methyl)pyridin-2-yl)-1-oxoisoindolin-2-yl)piperidine-2,6-dione (177); 3-(5-(4-(((cyclobutylmethyl)(methyl)amino)methyl)pyridin-2-yl)-1-oxoisoindolin-2-yl)piperidine-2,6-dione (178); 3-(5-(4-((isobutyl(methyl)amino)methyl)pyridin-2-yl)-1-oxoisoindolin-2-yl)piperidine-2,6-dione (179); 3-(5-(4-((isopentyl(methyl)amino)methyl)pyridin-2-yl)-1-oxoisoindolin-2-yl)piperidine-2,6-dione (180); 3-(5-(4-(((1-hydroxypropan-2-yl)(methyl)amino)methyl)pyridin-2-yl)-1-oxoisoindolin-2-yl) piperidine-2,6-dione (181); 3-(5-(4-((methyl((tetrahydrofuran-3-yl)methyl)amino)methyl)pyridin-2-yl)-1-oxoisoindolin-2-yl)piperidine-2,6-dione (182); 3-(5-(4-((methyl (quinoxalin-2-ylmethyl)amino)methyl)pyridin-2-yl)-1-oxoisoindolin-2-yl)piperidine-2,6-dione (183); 3-(5-(4-((methyl(3,3,3-trifluoropropyl)amino)methyl)pyridin-2-yl)-1-oxoisoindolin-2-yl)piperidine-2,6-dione (184); 3-(5-(4-(((4-hydroxybutan-2-yl)(methyl)amino)methyl)pyridin-2-yl)-1-oxoisoindolin-2-yl)piperidine-2,6-dione (185); or 3-(5-(4-((dimethylamino)methyl)pyridin-2-yl)-6-methyl-1-oxoisoindolin-2-yl)piperidine-2,6-dione (194).

One embodiment provides a compound of Formula (I) or a salt thereof, wherein said compound is 3-(5-(4-((ethyl(methyl)amino)methyl)pyridin-2-yl)-1-oxoisoindolin-2-yl) piperidine-2,6-dione (6); 3-(1-oxo-5-(4-(pyrrolidin-1-ylmethyl)pyridin-2-yl)isoindolin-2-yl)piperidine-2,6-dione (8); 3-(1-oxo-5-(4-((4-(2-oxo-2,3-dihydro-1H-benzo[d]imidazol-1-yl)piperidin-1-yl)methyl)pyridin-2-yl)isoindolin-2-yl)piperidine-2,6-dione (11); 3-(5-(4-((4-(benzo[d][1,3]dioxol-5-ylmethyl)piperazin-1-yl)methyl)pyridin-2-yl)-1-oxoisoindolin-2-yl)piperidine-2,6-dione (12); 1-((2-(2-(2,6-dioxopiperidin-3-yl)-1-oxoisoindolin-5-yl)pyridin-4-yl)methyl)-N,N-diethylpiperidine-3-carboxamide (13); 3-(5-(4-((4-methylpiperidin-1-yl)methyl)pyridin-2-yl)-1-oxoisoindolin-2-yl)piperidine-2,6-dione (14); 3-(1-oxo-5-(4-((4-(pyridin-2-yl)piperidin-1-yl)methyl)pyridin-2-yl)isoindolin-2-yl)piperidine-2,6-dione (15); 3-(5-(4-(([1,4'-bipiperidin]-1'-ylmethyl)pyridin-2-yl)-1-oxoisoindolin-2-yl)piperidine-2,6-dione (17); 3-(1-oxo-5-(4-((4-(pyrimidin-2-yl)piperidin-1-yl)methyl)pyridin-2-yl)isoindolin-2-yl)piperidine-2,6-dione (18); 3-(5-(4-((2-methylpyrrolidin-1-yl)methyl)pyridin-2-yl)-1-oxoisoindolin-2-yl)piperidine-2,6-dione (20); 3-(1-oxo-5-(4-((4-(pyrrolidin-1-yl)piperidin-1-yl)methyl)pyridin-2-yl)isoindolin-2-yl)piperidine-2,6-dione (23); 3-(5-(4-((4-(furan-2-carbonyl)piperazin-1-yl)methyl)pyridin-2-yl)-1-oxoisoindolin-2-yl)piperidine-2,6-dione (24); 3-(1-oxo-5-(4-((4-(pyridin-4-yl)piperazin-1-yl)methyl)pyridin-2-yl)isoindolin-2-yl)piperidine-2,6-dione (25); 3-(1-oxo-5-(4-((4-(pyrazin-2-yl)piperazin-1-yl)methyl)pyridin-2-yl)isoindolin-2-yl)piperidine-2,6-dione (26); 3-(5-(4-((3-methyl-4-(m-tolyl)piperazin-1-yl)methyl)pyridin-2-yl)-1-oxoisoindolin-2-yl)piperidine-2,6-dione (27); 3-(5-(4-((4-acetylpiperazin-1-yl)methyl)pyridin-2-yl)-1-oxoisoindolin-2-yl)piperidine-2,6-dione (28); 3-(5-(4-((2-(((S)-1-methylpyrrolidin-2-yl)methyl)piperidin-1-yl)methyl)pyridin-2-yl)-1-oxoisoindolin-2-yl)piperidine-2,6-dione (30); N-((3S)-1-((2-(2-(2,6-dioxopiperidin-3-yl)-1- oxoisoindolin-5-yl)pyridin-4-yl)methyl)pyrrolidin-3-yl) acetamide (31); 3-(1-oxo-5-(4-((4-(tetrahydrofuran-2-carbonyl)piperazin-1-yl)methyl)pyridin-2-yl)isoindolin-2-yl) piperidine-2,6-dione (32); 3-(5-(4-(((S)-3-(dimethylamino)pyrrolidin-1-yl)methyl) pyridin-2-yl)-1-oxoisoindolin-2-yl)piperidine-2,6-dione (33); 3-(5-(4-((4-methylpiperazin-1-yl)methyl)pyridin-2-yl)-1-oxoisoindolin-2-yl)piperidine-2,6-dione (35); 3-(5-(4-(((4-benzylpiperazin-1-yl)methyl)pyridin-2-yl)-1-oxoisoindolin-2-yl) piperidine-2,6-dione (36); 3-(1-oxo-5-(4-((3-oxopiperazin-1-yl)methyl)pyridin-2-yl) isoindolin-2-yl) piperidine-2,6-dione (37); 3-(5-(4-((4-benzylpiperidin-1-yl)methyl)pyridin-2-yl)-1-oxoisoindolin-2-yl)piperidine-2,6-dione (38); 3-(5-(4-((3,4-dihydroisoquinolin-2(1H)-yl)methyl)pyridin-2-yl)-1-oxoisoindolin-2-yl)piperidine-2,6-dione (39); 3-(5-(4-((4-(dimethylamino)piperidin-1-yl)methyl)pyridin-2-yl)-1-oxoisoindolin-2-yl)piperidine-2,6-dione (40); 1-((2-(2-(2,6-dioxopiperidin-3-yl)-1-oxoisoindolin-5-yl)pyridin-4-yl)methyl)piperidine-4-carboxamide (41); 3-(5-(4-((4-benzhydrylpiperidin-1-yl) methyl)pyridin-2-yl)-1-oxoisoindolin-2-yl)piperidine-2,6-dione (42); 3-(5-(4-((4-methyl-1,4-diazepan-1-yl)methyl) pyridin-2-yl)-1-oxoisoindolin-2-yl) piperidine-2,6-dione (43); 3-(5-(4-((4-isopropylpiperazin-1-yl)methyl)pyridin-2-yl)-1-oxoisoindolin-2-yl)piperidine-2,6-dione (44); 3-(5-(4-(((R)-3-(dimethylamino)pyrrolidin-1-yl)methyl)pyridin-2-yl)-1-oxoisoindolin-2-yl)piperidine-2,6-dione (45); 3-(5-(4-((2-methylazetidin-1-yl)methyl)pyridin-2-yl)-1-oxoisoindolin-2-yl)piperidine-2,6-dione (46); 3-(5-(4-((3-methylazetidin-1-yl)methyl)pyridin-2-yl)-1-oxoisoindolin-2-yl)piperidine-2,6-dione (47); 3-(5-(4-(azepan-1-ylmethyl) pyridin-2-yl)-1-oxoisoindolin-2-yl)piperidine-2,6-dione (48); 3-(5-(4-((3,3-dimethylazetidin-1-yl)methyl)pyridin-2-yl)-1-oxoisoindolin-2-yl)piperidine-2,6-dione (51); 3-(5-(4-((2,2-dimethylazetidin-1-yl)methyl)pyridin-2-yl)-1-oxoisoindolin-2-yl)piperidine-2,6-dione (52); 3-(5-(4-((2,6-dimethylpiperidin-1-yl)methyl)pyridin-2-yl)-1-oxoisoindolin-2-yl)piperidine-2,6-dione (53); 3-(5-(4-((hexahydrocyclopenta[b]pyrrol-1(2H)-yl)methyl)pyridin-2-yl)-1-oxoisoindolin-2-yl) piperidine-2,6-dione (60); 3-(5-(4-(((S)-2-methylpyrrolidin-1-yl)methyl)pyridin-2-yl)-1-oxoisoindolin-2-yl)piperidine-2,6-dione (69); 3-(5-(4-(((R)-3-methylpyrrolidin-1-yl)methyl)pyridin-2-yl)-1-oxoisoindolin-2-yl)piperidine-2,6-dione (70); 3-(5-(4-(((R)-2-methylpiperidin-1-yl)methyl)pyridin-2-yl)-1-oxoisoindolin-2-yl)piperidine-2,6-dione (71); 3-(5-(4-(((S)-3-methylpyrrolidin-1-yl)methyl)pyridin-2-yl)-1-oxoisoindolin-2-yl) piperidine-2,6-dione (72); 3-(5-(4-(((S)-3-methylpiperidin-1-yl)methyl)pyridin-2-yl)-1-oxoisoindolin-2-yl)piperidine-2,6-dione (73); 3-(5-(4-(((S)-2-methylpiperidin-1-yl)methyl)pyridin-2-yl)-1-oxoisoindolin-2-yl)piperidine-2,6-dione (74); 3-(5-(4-(((R)-3-methylpiperidin-1-yl)methyl)pyridin-2-yl)-1-oxoisoindolin-2-yl)piperidine-2,6-dione (75); 3-(1-oxo-5-(4-((2-phenylazetidin-1-yl)methyl)pyridin-2-yl)isoindolin-2-yl) piperidine-2,6-dione (76); 3-(5-(4-(((3aR,6aS)-5-methylhexahydropyrrolo[3,4-c]pyrrol-2(1H)-yl)methyl) pyridin-2-yl)-1-oxoisoindolin-2-yl)piperidine-2,6-dione (78); 3-(5-(4-((2-oxa-5-azabicyclo[2.2.1]heptan-5-yl) methyl)pyridin-2-yl)-1-oxoisoindolin-2-yl) piperidine-2,6-dione (79); 3-(5-(4-(((3S,5R)-3,5-dimethylpiperidin-1-yl) methyl)pyridin-2-yl)-1-oxoisoindolin-2-yl)piperidine-2,6-dione (81); 3-(5-(4-((4,4-dimethylpiperidin-1-yl)methyl) pyridin-2-yl)-1-oxoisoindolin-2-yl)piperidine-2,6-dione (82); 3-(1-oxo-5-(4-((3-phenylazetidin-1-yl)methyl)pyridin-2-yl)isoindolin-2-yl)piperidine-2,6-dione (83); 3-(5-(4-((3,3-dimethylpiperidin-1-yl)methyl)pyridin-2-yl)-1-oxoisoindolin-2-yl)piperidine-2,6-dione (85); 3-(5-(4-((2,2-dimethylpyrrolidin-1-yl)methyl)pyridin-2-yl)-1-oxoisoindolin-2-yl)piperidine-2,6-dione (117); 3-(5-(4-((3,3-dimethylpyrrolidin-1-yl)methyl)pyridin-2-yl)-1-oxoisoindolin-2-yl)piperidine-2,6-dione (118); 3-(5-(4-((2,5-dimethylpyrrolidin-1-yl)methyl)pyridin-2-yl)-1-oxoisoindolin-2-yl)piperidine-2,6-dione (119); 3-(5-(4-(((2R,6S)-2,6-dimethylpiperidin-1-yl)methyl)pyridin-2-yl)-1-oxoisoindolin-2-yl)piperidine-2,6-dione (120); 3-(5-(4-((4-(4-aminophenyl)-4-methylpiperidin-1-yl)methyl) pyridin-2-yl)-1-oxoisoindolin-2-yl)piperidine-2,6-dione (121); 3-(5-(4-(((R)-2-methylpyrrolidin-1-yl)methyl)pyridin-2-yl)-1-oxoisoindolin-2-yl) piperidine-2,6-dione (125); 3-(5-(4-((6-azaspiro[2.5]octan-6-yl)methyl)pyridin-2-yl)-1-oxoisoindolin-2-yl)piperidine-2,6-dione (127); 3-(5-(4-((3-isopropoxyazetidin-1-yl)methyl)pyridin-2-yl)-1-oxoisoindolin-2-yl)piperidine-2,6-dione (130); 3-(1-oxo-5-(4-((4-tosylpiperidin-1-yl)methyl)pyridin-2-yl)isoindolin-2-yl) piperidine-2,6-dione (132); 3-(1-oxo-5-(4-(((S)-2-phenylpyrrolidin-1-yl)methyl)pyridin-2-yl)isoindolin-2-yl) piperidine-2,6-dione (133); 3-(1-oxo-5-(4-(((R)-2-phenylpyrrolidin-1-yl)methyl)pyridin-2-yl) isoindolin-2-yl) piperidine-2,6-dione (134); 3-(1-oxo-5-(4-(((S)-3-phenylpiperidin-1-yl)methyl)pyridin-2-yl)isoindolin-2-yl) piperidine-2,6-dione (135); 3-(1-oxo-5-(4-(((R)-3-phenylpyrrolidin-1-yl)methyl)pyridin-2-yl)isoindolin-2-yl) piperidine-2,6-dione (138); 3-(1-oxo-5-(4-(((S)-3-phenylpyrrolidin-1-yl)methyl)pyridin-2-yl)isoindolin-2-yl) piperidine-2,6-dione (139); 3-(1-oxo-5-(4-((4-phenylpiperidin-1-yl)methyl)pyridin-2-yl)isoindolin-2-yl) piperidine-2,6-dione (141); 3-(1-oxo-5-(4-((3-phenylpiperidin-1-yl)methyl)pyridin-2-yl)isoindolin-2-yl) piperidine-2,6-dione (143); 3-(5-{4-[(azetidin-1-yl)methyl] pyridin-2-yl}-1-oxo-2,3-dihydro-1H-isoindol-2-yl) piperidine-2,6-dione (165); 3-(5-{4-[(morpholin-4-yl) methyl]pyridin-2-yl}-1-oxo-2,3-dihydro-1H-isoindol-2-yl) piperidine-2,6-dione (166); 4-({2-[2-(2,6-dioxopiperidin-3-yl)-1-oxo-2,3-dihydro-1H-isoindol-5-yl]pyridin-4-yl}methyl)-1λ6-thiomorpholine-1,1-dione (167); 3-(5-(5-chloro-4-((3-phenylazetidin-1-yl)methyl)pyridin-2-yl)-1-oxoisoindolin-2-yl)piperidine-2,6-dione (186); 3-(5-(5-chloro-4-((2-phenylazetidin-1-yl)methyl)pyridin-2-yl)-1-oxoisoindolin-2-yl)piperidine-2,6-dione (187); 3-(5-(5-fluoro-4-((3-phenylazetidin-1-yl)methyl)pyridin-2-yl)-1-oxoisoindolin-2-yl) piperidine-2,6-dione (188); 3-(5-(5-fluoro-4-((2-phenylazetidin-1-yl)methyl)pyridin-2-yl)-1-oxoisoindolin-2-yl)piperidine-2,6-dione (189); 3-(5-(5-fluoro-4-((3-(pyridin-3-yl)azetidin-1-yl)methyl)pyridin-2-yl)-1-oxoisoindolin-2-yl) piperidine-2,6-dione (190); 3-(5-(3-fluoro-4-((3-phenylazetidin-1-yl)methyl)pyridin-2-yl)-1-oxoisoindolin-2-yl) piperidine-2,6-dione (191); 3-(5-(3-fluoro-4-((3-(pyridin-3-yl)azetidin-1-yl)methyl)pyridin-2-yl)-1-oxoisoindolin-2-yl)piperidine-2,6-dione (192); 3-(5-(3-fluoro-4-((2-phenylazetidin-1-yl)methyl)pyridin-2-yl)-1-oxoisoindolin-2-yl) piperidine-2,6-dione (193); 3-(1-oxo-5-(4-((3-(pyridin-4-yl)azetidin-1-yl)methyl)pyridin-2-yl) isoindolin-2-yl)piperidine-2,6-dione (195); 3-(5-(4-((3-methoxy-3-methylazetidin-1-yl)methyl)pyridin-2-yl)-1-oxoisoindolin-2-yl)piperidine-2,6-dione (196); 3-(5-(4-((3-methoxyazetidin-1-yl)methyl)pyridin-2-yl)-1-oxoisoindolin-2-yl)piperidine-2,6-dione (197); 3-(5-(4-((3-ethoxyazetidin-1-yl)methyl)pyridin-2-yl)-1-oxoisoindolin-2-yl) piperidine-2,6-dione (198); 3-(1-oxo-5-(4-((4-(p-tolyl) piperidin-1-yl)methyl)pyridin-2-yl) isoindolin-2-yl) piperidine-2,6-dione (199); 3-(5-(4-(((S)-2-benzylaziridin-1-yl)methyl)pyridin-2-yl)-1-oxoisoindolin-2-yl)piperidine-2,6-dione (200); 3-(5-(4-((2-methylaziridin-1-yl)methyl)

pyridin-2-yl)-1-oxoisoindolin-2-yl)piperidine-2,6-dione (201); 1-((2-(2-(2,6-dioxopiperidin-3-yl)-1-oxoisoindolin-5-yl)pyridin-4-yl)methyl)-N,N-dimethylazetidine-3-carboxamide (202); 3-(1-oxo-5-(4-((3-(pyridin-3-yl)azetidin-1-yl)methyl)pyridin-2-yl) isoindolin-2-yl)piperidine-2,6-dione (203); 3-(1-oxo-5-(4-((2-phenylazetidin-1-yl)methyl)pyridin-2-yl)isoindolin-2-yl)piperidine-2,6-dione (204-205); 1-((2-(2-(2,6-dioxopiperidin-3-yl)-1-oxoisoindolin-5-yl)pyridin-4-yl)methyl)azetidine-2-carboxamide (206); 3-(5-(4-((4-methoxy-3,3-dimethylpiperidin-1-yl)methyl)pyridin-2-yl)-1-oxoisoindolin-2-yl) piperidine-2,6-dione (207); or 3-(4-fluoro-1-oxo-5-(4-((3-phenylazetidin-1-yl)methyl)pyridin-2-yl)isoindolin-2-yl)piperidine-2,6-dione (208).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —$NH_2$.
The term "oxo" refers to the group =O.
The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "alkoxy," as used herein, refers to an alkyl group attached to the parent molecular moiety through an oxygen atom, for example, methoxy group (—$OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The compounds of the present invention include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salt(s) formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 203).

e) Rautio, J. et al., *Nature Review Drug Discovery,* 17, 559-587, (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

The term "Helios inhibitor" refers to an agent capable of decreasing Helios protein levels, decreasing Helios activity level and/or inhibiting Helios expression level in the cells to control Treg differentiation. The Helios inhibitor may be a reversible or irreversible inhibitor.

As used herein, "Helios" protein refers a protein that is a member of the Ikaros family of zinc finger proteins. In humans, Helios is encoded by the IKZF2 gene. Helios is also known as IKAROS family zinc finger 2, ANF1A2, ZNF1A2, ZNFN1A2, zinc finger protein, subfamily 1A, 2, and Ikaros family zinc finger protein 2. The members of this protein family include Ikaros, Helios, Aiolos, Eos, and Pegasus. As used herein Helios protein includes various isoforms, which includes the isoforms 1-5 listed below.

Isoform 1 (UniProt Q9UKS7-1)
(SEQ ID NO: 1)
METEAIDGYITCDNELSPEREHSNMAIDLTSSTPNGQHASPSHMTSTNSV

KLEMQSDEECDRKPLSREDEIRGHDEGSSLEEPLIESSEVADNRKVQELQ

GEGGIRLPNGKLKCDVCGMVCIGPNVLMVHKRSHTGERPFHCNQCGASFT

QKGNLLRHIKLHSGEKPFKCPFCSYACRRRDALTGHLRTHSVGKPHKCNY

CGRSYKQRSSLEEHKERCHNYLQNVSMEAAGQVMSHHVPPMEDCKEQEPI

MDNNISLVPFERPAVIEKLTGNMGKRKSSTPQKFVGEKLMRFSYPDIHFD

MNLTYEKEAELMQSHMMDQAINNAITYLGAEALHPLMQHPPSTIAEVAPV

ISSAYSQVYHPNRIERPISRETADSHENNMDGPISLIRPKSRPQEREASP

SNSCLDSTDSESSHDDHQSYQGHPALNPKRKQSPAYMKEDVKALDTTKAP

KGSLKDIYKVFNGEGEQIRAFKCEHCRVLFLDHVMYTIHMGCHGYRDPLE

CNICGYRSQDRYEFSSHIVRGEHTFH

Isoform 2 (UniProt Q9UKS7-2)
(SEQ ID NO: 2)
METEAIDGYITCDNELSPEREHSNMAIDLTSSTPNGQHASPSHMTSTNSV

KLEMQSDEECDRKPLSREDEIRGHDEGSSLEEPLIESSEVADNRKVQELQ

GEGGIRLPNGERPFHCNQCGASFTQKGNLLRHIKLHSGEKPFKCPFCSYA

CRRRDALTGHLRTHSVGKPHKCNYCGRSYKQRSSLEEHKERCHNYLQNVS

MEAAGQVMSHHVPPMEDCKEQEPIMDNNISLVPFERPAVIEKLTGNIVIG

KRKSSTPQKFVGEKLMRFSYPDIHFDMNLTYEKEAELMQSHMMDQAINNA

ITYLGAEALHPLMQHPPSTIAEVAPVISSAYSQVYHPNRIERPISRETAD

SHENNMDGPISLIRPKSRPQEREASPSNSCLDSTDSESSHDDHQSYQGHP

ALNPKRKQSPAYMKEDVKALDTTKAPKGSLKDIYKVFNGEGEQIRAFKCE

HCRVLFLDHVMYTIHMGCHGYRDPLECNICGYRSQDRYEFSSHIVRGEHT

FH

Isoform 4 (UniProt Q9UKS7-4)
(SEQ ID NO: 3)
METEAIDGYITCDNELSPEREHSNMAIDLTSSTPNGQHASPSHMTSTNSV

KLEMQSDEECDRKPLSREDEIRGHDEGSSLEEPLIESSEVADNRKVQELQ

GEGGIRLPNGERPFHCNQCGASFTQKGNLLRHIKLHSGEKPFKCPFCSYA

CRRRDALTGHLRTHSVGKPHKCNYCGRSYKQRSSLEEHKERCHNYLQNVS

MEAAGQVMSHHGEKLMRFSYPDIHFDMNLTYEKEAELMQSHMMDQAINNA

ITYLGAEALHPLMQHPPSTIAEVAPVISSAYSQVYHPNRIERPISRETAD

SHENNMDGPISLIRPKSRPQEREASPSNSCLDSTDSESSHDDHQSYQGHP

ALNPKRKQSPAYMKEDVKALDTTKAPKGSLKDIYKVFNGEGEQIRAFKCE

HCRVLFLDHVMYTIHMGCHGYRDPLECNICGYRSQDRYEFSSHIVRGEHT

FH

Isoform 6 (UniProt Q9UKS7-6)
(SEQ ID NO: 4)
METEAIDGYITCDNELSPEREHSNMAIDLTSSTPNGQHASPSHMTSTNSV

KLEMQSDEECDRKPLSREDEIRGHDEGSSLEEPLIESSEVADNRKVQELQ

GEGGIRLPNGKLKCDVCGMVCIGPNVLMVHKRSHTGERPFHCNQCGASFT

QKGNLLRHIKLHSGEKPFKCPFCSYACRRRDALTGHLRTHSVGKPHKCNY

CGRSYKQRSSLEEHKERCHNYLQNVSMEAAGQVMSHHDS

Isoform 7 (UniProt Q9UKS7-7)
(SEQ ID NO: 5)
METEAIDGYITCDNELSPEREHSNMAIDLTSSTPNGQHASPSHMTSTNSV

KLEMQSDEECDRKPLSREDEIRGHDEGSSLEEPLIESSEVADNRKVQELQ

GEGGIRLPNGERPFHCNQCGASFTQKGNLLRHIKLHSGEKPFKCPFCSYA

CRRRDALTGHLRTHSVPPMEDCKEQEPIMDNNISLVPFERPAVIEKLTGN

IVIGKRKSSTPQKFVGEKLMRFSYPDIHFDMNLTYEKEAELMQSHMMDQA

INNAITYLGAEALHPLMQHPPSTIAEVAPVISSAYSQVYHPNRIERPISR

ETADSHENNMDGPISLIRPKSRPQEREASPSNSCLDSTDSESSHDDHQSY

QGHPALNPKRKQSPAYMKEDVKALDTTKAPKGSLKDIYKVFNGEGEQIRA

FKCEHCRVLFLDHVMYTIHMGCHGYRDPLECNICGYRSQDRYEFSSHIVR

GEHTFH

The "Helios" isoforms 1, 2, 4, 6, and 7 listed above includes the degron FHCNQCGASFTQKGNLLRHIKLH (SEQ ID NO: 6) (bold and underlined). A degron is a portion of a protein that plays a role in regulating protein degradation rates.

As used herein, "Eos" protein is encoded by the IKZF4 gene, and is also known as IKAROS family zinc finger 4, ZNFN1A4, zinc finger protein, subfamily 1A, 4, Ikaros family zinc finger protein 4, and KIAA1782. "Eos" protein includes isoforms encoded by the following two human isoforms 1 (Q9H2S9-1) and 2 (Q9H2S9-2):

Isoform 1 (UniProt Q9H2S9-1)
(SEQ ID NO: 7)
MHTPPALPRRFQGGGRVRTPGSHRQGKDNLERDPSGGCVPDFLPQAQDS

NHFIMESLFCESSGDSSLEKEFLGAPVGPSVSTPNSQHSSPSRSLSANSI

KVEMYSDEESSRLLGPDERLLEKDDSVIVEDSLSEPLGYCDGSGPEPHSP

GGIRLPNGKLKCDVCGMVCIGPNVLMVHKRSHTGERPFHCNQCGASFTQK

GNLLRHIKLHSGEKPFKCPFCNYACRRRDALTGHLRTHSVSSPTVGKPYK

CNYCGRSYKQQSTLEEHKERCHNYLQSLSTEAQALAGQPGDEIRDLEMVP

DSMLHSSSERPTFIDRLANSLTKRKRSTPQKFVGEKQMRFSLSDLPYDVN

SGGYEKDVELVAHHSLEPGFGSSLAFVGAEHLRPLRLPPTNCISELTPVI

SSVYTQMQPLPGRLELPGSREAGEGPEDLADGGPLLYRPRGPLTDPGASP

SNGCQDSTDTESNHEDRVAGVVSLPQGPPPQPPPTIVVGRHSPAYAKEDP

KPQEGLLRGTPGPSKEVLRVVGESGEPVKAFKCEHCRILFLDHVMFTIHM

GCHGFRDPFECNICGYHSQDRYEFSSHIVRGEHKVG

Isoform 2 (UniProt Q9H2S9-2)
(SEQ ID NO: 8)
MDSRYLQLQLYLPSCSLLQGSGDSSLEKEFLGAPVGPSVSTPNSQHSSPS

RSLSANSIKVEMYSDEESSRLLGPDERLLEKDDSVIVEDSLSEPLGYCDG

SGPEPHSPGGIRLPNGKLKCDVCGMVCIGPNVLMVHKRSHTGERPFHCNQ

CGASFTQKGNLLRHIKLHSGEKPFKCPFCNYACRRRDALTGHLRTHSVSS

PTVGKPYKCNYCGRSYKQQSTLEEHKERCHNYLQSLSTEAQALAGQPGDE

IRDLEMVPDSMLHSSSERPTFIDRLANSLTKRKRSTPQKFVGEKQMRFSL

SDLPYDVNSGGYEKDVELVAHHSLEPGFGSSLAFVGAEHLRPLRLPPTNC

```
ISELTPVISSVYTQMQPLPGRLELPGSREAGEGPEDLADGGPLLYRPRGP

LTDPGASPSNGCQDSTDTESNHEDRVAGVVSLPQGPPPQPPPTIVVGRHS

PAYAKEDPKPQEGLLRGTPGPSKEVLRVVGESGEPVKAFKCEHCRILFLD

HVMFTIHMGCHGFRDPFECNICGYHSQDRYEFSSHIVRGEHKVG
```

The "Eos" protein isoforms 1 and 2 listed above includes the degron FHCNQCGASFTQKGNLLRHIKLH (SEQ ID NO: 6) (bold and underlined), which is the same as the degron for the "Helios" protein.

As used herein, "Ikaros" protein is encoded by the IKZF1 gene. Ikaros is also known as IKAROS family zinc finger 1, ZNFN1A1, zinc finger protein, subfamily 1A, 1, Ikaros family zinc finger protein 1, IK1, lymphoid transcription factor LyF-1, Hs.54452, PPP1R92, protein phosphatase 1, regulatory subunit 92, PRO0758, CVID13, and CLL-associated antigen KW-6. Ikaros protein includes isoforms encoded by amino acid sequences Q13422-1, Q13422-2, Q13422-3, Q13422-4, Q13422-7, and Q13422-8. Ikaros protein also includes isoforms encoded by amino acid sequences Q13422-5 and Q13422-6.

As used herein, "Aiolos" protein is encoded by the IKZF3 gene. Aiolos protein is also known as IKAROS family zinc finger 3, ZNFN1A3, zinc finger protein, subfamily 1A, 3, Ikaros family zinc finger protein 3, and AIO. Aiolos protein includes isoforms encoded by amino acid sequences Q9UKT9-1, Q9UKT9-3, Q9UKT9-4, Q9UKT9-6, Q9UKT9-7, Q9UKT9-8, Q9UKT9-9, and Q9UKT9-14. Aiolos protein also includes isoforms encoded by amino acid sequences Q9UKT9-2, Q9UKT9-5, Q9UKT9-10, Q9UKT9-11, Q9UKT9-12, and Q9UKT9-13, Q9UKT9-15, and Q9UKT9-16.

As used herein, "Pegasus" protein is also known as IKAROS family zinc finger 5, ZNFN1A5, zinc finger protein, subfamily 1A, 5, and Ikaros family zinc finger protein 5. Pegasus is encoded by the IKZF5 gene.

As used herein, the term "contacting" refers to the bringing together of indicated moieties in an in vitro system or an in vivo system. For example, "contacting" Helios protein with a compound of Formula (I) includes the administration of a compound of the present invention to an individual or patient, such as a human, having Helios protein, as well as, for example, introducing a compound of Formula (I) into a sample containing a cellular or purified preparation containing Helios protein.

The terms "treat," "treating," and "treatment," as used herein, refer to any type of intervention or process performed on, or administering an active agent to the subject with the objective of reversing, alleviating, ameliorating, inhibiting, or slowing down or preventing the progression, development, severity or recurrence of a symptom, complication, condition or biochemical indicia associated with a disease. By contrast, "prophylaxis" or "prevention" refers to administration to a subject who does not have a disease to prevent the disease from occurring. "Treat," "treating," and "treatment" does not encompass prophylaxis or prevention.

"Therapeutically effective amount" is intended to include an amount of a compound of the present invention alone or an amount of the combination of compounds claimed or an amount of a compound of the present invention in combination with other active ingredients effective to decrease Helios protein levels, decrease Helios activity levels and/or inhibit Helios expression levels in the cells, or effective to treat or prevent viral infections and proliferative disorders, such as cancer.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

The term "patient" includes human and other mammalian subjects that receive either therapeutic or prophylactic treatment.

The term "subject" includes any human or non-human animal. For example, the methods and compositions herein disclosed can be used to treat a subject having cancer. A non-human animal includes all vertebrates, e.g., mammals and non-mammals, including non-human primates, sheep, dogs, cows, chickens, amphibians, reptiles, etc. In one embodiment, the subject is a human subject.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms; and not injurious to the patient.

The term "pharmaceutical composition" means a composition comprising a compound of the invention in combination with at least one additional pharmaceutically acceptable carrier.

UTILITY

The compounds of Formula (I) are useful for the treatment of cancer.

In one embodiment, the present invention provides a combined preparation of a compound of Formula (I), and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the activity of Helios protein. The combined preparation can be used to decrease Helios protein level, Helios activity level and/or Helios expression level in the cells to control Treg differentiation.

The compounds for Formula (I) and pharmaceutical compositions comprising at least one compound of Formula (I) are useful in treating or preventing any diseases or conditions that are associated with the activity of Helios protein. These include viral and other infections (e.g., skin infections, GI infection, urinary tract infections, genito-urinary infections, systemic infections), and proliferative diseases (e.g., cancer). The compounds of Formula (I) and pharmaceutical compositions comprising in at least one compound of Formula (I) may be administered to animals, preferably mammals (e.g., domesticated animals, cats, dogs, mice, rats), and more preferably humans. Any method of administration may be used to deliver the compound or pharmaceutical composition to the patient. In certain embodiments, the compound of Formula (I) or pharmaceutical composition comprising at least compound of Formula (I) is administered orally. In other embodiments, the Formula (I) or pharmaceutical composition comprising at least compound of Formula (I) is administered parenterally.

The compounds of Formula (I) can selectively decrease Helios protein levels, decrease Helios activity levels and/or inhibit Helios expression levels in the cells to control Treg differentiation. For example, the compounds of Formula (I) can be used to selectively decrease Helios activity levels and/or inhibit Helios expression levels in the cells to control Treg differentiation in a cell or in an individual in need of a decrease in Helios protein levels, decrease in Helios activity levels and/or inhibition of Helios expression level by administering an inhibiting amount of a compound of Formula (I) or a salt thereof.

In one aspect, the compound(s) of Formula (I) are sequentially administered prior to administration of the immuno-oncology agent. In another aspect, compound(s) of Formula (I) are administered concurrently with the immuno-oncology agent. In yet another aspect, compound(s) of Formula (I) are sequentially administered after administration of the immuno-oncology agent.

In another aspect, compounds of Formula (I) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In one aspect, T cell responses can be stimulated by a combination of a compound of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of Formula (I) for the treatment of cancer include antagonists of inhibitory receptors on NK cells or agonists of activating receptors on NK cells. For example, compounds of Formula (I) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13/69264; WO14/036357).

In another aspect, compounds of Formula (I) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO207/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO206/122150, WO07/75598, WO08/

36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Types of cancers that may be treated with the compound of Formula (I) include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of Formula (I) for treatment of Helios protein associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of Formula (I) include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds of Formula (I) may also be combined with immunotherapy drugs, including cytokines such as interferon alpha, interleukin 2, and tumor necrosis factor (TNF) in the treatment of melanoma.

Compounds of Formula (I) may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of Formula (I), using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 38.9° C. to 40° C. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (200)); (v) cell cycle kinase inhibitors such as, for example, flavopiridol and UCN-O1 (see, for example, Sausville, *Curr. Med. Chem. Anti-Canc. Agents*, 3:47-56 (203)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one compound of Formula (I) may be in separate pharmaceutical compositions. In a specific embodiment of the present invention, at least one compound of Formula (I) and at least one STI may be administered to the patient concurrently or sequentially. In other words, at least one compound of Formula (I) may be administered first, at least one STI may be administered first, or at least one compound of Formula (I) and at least one STI may be administered at the same time. Additionally, when more than one compound of Formula (I) and/or STI is used, the compounds may be administered in any order.

The present invention further provides a pharmaceutical composition for the treatment of a chronic viral infection in a patient comprising at least one compound of Formula (I), optionally, at least one chemotherapeutic drug, and, optionally, at least one antiviral agent, in a pharmaceutically acceptable carrier.

Also provided is a method for treating a chronic viral infection in a patient by administering an effective amount of the above pharmaceutical composition.

In a specific embodiment of the present invention, at least one compound of Formula (I) and at least one chemotherapeutic agent are administered to the patient concurrently or sequentially. In other words, at least one compound of Formula (I) may be administered first, at least one chemotherapeutic agent may be administered first, or at least one compound of Formula (I) and the at least one STI may be administered at the same time. Additionally, when more than one compound of Formula (I) and/or chemotherapeutic agent is used, the compounds may be administered in any order. Similarly, any antiviral agent or STI may also be administered at any point in comparison to the administration of the compound of Formula (I).

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV).

Suitable antiviral agents contemplated for use in combination with the compound of Formula (I) can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions

The invention also provides pharmaceutically compositions which comprise a therapeutically effective amount of one or more of the compounds of Formula (I), formulated together with one or more pharmaceutically acceptable carriers (additives) and/or diluents, and optionally, one or more additional therapeutic agents described above.

The compounds of Formula (I) may be administered by any suitable route, preferably in the form of a pharmaceutical composition adapted to such a route, and in a dose effective for the treatment intended. The compounds and compositions of the compound of Formula (I) can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also includes pharmaceutical kits useful, for example, in the treatment or prevention of Helios protein-associated diseases or disorders, and other diseases referred to herein which include one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of Formula (I) may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 200 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of Formula (I) (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of Formula (I) (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of Formula (I), alone or in combination with a pharmaceutical carrier. Optionally, compounds of Formula (I) can be used alone, in combination with other compounds of Formula (I), or in combination with one or more other therapeutic agent(s), e.g., an anticancer agent or other pharmaceutically active material.

Regardless of the route of administration selected, the compounds of Formula (I), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of Formula (I) employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of Formula (I) employed in the pharmaceutical composition at levels lower than that required in order to achieve the desired therapeutic effect and gradually increase the dosage until the desired effect is achieved.

In general, a suitable daily dose of a compound of Formula (I) will be that amount of the compound which is the lowest dose effective to produce a therapeutic effect. Such an effective dose will generally depend upon the factors described above. Generally, oral, intravenous, intracerebroventricular and subcutaneous doses of the compounds of Formula (I) for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of Formula (I) to be administered alone, it is preferable to administer the compound as a pharmaceutical formulation (composition).

The above other therapeutic agents, when employed in combination with the compounds of Formula (I), may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Fourth Edition, Wiley and Sons, 207).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

General routes to compounds described in the invention are illustrated in Schemes 1-9, where the $R_4$, $R_5$, $R_6$, Z, and A substituents are defined previously in the text or a functional group that can be converted to the desired final substituent. The substituent L is a leaving group such as a halide (preferably I, Br, or Cl) or a sulfonate. The substituent M is a suitable coupling partner, such as boronic acid, boronic ester or stannane. The substituent R is a carboxylic acid protecting group such as tert-butyl, methyl, ethyl, or benzyl. As shown in Scheme 1, a general procedure for the preparation of compounds of the invention involves starting with a suitably substituted heterocycle 1. The leaving group, L, of 1 can be converted a suitable coupling partner, M, using conditions well known to one of ordinary skill in the art or methods described herein to afford intermediate 2. Where M is a boronic acid or boronate ester, 2 can be united with a suitably substituted heterocycle 3 in a Suzuki-Miyaura coupling reaction using a suitable palladium catalyst (e.g. Pd(PPh$_3$)$_4$ or [1,1'-bis(diphenylphosphino)ferrocene] dichloropalladium(II) or [1,1'-bis(di-tert-butylphosphino) ferrocene] dichloropalladium(II)) in the presence of a suitable base (e.g. cesium carbonate, potassium phosphate, or sodium bicarbonate) to give 4. Where M is a stannane, 2 can be united with a suitably substituted heterocycle 3 in a Stille coupling reaction using a suitable catalyst system (e.g. Pd(PPh$_3$)$_4$ or bis(triphenylphosphine)dichloropalladium(II)/CuI) to give 4. When R=tert-butyl, intermediate 4 can be converted to 5 via treatment with a protic acid such as benzenesulfonic acid. In some cases, depending upon the selection of the acid protecting group R, 4 can be converted to 5 by treatment with a base (e.g. K$_2$CO$_3$, K$_3$PO$_4$, or LiHMDS). In some cases, intermediate 4 may spontaneously cyclize to 5 under the Suzuki-Miyaura coupling or Stille coupling conditions employed to prepare it.

In some cases, it may be advantageous to couple heterocycle A earlier in the synthetic sequence. In such cases, the leaving group, L, of 6 can be converted to a suitable coupling partner, M, using conditions well known to one of ordinary skill in the art or methods described herein to afford intermediate 7. Where M is a boronic acid or boronate ester, 7 can be united with a suitably substituted heterocycle 3 in a Suzuki-Miyaura coupling reaction using a suitable palladium catalyst (e.g. Pd(PPh$_3$)$_4$ or [1,1'-bis(diphenylphosphino)ferrocene]dichloropalladium(II) or [1,1'-bis(di-tert-butylphosphino)ferrocene]dichloropalladium(II)) in the presence of a suitable base (e.g. cesium carbonate, potassium phosphate, or sodium bicarbonate) to give 8. Where M is a stannane, 7 can be united with a suitably substituted heterocycle 3 in a Stille coupling reaction using a suitable catalyst system (e.g. Pd(PPh$_3$)$_4$ or bis(triphenylphosphine) dichloropalladium(II)/CuI) to give 8. The benzylic position can be brominated through the action of NBS in the presence of a radical initiator such as AIBN, benzoyl peroxide, or light to afford bromide 9. Bromide 9 can be condensed with 3-aminopiperidine-2,6-dione (10) in the presence of a base (e.g. diisopropylethylamine or triethylamine) to afford 11.

SCHEME 1

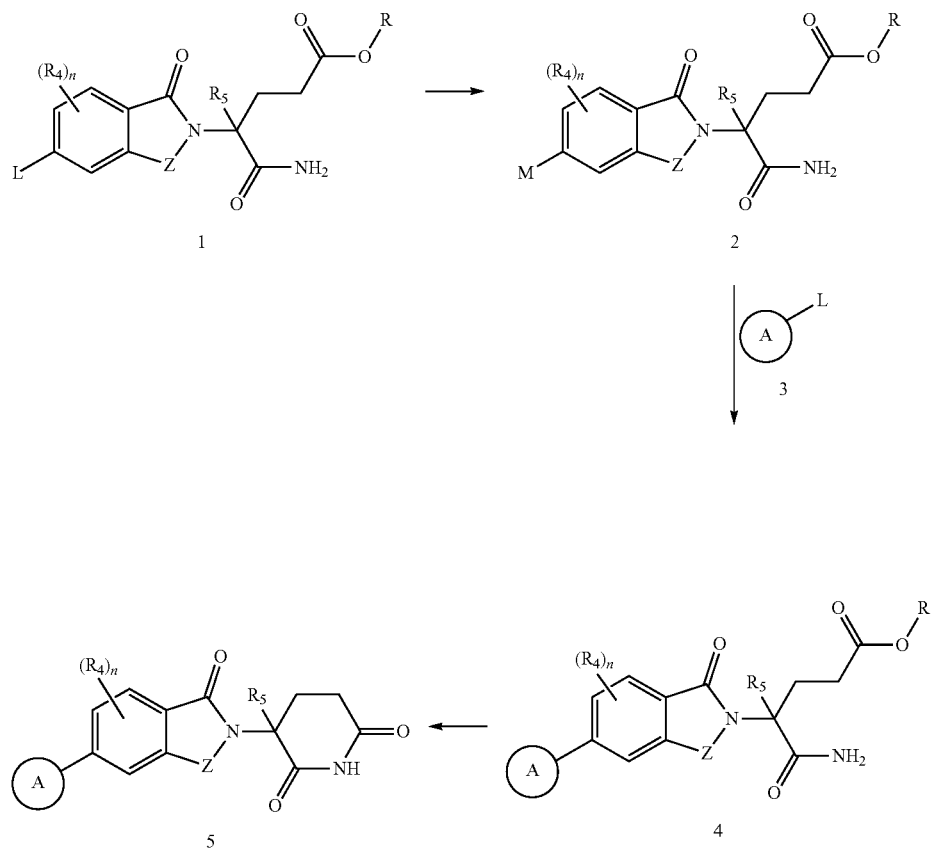

SCHEME 2

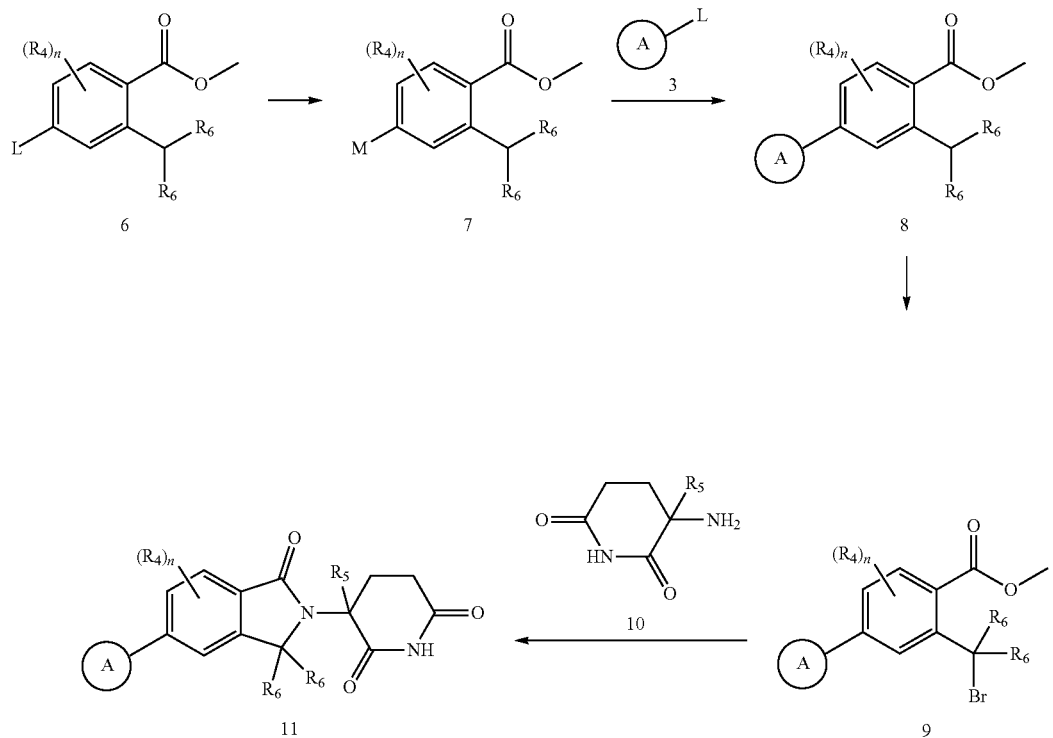

Alternately, bromide 9 (Scheme 2) or compound 12 (where L is a leaving group such as a halide or a sulfonate, Scheme 3) can be condensed with 13 (where R is a carboxylic acid protecting group such as tert-butyl, methyl, ethyl, or benzyl) in the presence of a base (e.g. diisopropylethylamine or triethylamine) to afford intermediate 14 as shown in Scheme 3.

SCHEME 3

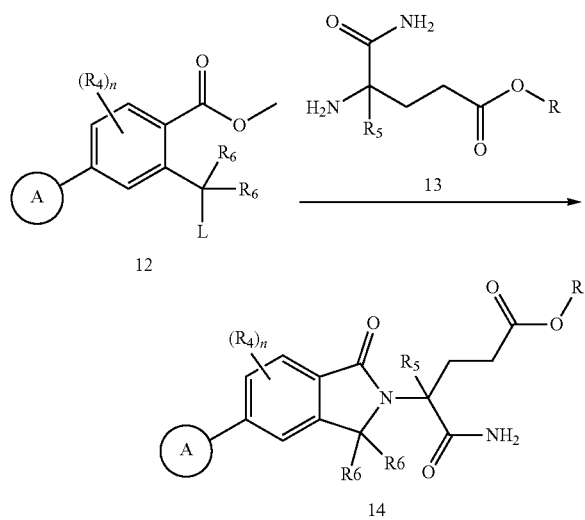

Depending on the specific selection of acid protecting group R in intermediate 4, different conditions may be required to convert it into compound 5 (Scheme 4). For instance where R=methyl, ethyl, or benzyl, base-induced cyclization of 4 may be preferred for the direct conversion 4 to 5 using a suitable base (e.g. LiHMDS) in a suitable solvent (e.g. tetrahydrofuran). Where R=tert-butyl, acid-induced cyclization of 4 may be preferred for direct conversion of 4 to 5 using a suitable acid (e.g. benzenesulfonic acid) in a suitable solvent (e.g. acetonitrile). In some cases, it may be preferable to use a twostep procedure, first liberating free carboxylic acid 15 using conditions which are appropriate to the specific acid protecting group R. Such methods are well known to one of ordinary skill in the art of organic synthesis. For instance where R=tert-butyl, acid hydrolysis using a suitable acid (e.g. trifluoroacetic acid or hydrochloric acid) may be preferred. Where R=methyl, ethyl, or benzyl, basic hydrolysis using a suitable base (e.g. LiOH) may be preferred. In other cases, where R=benzyl, it may be advantageous to deprotect by the action of palladium-catalyzed hydrogenolysis. Once liberated, the carboxylic acid of 15 can be activated toward intramolecular attack by the pendant primary amide by the action of thionyl chloride/dimethylformamide or carbonyldiimidazole/dimethylaminopyridine to afford 5.

SCHEME 4

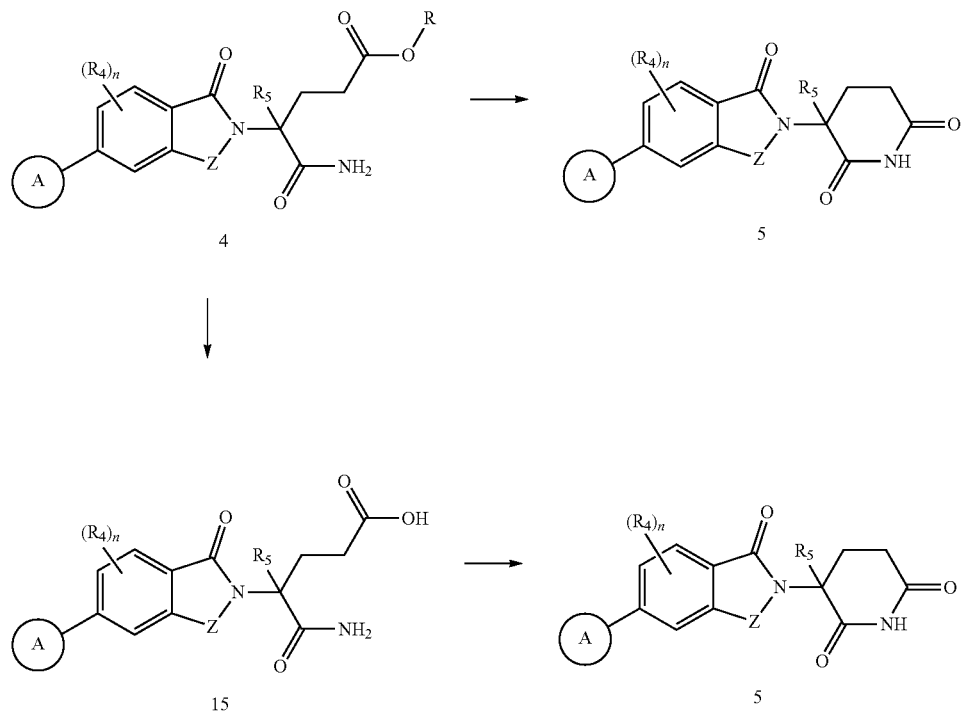

As shown in Scheme 1, heterocycles substituted with a suitable leaving group L (such as compound 1) are useful intermediates in the synthesis of Formula (I) compounds. In some cases, they may be prepared as outlined in Scheme 5 where L is a leaving group such as halide. To begin, the benzylic position of intermediate 6 can be brominated through the action of NBS in the presence of a radical initiator such as AIBN, benzoyl peroxide, or light to afford bromide 16. Bromide 16 can be condensed with 3-aminopiperidine-2,6-dione (10) in the presence of a base (e.g. diisopropylethylamine or triethylamine) to afford 17. Alternately, bromide 16 can be condensed with 13 in the presence of a base (e.g. diisopropylethylamine or triethylamine) to afford 18.

SCHEME 5

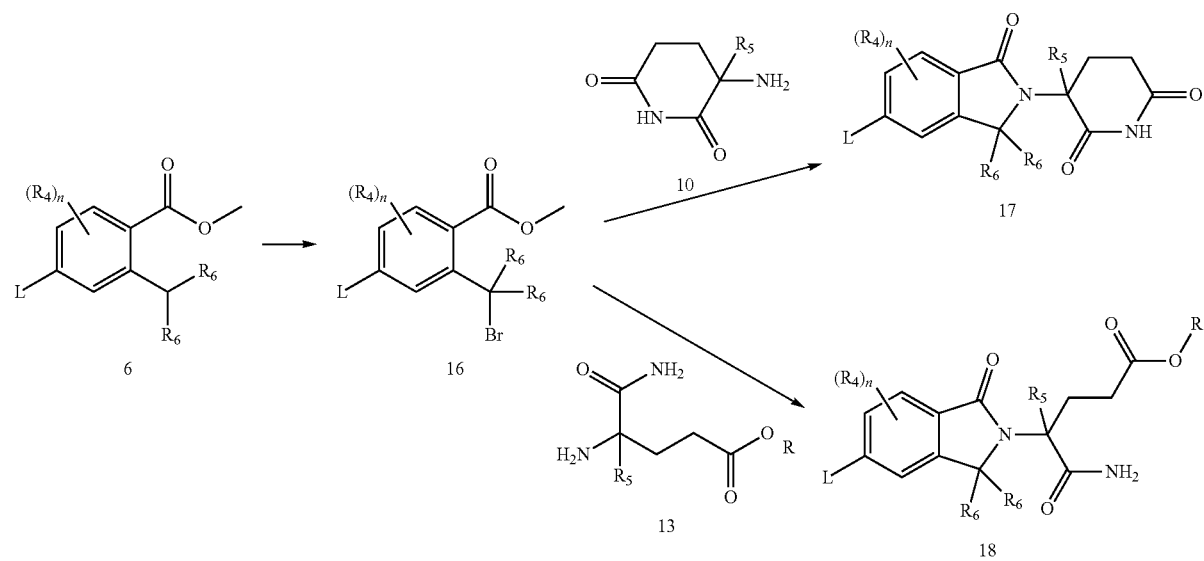

An alternate sequence to afford heterocycles substituted with a suitable leaving group L, is outlined in Scheme 6. To begin, dehydration of 19 can be accomplished by the action of acetic anhydride to afford anhydride 20. In some cases, this process can be facilitated by the addition of pyridine. Anhydride 20 can be condensed with 3-aminopiperidine-2,6-dione (10) using a combination of acetic acid and potassium acetate to afford 21. Alternately, anhydride 20 can be condensed with 13 using a combination of acetic acid and potassium acetate to afford 22.

cycle 3 in a Suzuki-Miyaura coupling reaction using a suitable palladium catalyst (e.g. $Pd(PPh_3)_4$ or [1,1'-bis(diphenylphosphino)ferrocene]dichloropalladium(II) or [1,1'-bis(di-tert-butylphosphino)ferrocene]dichloropalladium(II)) in the presence of a suitable base (e.g. cesium carbonate, potassium phosphate, or sodium bicarbonate) to give 24. Where M is a stannane, 23 can be united with a suitably substituted heterocycle 3 in a Stille coupling reaction using a suitable catalyst system (e.g. $Pd(PPh_3)_4$ or bis(triphenylphosphine)dichloropalladium(II)/CuI) to give 24. Dehy-

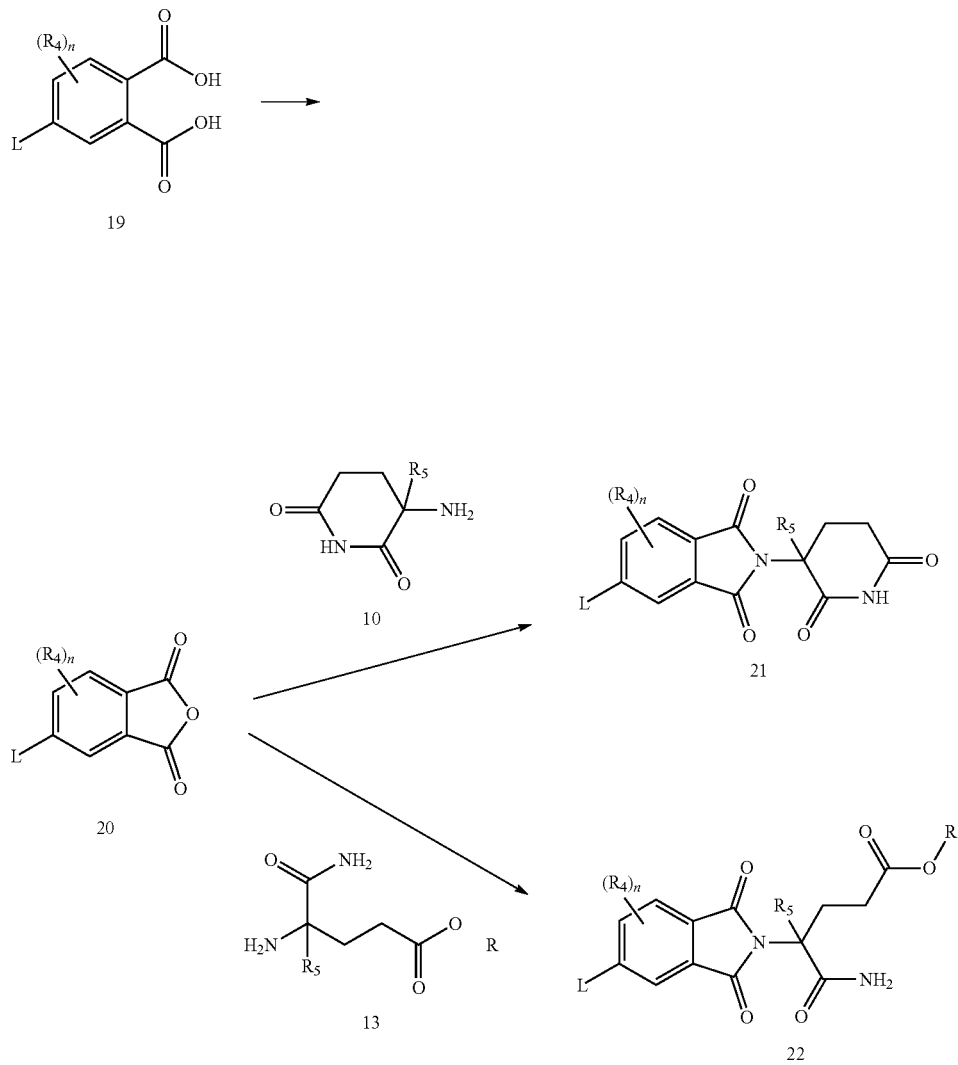

SCHEME 6

In some cases, it may be advantageous to couple heterocycle A earlier in the synthetic sequence. In such cases, the leaving group, L, of 19 can be converted to a suitable coupling partner, M, using conditions well known to one of ordinary skill in the art or methods described herein to afford intermediate 23. Where M is a boronic acid or boronate ester, 23 can be united with a suitably substituted heterodration of 24 can be accomplished by the action of acetic anhydride to afford anhydride 25. In some cases, this process can be facilitated by the addition of pyridine. Anhydride 25 can be condensed with 3-aminopiperidine-2,6-dione (10) using a combination of acetic acid and potassium acetate to afford 26 as shown in Scheme 7.

SCHEME 7

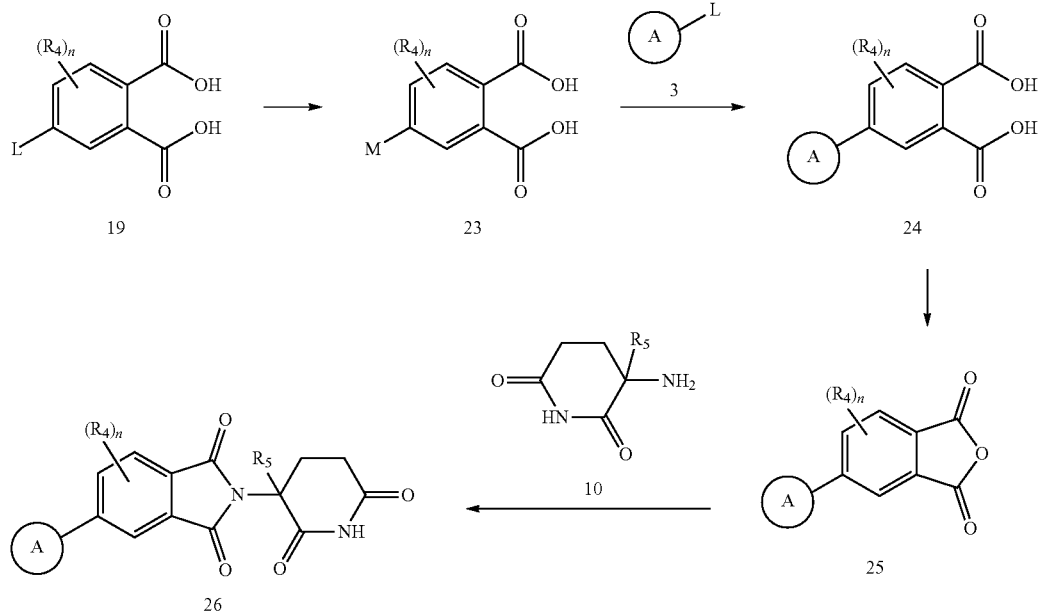

As outlined in the previous schemes, it is often convenient and advantageous to convert the leaving group L of 27 into a suitable coupling partner M in 28 (such as a boronic acid, boronic ester or stannane). This can, in turn, be coupled to substituted heterocycle 3 to give 5. In some cases it may be preferable reverse the coupling partners, to couple 27 to substituted heterocycle 29 to give 5 directly. Where the coupling partner M of 29 is a boronic acid or a boronic ester, a copper-assisted Suzuki-Miyaura may be preferred (see Crowley, et. al. Tetrahedron Letters, 2011, 5055). This is outlined in Scheme 8. Similarly, intermediate 1 (Scheme 9) can be coupled to heterocycle 29 to yield intermediate 4 directly. Further elaboration by the methods described above can result in additional Formula (I) compounds.

SCHEME 8

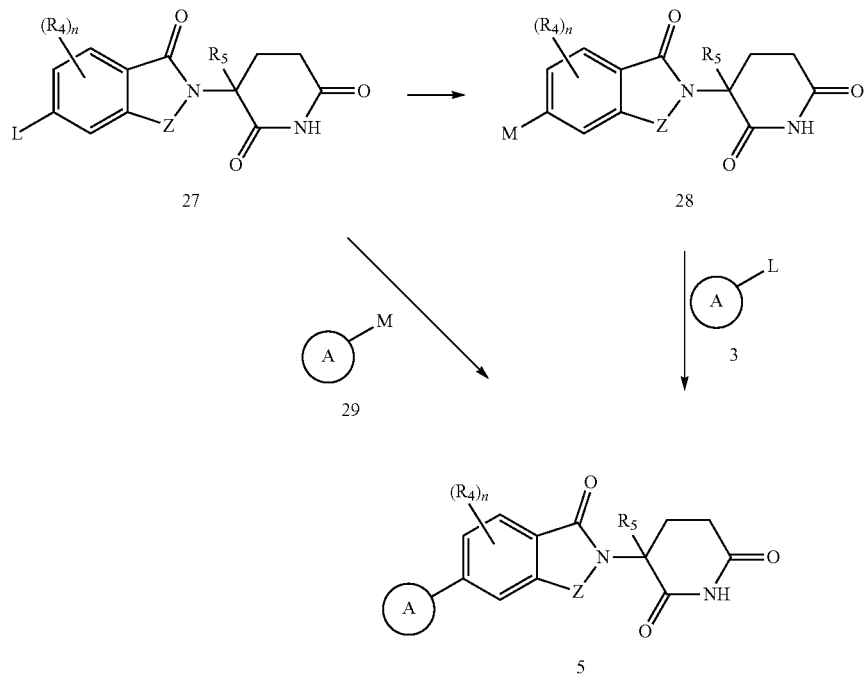

SCHEME 9

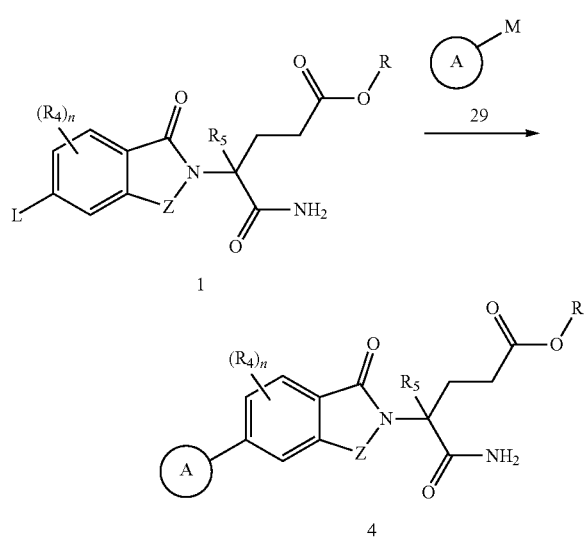

EXAMPLES

The following examples illustrate the particular embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example. In some instances alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well-known bioisosteric replacements known in the art, for example, replacement of a carboxylic acid group with a tetrazole or a phosphate moiety.

ABBREVIATIONS

AIBN azobisiosbutyronitrile
Boc tert-butoxycarbonyl
DCM dichloromethane
DIEA N,N-diisopropylethylamine
DMF N,N-dimethylformamide
DMSO dimethyl sulfoxide
ESI electrospray ionization
EtOAc ethyl acetate
EtOH ethanol
h hour(s)
Hex hexanes
HPLC high performance liquid chromatography
Hunig's base N,N-diisopropylethylamine
LCMS liquid chromatography mass spectrometry
min minute(s)
mL milliliter(s)
MS mass spectrometry
NBS N-bromosuccinimide
Pd(dppf)Cl$_2$ [1,1'-bis(diphenylphosphino)ferrocene]dichloropalladium(II)
Pd(dtbpf)Cl$_2$ [1,1'-bis(di-tert-butylphosphino)ferrocene]dichloropalladium(II)
TEA triethylamine
Analytical HPLC Conditions
Method A: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).
Method B: Column: Waters)(Bridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm).

Example 1

3-(5-{4-[(Dimethylamino)methyl]pyridin-2-yl}-1-oxo-2,3-dihydro-1H-isoindol-2-yl) piperidine-2,6-dione (1)

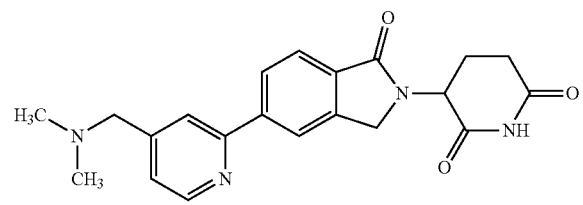

Step 1: tert-Butyl (S)-5-amino-4-(5-bromo-1-oxoisoindolin-2-yl)-5-oxopentanoate

To a suspension of tert-butyl (S)-4,5-diamino-5-oxopentanoate hydrochloride (14.46 g, 60.6 mmol) in acetonitrile (231 mL) at 0° C. was added DIEA (20.2 mL, 115 mmol). After stirring for 15 min, the reaction mixture was treated with methyl 4-bromo-2-(bromomethyl)benzoate (22 g, 57.7 mmol) as a solid in several portions over 5 min. The reaction mixture was stirred at 0° C. for 30 min and then at room temperature overnight. The reaction mixture was warmed to 60° C. in an oil bath under a reflux condenser and held at that temperature overnight. The reaction mixture was cooled to room temperature with stirring. After cooling to room temperature, a precipitate formed. The flask was placed in a 0° C. bath with stirring. After 30 min, the solid was collected by filtration, rinsed with a minimum of cold acetonitrile, and air dried to give 20.13 g (88% yield) as a white solid. Chiral analytical HPLC analysis indicated that the material was >98% ee. MS (ES): m/z=397.1 [M+H]$^+$. $^1$H NMR (400 MHz, CDCl$_3$) δ 7.76-7.71 (m, 1H), 7.68-7.62 (m, 2H), 6.22

(br s, 1H), 5.31 (br s, 1H), 4.91 (dd, J=8.7, 6.3 Hz, 1H), 4.62-4.53 (m, 1H), 4.51-4.40 (m, 1H), 2.47-2.10 (m, 4H), 1.44 (s, 9H).

Step 2: tert-Butyl (S)-5-amino-5-oxo-4-(1-oxo-5-(4,4,5,5-tetramethyl-1,3,2-dioxaborolan-2-yl)isoindolin-2-yl)pentanoate A dry flask was charged with tert-butyl (S)-5-amino-4-(5-bromo-1-oxoisoindolin-2-yl)-5-oxopentanoate (10.0 g, 25.2 mmol), 4,4,4',4',5,5,5',5'-octamethyl-2,2'-bi(1,3,2-dioxaborolane) (7.67 g, 30.2 mmol), and potassium acetate (7.41 g, 76 mmol) and flushed with nitrogen. The solids were suspended in dioxane (100 mL) and degassed with a stream of nitrogen for 5 min with stirring. The reaction mixture was treated with [1,1'-bis(diphenylphosphino)ferrocene]dichloropalladium(II) (0.737 g, 1.007 mmol), degassed for 5 min, sealed, and heated to 60° C. for 18 h. The reaction mixture was diluted with EtOAc, filtered through a plug of celite, and rinsed with additional EtOAc. The filtrate was concentrated and purified using a 220 gram silica gel column by ISCO (0%→20% B/DCM, where B=15% EtOH/EtOAc+0.1% TEA) to give 9.9 g (89% yield) as a white solid. MS (ES): m/z=445.3 [M+H]$^+$. $^1$H NMR (400 MHz, CDCl$_3$) δ 7.99-7.90 (m, 2H), 7.88-7.83 (m, 1H), 6.32 (br s, 1H), 5.36 (br s, 1H), 4.97-4.88 (m, 1H), 4.58-4.41 (m, 2H), 2.48-2.13 (m, 4H), 1.44 (s, 9H), 1.39 (s, 12H).

Step 3: tert-Butyl (S)-5-amino-4-(5-(4-(hydroxymethyl)pyridin-2-yl)-1-oxoisoindolin-2-yl)-5-oxopentanoate A flask was charged with (2-chloropyridin-4-yl)methanol (1.00 g, 6.97 mmol), tert-butyl (S)-5-amino-5-oxo-4-(1-oxo-5-(4,4,5,5-tetramethyl-1,3,2-dioxaborolan-2-yl)isoindolin-2-yl)pentanoate (3.87 g, 8.71 mmol), Pd(dtbpf)Cl$_2$ (0.136 g, 0.209 mmol), dioxane (50 mL) and aqueous K$_3$PO$_4$ (3M, 11.61 mL, 34.8 mmol). The vessel was sealed and the air was replaced with nitrogen. The reaction was heated overnight at 70° C. The reaction was cooled to room temperature, diluted with EtOAc, washed with brine, and the layers separated. The organics were dried over sodium sulfate, filtered, and concentrated. The resulting residue was purified by flash chromatography using a 120 gram ISCO column and eluting with 0-100% B/DCM [where B=15% EtOH/EtOAc+0.1% triethylamine] to give 1.38 g (47%). MS (ES): m/z=426.4 [M+H]$^+$.

Step 4: 3-(5-(4-(Chloromethyl)pyridin-2-yl)-1-oxoisoindolin-2-yl)piperidine-2,6-dione hydrochloride To a solution of tert-butyl (S)-5-amino-4-(5-(4-(hydroxymethyl)pyridin-2-yl)-1-oxoisoindolin-2-yl)-5-oxopentanoate (1.00 g, 2.35 mmol) in DCM (15 mL) at 0° C. was added thionyl chloride (0.511 mL, 7.05 mmol) dropwise. After 5 min, the ice-bath was removed and the reaction allowed to warm to room temperature. After 30 min, the reaction was concentrated. The resulting residue was dissolved in acetonitrile (15 mL). To this was added benzenesulfonic acid (0.818 g, 5.17 mmol). The reaction was heated via microwave for 30 min at 130° C. The reaction was concentrated to dryness. To this was added 20 mL of 2M HCl in diethylether and the resulting mixture stirred for 30 min. The mother liquor was removed by decantation and discarded. The remaining solids were dried under vacuum to obtain 708 mg (81%) as the hydrochloride salt. MS (ES): m/z=370.2 [M+H]$^+$.

Step 5: 3-(5-{4-[(Dimethylamino)methyl]pyridin-2-yl}-1-oxo-2,3-dihydro-1H-isoindol-2-yl)piperidine-2,6-dione A vial was charged with 3-(5-(4-(chloromethyl)pyridin-2-yl)-1-oxoisoindolin-2-yl)piperidine-2,6-dione hydrochloride (71 mg, 0.175 mmol), dimethylamine hydrochloride (42.8 mg, 0.524 mmol), and DMF (1 mL). To this was added N-ethyl-N-isopropylpropan-2-amine (0.304 mL, 1.748 mmol). The reaction was heated for 3 h at 70° C. The reaction was cooled to room temperature and treated with acetic acid (0.5 mL). The product was purified by preparative HPLC to give 40 mg (52%). $^1$H NMR (400 MHz, DMSO-d6) δ 11.37-10.73 (m, 1H), 8.66 (d, J=5.0 Hz, 1H), 8.33 (s, 1H), 8.25 (dd, J=8.0, 1.4 Hz, 1H), 7.98 (s, 1H), 7.84 (d, J=8.1 Hz, 1H), 7.36 (dd, J=5.3, 1.0 Hz, 1H), 5.21-5.11 (m, 1H), 4.61-4.39 (m, 2H), 3.02-2.87 (m, 1H), 2.71-2.59 (m, 1H), 2.53 (m, 2H), 2.47-2.38 (m, 1H), 2.22 (s, 6H), 2.12-2.00 (m, 1H). LCMS (Method B): retention time 1.09 min, [M+H]$^+$ 379.3.

Examples 2-143

The compounds in Table 1 were prepared according to the procedures described for Example 1, replacing dimethylamine with the appropriate primary or secondary amine:

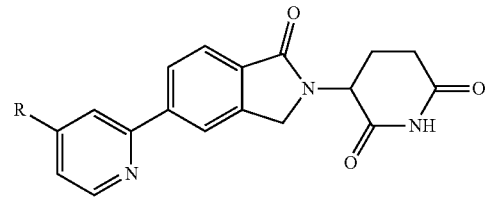

TABLE 1

| Ex. No. | R | LC/MS [M + H]$^+$ | Retention Time (min) | HPLC Method |
|---|---|---|---|---|
| 2 | ![benzyl-NH-CH2-] | 441.3 | 0.77 | A |
| 3 | ![H3C-CH2-N(CH3)-CH2-] | 407.1 | 0.98 | A |

TABLE 1-continued

| Ex. No. | R | LC/MS [M + H]+ | Retention Time (min) | HPLC Method |
|---|---|---|---|---|
| 4 | H3C-N(CH3)-CH2- | 393.1 | 0.89 | A |
| 5 | (CH3)2CH-N(CH3)-CH2- | 407.3 | 1.30 | B |
| 6 | piperidin-1-yl-CH2- | 419.3 | 0.90 | A |
| 7 | H3CO-CH2CH2-N(CH3)-CH2- | 423.3 | 0.89 | A |
| 8 | pyrrolidin-1-yl-CH2- | 405.1 | 1.00 | A |
| 9 | H3C-CH2CH2CH2-N(CH3)-CH2- | 421.3 | 1.57 | B |
| 10 | cyclopropyl-CH2-N(CH2CH2CH3)-CH2- | 447.0 | 1.89 | B |
| 11 | 3-(2-oxo-2,3-dihydro-1H-benzimidazol-1-yl)piperidin-1-yl-CH2- | 551.4 | 1.41 | B |
| 12 | 4-(benzo[d][1,3]dioxol-5-ylmethyl)piperazin-1-yl-CH2- | 554.2 | 1.55 | B |
| 13 | N,N-diethylcarbamoyl-piperidin-1-yl-CH2- | 518.2 | 1.42 | B |
| 14 | 4-methylpiperidin-1-yl-CH2- | 433.1 | 1.43 | B |

TABLE 1-continued
| Ex. No. | R | LC/MS [M + H]+ | Retention Time (min) | HPLC Method |
|---|---|---|---|---|
| 15 | 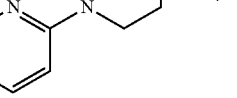 | 497.1 | 1.55 | B |
| 16 | 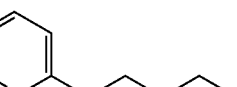 | 470.2 | 1.27 | B |
| 17 | 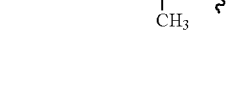 | 502.2 | 0.89 | A |
| 18 | 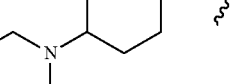 | 498.0 | 1.48 | B |
| 19 | 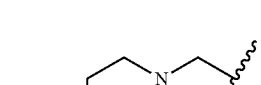 | 483.4 | 1.13 | A |
| 20 | 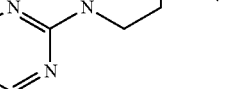 | 419.4 | 1.18 | B |
| 21 | 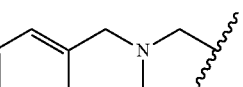 | 436.2 | 1.06 | B |
| 22 | 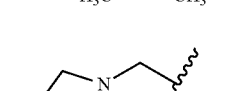 | 470.0 | 1.00 | A |
| 23 | 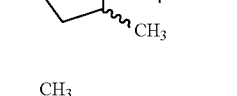 | 488.2 | 0.96 | B |

TABLE 1-continued

| Ex. No. | R | LC/MS [M + H]+ | Retention Time (min) | HPLC Method |
|---|---|---|---|---|
| 24 | (piperazine-N-C(O)-furan-2-yl) | 514.1 | 1.34 | B |
| 25 | (4-(pyridin-4-yl)piperazin-1-yl) | 497.2 | 1.12 | B |
| 26 | (4-(pyrazin-2-yl)piperazin-1-yl) | 497.9 | 1.38 | B |
| 27 | (2-methyl-4-(m-tolyl)piperazin-1-yl) | 524.0 | 2.06 | B |
| 28 | (4-acetylpiperazin-1-yl) | 462.2 | 0.91 | A |
| 29 | (N-methyl-N-(1-methylpyrrolidin-3-yl)amino) | 448.1 | 0.84 | A |
| 30 | (2-((1-methylpyrrolidin-2-yl)methyl)piperidin-1-yl) | 516.2 | 0.91 | A |
| 31 | ((S)-3-acetamidopyrrolidin-1-yl) | 462.0 | 0.91 | A |

TABLE 1-continued

| Ex. No. | R | LC/MS [M + H]⁺ | Retention Time (min) | HPLC Method |
|---|---|---|---|---|
| 32 | piperazine-N-C(O)-tetrahydrofuran-2-yl | 518.2 | 1.15 | B |
| 33 | (R)-3-(dimethylamino)pyrrolidin-1-yl | 448.1 | 1.01 | B |
| 34 | N,N-dimethyl-2-(methylamino)acetamide | 450.2 | 0.94 | A |
| 35 | 4-methylpiperazin-1-yl | 434.0 | 0.88 | A |
| 36 | 4-benzylpiperazin-1-yl | 510.2 | 1.64 | B |
| 37 | 3-oxopiperazin-1-yl | 434.1 | 0.99 | B |
| 38 | 4-benzylpiperidin-1-yl | 508.9 | 1.88 | B |
| 39 | 3,4-dihydroisoquinolin-2(1H)-yl | 466.9 | 1.07 | A |
| 40 | 4-(dimethylamino)piperidin-1-yl | 462.1 | 1.06 | B |
| 41 | 4-carbamoylpiperidin-1-yl | 462.0 | 0.89 | A |

TABLE 1-continued

| Ex. No. | R | LC/MS [M + H]+ | Retention Time (min) | HPLC Method |
|---|---|---|---|---|
| 42 | 1-benzhydrylpiperazin-4-yl-ethyl | 585.9 | 2.20 | B |
| 43 | 4-methyl-1,4-diazepan-1-yl-ethyl | 448.1 | 0.82 | A |
| 44 | 4-isopropylpiperazin-1-yl-ethyl | 462.1 | 1.11 | B |
| 45 | (3)-3-(dimethylamino)pyrrolidin-1-yl-ethyl | 448.3 | 0.82 | A |
| 46 | 2-methylazetidin-1-yl-ethyl | 405.2 | 1.12 | B |
| 47 | 3-methylazetidin-1-yl-ethyl | 405.3 | 1.11 | B |
| 48 | azepan-1-yl-ethyl | 433.3 | 1.40 | B |
| 49 | N-methyl-N-(1-methylpyrrolidin-3-yl)amino-ethyl | 448.2 | 1.02 | B |
| 50 | N,N-diethylamino-ethyl | 407.3 | 0.95 | A |
| 51 | 3,3-dimethylazetidin-1-yl-ethyl | 419.3 | 1.18 | B |

TABLE 1-continued
| Ex. No. | R | LC/MS [M + H]+ | Retention Time (min) | HPLC Method |
|---|---|---|---|---|
| 52 | 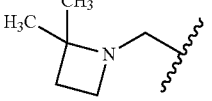 | 419.3 | 1.04 | B |
| 53 | 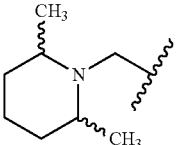 | 447.2 | 1.39 | B |
| 54 | 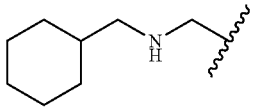 [SMILES: *CNCC1CCCCC1] | 447.0 | 1.49 | B |
| 55 | 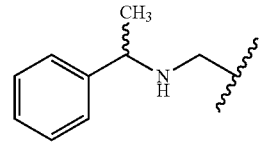 [SMILES: *CNC(C)c1ccccc1] | 455.2 | 1.53 | B |
| 56 | 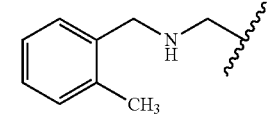 [SMILES: *CNCc1ccccc1C] | 455.2 | 1.54 | B |
| 57 | 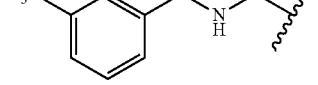 | 455.2 | 1.49 | B |
| 58 | 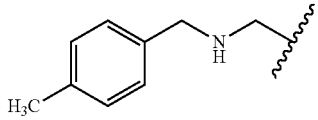 [SMILES: *CNCc1ccc(C)cc1] | 455.1 | 1.48 | B |
| 59 | 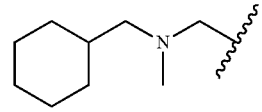 [SMILES: *CN(C)CC1CCCCC1] | 461.0 | 2.15 | B |
| 60 | 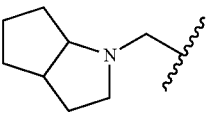 [SMILES: *CN1CCC2CCCC21] | 445.1 | 1.49 | B |
| 61 | 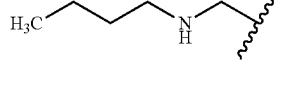 | 407.2 | 1.18 | B |
| 62 | 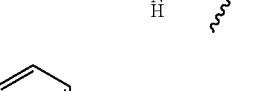 | 393.1 | 0.99 | B |
| 63 | 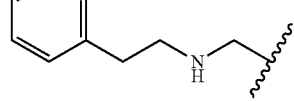 | 455.2 | 1.41 | B |

TABLE 1-continued

| Ex. No. | R | LC/MS [M + H]+ | Retention Time (min) | HPLC Method |
|---|---|---|---|---|
| 64 | cyclopropyl-CH2-NH-CH2-⁓ | 405.1 | 1.00 | B |
| 65 | (CH3)3C-CH2-NH-CH2-⁓ | 421.1 | 1.28 | B |
| 66 | (tetrahydrofuran-2-yl)-CH2-NH-CH2-⁓ | 435.1 | 0.94 | A |
| 67 | 4-MeO-C6H4-CH2-NH-CH2-⁓ | 471.1 | 1.03 | A |
| 68 | CH3O-CH2CH2-NH-CH2-⁓ | 409.1 | 0.95 | B |
| 69 | (2-methylpyrrolidin-1-yl)-CH2-⁓ | 419.1 | 1.29 | B |
| 70 | (3-methylpyrrolidin-1-yl)-CH2-⁓ | 419.1 | 1.32 | B |
| 71 | (2-methylpiperidin-1-yl)-CH2-⁓ | 432.9 | 1.57 | B |
| 72 | (3-methylpyrrolidin-1-yl)-CH2-⁓ | 419.2 | 1.11 | A |
| 73 | (3-methylpiperidin-1-yl)-CH2-⁓ | 432.9 | 1.60 | B |
| 74 | (2-methylpiperidin-1-yl)-CH2-⁓ | 433.1 | 1.50 | B |

TABLE 1-continued

| Ex. No. | R | LC/MS [M + H]+ | Retention Time (min) | HPLC Method |
|---|---|---|---|---|
| 75 | | 433.1 | 1.59 | B |
| 76 | | 467.1 | 1.00 | A |
| 77 | | 445.3 | 1.07 | A |
| 78 | | 460.2 | 0.91 | A |
| 79 | | 433.3 | 0.93 | A |
| 80 | | 449.1 | 0.97 | A |
| 81 | | 447.2 | 1.08 | A |
| 82 | | 447.2 | 1.70 | B |
| 83 | | 467.2 | 1.12 | A |

TABLE 1-continued

| Ex. No. | R | LC/MS [M + H]+ | Retention Time (min) | HPLC Method |
|---|---|---|---|---|
| 84 | (trans-2-phenylcyclopentyl)amino | 494.9 | 1.22 | A |
| 85 | (3,3-dimethylpiperidin-1-yl) | 447.3 | 1.05 | A |
| 86 | cyclopentylamino | 419.2 | 1.21 | B |
| 87 | cyclohexylamino | 433.3 | 1.16 | B |
| 88 | (2-morpholinoethyl)amino | 464.2 | 1.12 | B |
| 89 | tert-butylamino | 407.1 | 1.20 | B |
| 90 | (2,2-diphenylethyl)amino | 531.2 | 1.36 | A |
| 91 | (2-acetamidoethyl)amino | 435.9 | 1.04 | B |
| 92 | (2-hydroxyethyl)amino | 395.3 | 0.82 | A |
| 93 | (2-(2-chlorophenyl)ethyl)amino | 489.3 | 1.15 | A |

TABLE 1-continued
| Ex. No. | R | LC/MS [M + H]+ | Retention Time (min) | HPLC Method |
|---|---|---|---|---|
| 94 | 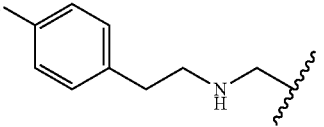 | 489.3 | 1.58 | B |
| 95 | 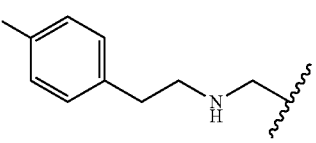 | 485.1 | 1.07 | A |
| 96 | 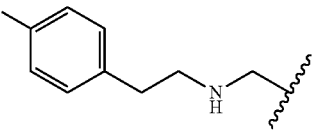 | 471.1 | 1.19 | B |
| 97 | 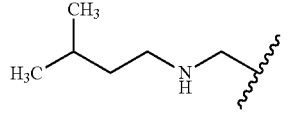 | 420.9 | 1.40 | B |
| 98 | 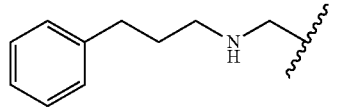 [SMILES: *CNCCCc1ccccc1] | 469.4 | 1.14 | A |
| 99 | 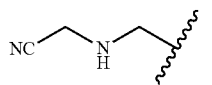 [SMILES: *CNCC#N] | 389.9 | 0.97 | A |
| 100 | 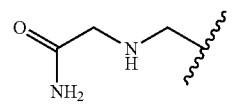 [SMILES: *CNCC(N)=O] | 408.1 | 1.04 | B |
| 101 | 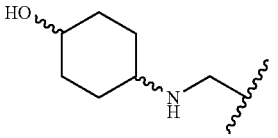 [SMILES: *CNC1CCC(O)CC1] | 449.2 | 1.01 | B |
| 102 | 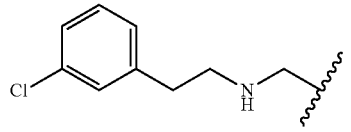 [SMILES: *CNCCc1cccc(Cl)c1] | 489.2 | 1.24 | A |
| 103 | 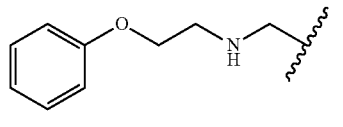 [SMILES: *CNCCOc1ccccc1] | 471.3 | 1.55 | B |
| 104 | 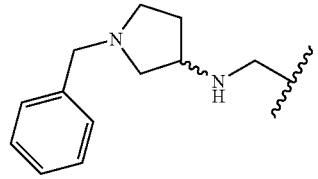 [SMILES: *CNC1CCN(Cc2ccccc2)C1] | 510.2 | 0.96 | A |

TABLE 1-continued

| Ex. No. | R | LC/MS [M + H]+ | Retention Time (min) | HPLC Method |
|---|---|---|---|---|
| 105 | H2N-C(O)-CH2CH2-NH- | 422.1 | 1.01 | B |
| 106 | benzothiazol-2-yl-CH2CH2-NH- | 512.1 | 1.16 | A |
| 107 | (CH3)2N-cyclohexyl-NH- | 476.1 | 0.90 | B |
| 108 | cyclobutyl-NH- | 405.1 | 1.03 | A |
| 109 | cyclopropyl-NH- | 391.1 | 1.28 | B |
| 110 | 2-phenylthiazol-4-yl-CH2-NH- | 524.1 | 1.59 | B |
| 111 | trans-2-phenylcyclopropyl-NH- | 467.1 | 1.65 | B |
| 112 | H3CO-C(O)-CH2CH2-NH- | 437.3 | 0.88 | A |
| 113 | imidazol-1-yl-(CH2)3-NH- | 459.1 | 0.83 | A |
| 114 | morpholin-4-yl-(CH2)3-NH- | 478.2 | 1.11 | B |
| 115 | 2-oxopyrrolidin-1-yl-(CH2)3-NH- | 476.2 | 1.01 | A |

TABLE 1-continued

| Ex. No. | R | LC/MS [M + H]+ | Retention Time (min) | HPLC Method |
|---|---|---|---|---|
| 116 | H₃C−NH−⁓ | 379.1 | 1.06 | B |
| 117 | 2,2-dimethylpyrrolidin-1-yl-CH₂⁓ | 432.9 | 1.50 | B |
| 118 | 3,3-dimethylpyrrolidin-1-yl-CH₂⁓ | 433.2 | 1.59 | B |
| 119 | 2,5-dimethylpyrrolidin-1-yl-CH₂⁓ | 433.1 | 1.50 | B |
| 120 | 2,6-dimethylpiperidin-1-yl-CH₂⁓ | 447.1 | 0.96 | A |
| 121 | 4-(4-aminophenyl)-4-methylpiperidin-1-yl-CH₂⁓ | 524.3 | 0.90 | A |
| 122 | (R or S)-PhCH(CH₃)NH-CH₂⁓ | 455.2 | 1.11 | A |
| 123 | (S or R)-PhCH(CH₃)NH-CH₂⁓ | 455.1 | 1.10 | A |
| 124 | 1-hydroxycyclohexyl-CH₂-NH-CH₂⁓ | 463.4 | 1.04 | A |
| 125 | (2-methylpyrrolidin-1-yl)-CH₂⁓ | 419.3 | 1.19 | B |

TABLE 1-continued

| Ex. No. | R | LC/MS [M + H]+ | Retention Time (min) | HPLC Method |
|---|---|---|---|---|
| 126 | (2-methyltetrahydropyran-4-yl)aminomethyl | 449.2 | 1.20 | B |
| 127 | 6-azaspiro[2.5]octan-6-ylmethyl | 444.9 | 1.09 | A |
| 128 | 4-hydroxybutylaminomethyl | 423.0 | 0.92 | A |
| 129 | (oxetan-2-ylmethyl)aminomethyl | 421.2 | 1.00 | A |
| 130 | 3-isopropoxyazetidin-1-ylmethyl | 449.2 | 1.04 | A |
| 131 | (1S)-3-hydroxy-1-phenylpropylaminomethyl | 484.9 | 1.42 | B |
| 132 | 4-(p-tolylsulfonyl)piperidin-1-ylmethyl | 573.4 | 1.72 | B |
| 133 | (2S)-2-phenylpyrrolidin-1-ylmethyl | 480.9 | 1.14 | A |
| 134 | (2R)-2-phenylpyrrolidin-1-ylmethyl | 481.2 | 1.97 | B |

TABLE 1-continued

| Ex. No. | R | LC/MS [M + H]+ | Retention Time (min) | HPLC Method |
|---|---|---|---|---|
| 135 | (S)-3-phenylpiperidinyl-ethyl | 494.9 | 1.35 | A |
| 136 | (S)-N-methyl-N-(1-phenylethyl)amino-ethyl | 469.2 | 1.14 | A |
| 137 | (R)-N-methyl-N-(1-phenylethyl)amino-ethyl | 469.1 | 1.08 | A |
| 138 | (S)-3-phenylpyrrolidinyl-ethyl | 481.2 | 1.73 | B |
| 139 | (R)-3-phenylpyrrolidinyl-ethyl | 481.3 | 1.84 | B |
| 140 | (1R,2R)-2-(methylamino)cyclohexyl-N-methylamino-ethyl | 476.1 | 1.28 | B |
| 141 | 4-phenylpiperidinyl-ethyl | 495.2 | 2.10 | B |

TABLE 1-continued

| Ex. No. | R | LC/MS [M + H]+ | Retention Time (min) | HPLC Method |
|---|---|---|---|---|
| 142 | ![structure with H3C, CH3, phenyl, N-CH3] | 483.2 | 1.18 | A |
| 143 | ![phenyl-piperidine structure] | 495.1 | 1.97 | B |

Example 144

3-{5-[4-(Aminomethyl)pyridin-2-yl]-1-oxo-2,3-dihydro-1H-isoindol-2-yl}piperidine-2,6-dione

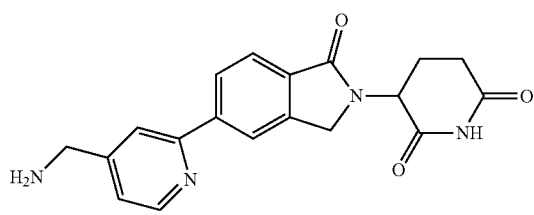

(144)

Step 1: tert-Butyl ((2-chloropyridin-4-yl)methyl)carbamate

A vial was charged with (2-chloropyridin-4-yl)methanamine, 2 HCl (300 mg, 1.39 mmol), DCM (8 mL), and di-tert-butyl dicarbonate (365 mg, 1.670 mmol). After stirring for 5 min at room temperature, triethylamine (0.775 mL, 5.57 mmol) was added and the reaction stirred for 3 h. The reaction mixture was concentrated and purified by ISCO using a 24 g silica gel gram column and eluting with 5-100% EtOAc/hexanes to give 325 mg (96%). MS (ES): m/z=243.1 [M+H]+.

Step 2: 3-{5-[4-(Aminomethyl)pyridin-2-yl]-1-oxo-2,3-dihydro-1H-isoindol-2-yl}piperidine-2,6-dione A 2 mL microwave vial was charged with tert-butyl ((2-chloropyridin-4-yl)methyl)carbamate (24 mg, 0.099 mmol), tert-butyl (S)-5-amino-5-oxo-4-(1-oxo-5-(4,4,5,5-tetramethyl-1,3,2-dioxaborolan-2-yl)isoindolin-2-yl)pentanoate (54.9 mg, 0.124 mmol), Pd(dtbpf)Cl₂ (1.933 mg, 2.97 µmol), 1,4-dioxane (1 mL) and aqueous K₃PO₄ (0.165 mL, 0.494 mmol). The reaction vial was sealed and the air replaced with nitrogen. The reaction mixture was heated via microwave for 10 min at 120° C. The reaction mixture was cooled to room temperature, diluted with EtOAc, washed with brine, dried over sodium sulfate, and concentrated. The crude was dissolved in a solution of PhSO₃H solution in MeCN (0.5 mL, 1.44 g in 40 mL) and heated via microwave for 30 min at 130° C. The reaction was concentrated to dryness. The resulting residue was purified by preparative HPLC to give 34.6 mg (30%). ¹H NMR (500 MHz, DMSO-d6) δ 11.02 (s, 1H), 8.75 (d, J=4.9 Hz, 1H), 8.42 (br s, 2H), 8.31 (s, 1H), 8.22 (br d, J=8.1 Hz, 1H), 8.14 (br s, 1H), 7.90 (d, J=8.1 Hz, 1H), 7.48 (br d, J=4.7 Hz, 1H), 5.17-5.07 (m, 1H), 4.63-4.53 (m, 1H), 4.49-4.39 (m, 1H), 4.19 (br s, 2H), 2.97-2.86 (m, 1H), 2.64 (br d, J=16.7 Hz, 1H), 2.49-2.36 (m, 1H), 2.11-2.01 (m, 1H). LCMS (Method A): retention time 0.74 min, [M+H]+ 351.1.

Example 145

3-(5-{4-[(Methylamino)methyl]pyridin-2-yl}-1-oxo-2,3-dihydro-1H-isoindol-2-yl) piperidine-2,6-dione

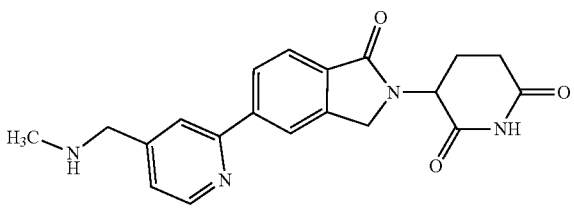

(145)

Step 1: tert-Butyl ((2-chloropyridin-4-yl)methyl)(methyl)carbamate

A vial was charged with tert-butyl ((2-chloropyridin-4-yl)methyl)carbamate (40 mg, 0.165 mmol), DMF (1.5 mL), and iodomethane (35.1 mg, 0.247 mmol). After stirring for 5 min at room temperature, sodium hydride (26.4 mg, 0.659 mmol) was added and the reaction mixture was stirred for 3 h. The reaction mixture was diluted with EtOAc and washed with brine. The mixture was concentrated and purified by preparative HPLC to give 29 mg (69%). MS (ES): m/z=257.1 [M+H]+.

Step 2: 3-(5-{4-[(Methylamino)methyl]pyridin-2-yl}-1-oxo-2,3-dihydro-1H-isoindol-2-yl)piperidine-2,6-dione A microwave vial was charged with tert-butyl ((2-chloropyridin-4-yl)methyl) (methyl)carbamate (25 mg, 0.097 mmol), tert-butyl (S)-5-amino-5-oxo-4-(1-oxo-5-(4,4,5,5- tetramethyl-1,3,2-dioxaborolan-2-yl)isoindolin-2-yl)pentanoate (54.1 mg, 0.122 mmol), Pd(dtbpf)Cl₂ (1.90 mg, 2.92 µmol), 1,4-dioxane (1 mL) and aqueous K₃PO₄ (0.162 mL, 0.487 mmol). The vial was sealed and the air was replaced with nitrogen. The reaction mixture was heated via microwave for 10 min at 120° C. The reaction mixture was diluted with EtOAc, washed with brine, dried over sodium sulfate, and concentrated. The resulting residue was dissolved in a solution of PhSO₃H solution in MeCN (0.5 mL, 1.44 g in 40 mL) and heated via microwave for 10 min at 120° C. The mixture was purified by preparative HPLC to give product (15.1 mg, 43%). ¹H NMR (500 MHz, DMSO-d6) δ 8.64 (d, J=4.9 Hz, 1H), 8.32 (s, 1H), 8.24 (d, J=7.9 Hz, 1H), 8.03 (s, 1H), 7.86 (d, J=7.9 Hz, 1H), 7.39 (br d, J=4.9 Hz, 1H), 5.14 (dd, J=13.3, 5.3 Hz, 1H), 4.61-4.51 (m, 1H), 4.49-4.39 (m, 1H), 3.80 (s, 2H), 2.98-2.87 (m, 1H), 2.69-2.60 (m, 1H), 2.49-2.39 (m, 1H), 2.33 (s, 3H), 2.07 (br d, J=5.5 Hz, 1H). LCMS (Method A): retention time 0.55 min, [M+H]⁺ 365.5.

Example 146

4-{[({2-[2-(2,6-Dioxopiperidin-3-yl)-1-oxo-2,3-dihydro-1H-isoindol-5-yl]pyridin-4-yl}methyl)(methyl)amino]methyl}-N,N-dimethylbenzene-1-sulfonamide

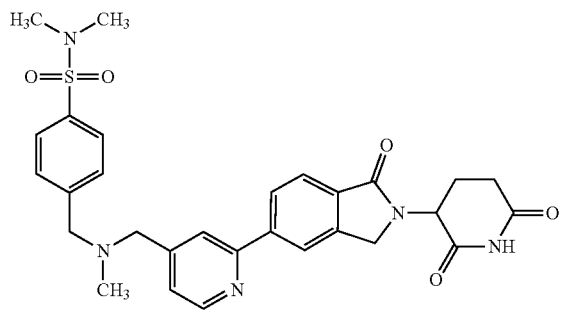

(146)

Step 1: 3-(5-(4-((Methylamino)methyl)pyridin-2-yl)-1-oxoisoindolin-2-yl)piperidine-2,6-dione bis-hydrochloride A flask was charged with tert-butyl (S)-5-amino-4-(5-(4-(((tert-butoxycarbonyl) (methyl)amino)methyl)pyridin-2-yl)-1-oxoisoindolin-2-yl)-5-oxopentanoate (2.0 g, 3.71 mmol), benzenesulfonic acid (1.762 g, 11.14 mmol), and acetonitrile (60 mL). The resulting mixture was heated to reflux and held at that temperature for 4 h. The reaction mixture was concentrated. The resulting residue was treated with 50 mL of 2 M HCl in diethyl ether and stirred for 15 min. The resulting solid was collected by filtration, rinsing with diethyl ether, and air dried to give the product (1.4 g, 78%) as the bis-HCl salt. MS (ES): m/z=365.2 [M+H]⁺.

Step 2: 4-{[({2-[2-(2,6-Dioxopiperidin-3-yl)-1-oxo-2,3-dihydro-1H-isoindol-5-yl]pyridin-4-yl}methyl)(methyl)amino]methyl}-N,N-dimethylbenzene-1-sulfonamide A vial was charged with 3-(5-(4-((methylamino)methyl)pyridin-2-yl)-1-oxoisoindolin-2-yl)piperidine-2,6-dione bis-hydrochloride (20 mg, 0.046 mmol), 4-(bromomethyl)-N,N-dimethylbenzenesulfonamide (25.4 mg, 0.091 mmol), and DMF (1 mL). To this was added N-ethyl-N-isopropyl-propan-2-amine (35.5 mg, 0.274 mmol). The reaction mixture was warmed to 50° C. and held at that temperature for 4 h. The reaction was quenched by addition of acetic acid (0.2 mL). The reaction mixture was purified by HPLC to give the product (12.1 mg, 46%). ¹H NMR (500 MHz, DMSO-d6) δ 11.02 (s, 1H), 8.66 (d, J=4.9 Hz, 1H), 8.30 (s, 1H), 8.22 (br d, J=7.9 Hz, 1H), 8.01 (s, 1H), 7.86 (d, J=7.9 Hz, 1H), 7.75-7.69 (m, 2H), 7.69-7.63 (m, 2H), 7.45 (d, J=4.3 Hz, 1H), 5.12 (br dd, J=13.1, 4.9 Hz, 1H), 4.62-4.52 (m, 1H), 4.49-4.39 (m, 1H), 3.61 (br s, 4H), 2.98-2.85 (m, 1H), 2.65 (br d, J=16.2 Hz, 1H), 2.52 (br s, 6H), 2.44 (qd, J=13.1, 4.4 Hz, 1H), 2.19 (s, 3H), 2.11-2.00 (m, 1H). LCMS (Method A): retention time 1.10 min, [M+H]⁺ 562.1.

Examples 147-162

The compounds in Table 2 were prepared according to the procedures described for Example 146, replacing 4-(bromomethyl)-N,N-dimethylbenzenesulfonamide with the appropriate bromide:

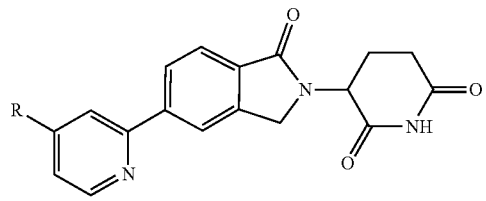

TABLE 2

| Ex. No. | R | LC/MS [M + H]+ | Retention Time (min) | HPLC Method |
|---|---|---|---|---|
| 147 | ![F-phenyl-CH2-N(CH3)-] | 473.3 | 1.84 | B |
| 148 | ![F3C-phenyl-CH2-N(CH3)-] | 523.4 | 1.89 | B |

TABLE 2-continued

| Ex. No. | R | LC/MS [M + H]+ | Retention Time (min) | HPLC Method |
|---|---|---|---|---|
| 149 | 4-(trifluoromethyl)benzyl-N(CH3)- | 523.3 | 2.03 | B |
| 150 | 4-cyanobenzyl-N(CH3)- | 480.3 | 1.00 | A |
| 151 | 4-nitrobenzyl-N(CH3)- | 500 | 1.79 | B |
| 152 | 3,4-difluorobenzyl-N(CH3)- | 491.3 | 1.90 | B |
| 153 | 4-(methoxycarbonyl)benzyl-N(CH3)- | 513.4 | 1.63 | B |
| 154 | 4-chlorobenzyl-N(CH3)- | 489.1 | 1.98 | B |
| 155 | quinolin-8-ylmethyl-N(CH3)- | 506.4 | 1.25 | B |
| 156 | 3-(trifluoromethoxy)benzyl-N(CH3)- | 539.1 | 2.10 | B |
| 157 | 4-(methylsulfonyl)benzyl-N(CH3)- | 533.1 | 1.48 | B |
| 158 | 3-methoxybenzyl-N(CH3)- | 485.3 | 1.76 | B |
| 159 | pyridin-3-ylmethyl-N(CH3)- | 456.2 | 1.16 | B |

TABLE 2-continued

| Ex. No. | R | LC/MS [M + H]+ | Retention Time (min) | HPLC Method |
|---|---|---|---|---|
| 160 | pyridin-3-ylmethyl-N(CH3)- | 456.4 | 1.20 | B |
| 161 | 4-methylbenzyl-N(CH3)- | 469.1 | 1.97 | B |
| 162 | naphthalen-2-ylmethyl-N(CH3)- | 505.3 | 2.07 | B |

Example 163

3-(5-{4-[(Dibenzylamino)methyl]pyridin-2-yl}-1-oxo-2,3-dihydro-1H-isoindol-2-yl)piperidine-2,6-dione

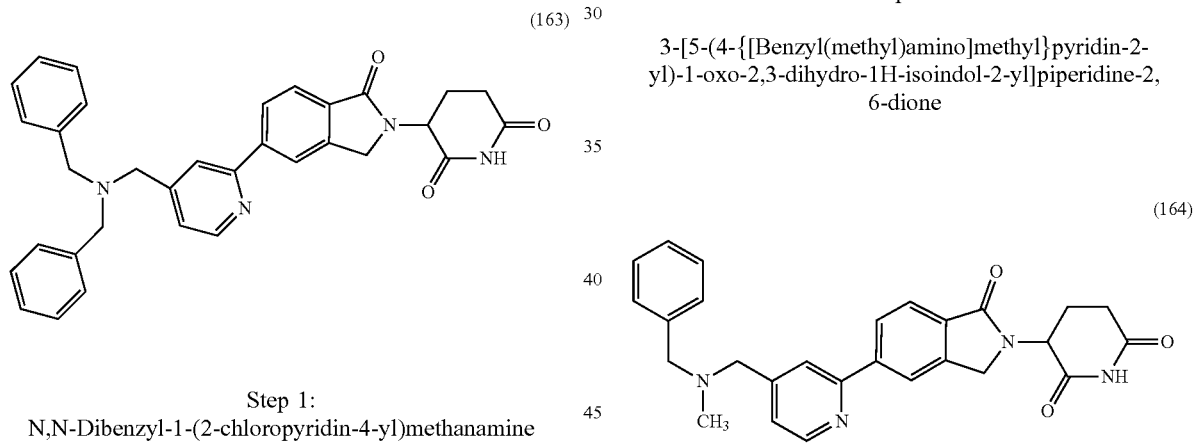

(163)

Step 1: N,N-Dibenzyl-1-(2-chloropyridin-4-yl)methanamine

To a solution of (2-chloropyridin-4-yl)methanamine, 2 HCl (40 mg, 0.186 mmol) dissolved in DMF (1 mL) were added sodium hydride (29.7 mg, 0.742 mmol) and (bromomethyl)benzene (69.8 mg, 0.408 mmol). The resulting mixture was stirred at room temperature for 16 h. The reaction mixture was diluted with EtOAc and washed with brine. The organics were concentrated and purified by preparative HPLC to give the product (31 mg, 52%). MS (ES): m/z=323.2 [M+H]+.

Step 2: 3-(5-{4-[(Dibenzylamino)methyl]pyridin-2-yl}-1-oxo-2,3-dihydro-1H-isoindol-2-yl)piperidine-2,6-dione Example 163 was prepared according to the general method used to prepare 3-(5-{4-[(methylamino)methyl]pyridin-2-yl}-1-oxo-2,3-dihydro-1H-isoindol-2-yl) piperidine-2,6-dione. $^1$H NMR (500 MHz, DMSO-d6) δ 11.02 (br d, J=4.0 Hz, 1H), 8.67 (d, J=4.9 Hz, 1H), 8.28 (s, 1H), 8.21 (br d, J=7.9 Hz, 1H), 8.00 (s, 1H), 7.86 (d, J=7.9 Hz, 1H), 7.49 (br d, J=4.6 Hz, 1H), 7.47-7.42 (m, 4H), 7.38 (t, J=7.5 Hz, 4H), 7.31-7.24 (m, 2H), 5.17 (br dd, J=13.3, 5.0 Hz, 1H), 4.63-4.53 (m, 1H), 4.51-4.39 (m, 1H), 3.67 (s, 2H), 3.61 (s, 4H), 3.00-2.89 (m, 1H), 2.71-2.60 (m, 1H), 2.46 (td, J=13.3, 9.2 Hz, 1H), 2.07 (br dd, J=10.8, 5.6 Hz, 1H). LCMS (Method B): retention time 2.36 min, [M+H]+ 531.2.

Example 164

3-[5-(4-{[Benzyl(methyl)amino]methyl}pyridin-2-yl)-1-oxo-2,3-dihydro-1H-isoindol-2-yl]piperidine-2,6-dione (164)

Step 1: N-benzyl-1-(2-chloropyridin-4-yl)-N-methylmethanamine

To a solution of (2-chloropyridin-4-yl)methanamine, 2 HCl (43.4 mg, 0.201 mmol) in DMF (1 mL) were added sodium hydride (32.2 mg, 0.805 mmol) and (bromomethyl)benzene (36.1 mg, 0.211 mmol). The resulting mixture was stirred at room temperature for 1 h. To this was added iodomethane (30 mg, 0.211 mmol). The reaction mixture was stirred overnight. The product was isolated by preparative HPLC to give 23 mg (46%). MS (ES): m/z=247.1 [M+H]+.

Step 2: 3-[5-(4-{[Benzyl(methyl)amino]methyl}pyridin-2-yl)-1-oxo-2,3-dihydro-1H-isoindol-2-yl]piperidine-2,6-dione Example 164 was prepared according to the general method used to prepare 3-(5-{4-[(methylamino)methyl]

pyridin-2-yl}-1-oxo-2,3-dihydro-1H-isoindol-2-yl)piperidine-2,6-dione. ¹H NMR (500 MHz, DMSO-d6) δ 11.03 (s, 1H), 8.81 (d, J=4.9 Hz, 1H), 8.32 (s, 1H), 8.24 (d, J=8.2 Hz, 1H), 8.21 (s, 1H), 7.90 (d, J=7.9 Hz, 1H), 7.60-7.53 (m, 3H), 7.51-7.45 (m, 3H), 5.14 (dd, J=13.4, 5.2 Hz, 1H), 4.63-4.54 (m, 1H), 4.50-4.35 (m, 4H), 3.62-3.48 (m, 1H), 2.98-2.87 (m, 1H), 2.68-2.61 (m, 4H), 2.49-2.37 (m, 1H), 2.13-2.02 (m, 1H). LCMS (Method B): retention time 1.66 min, [M+H]⁺ 455.1.

Example 165

3-(5-{4-[(Azetidin-1-yl)methyl]pyridin-2-yl}-1-oxo-2,3-dihydro-1H-isoindol-2-yl) piperidine-2,6-dione (165)

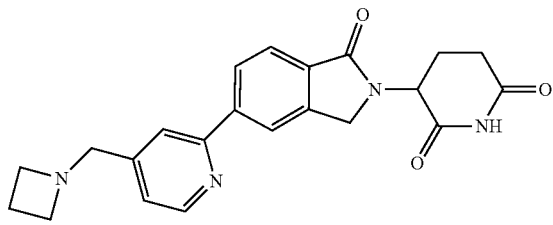

Step 1: 4-(Azetidin-1-ylmethyl)-2-chloropyridine

A vial was charged with 2-chloro-4-(chloromethyl)pyridine (44 mg, 0.187 mmol), THF (1.5 mL) and azetidine (13.44 mg, 0.234 mmol). After stirring for 5 min, N-ethyl-N-isopropylpropan-2-amine (0.130 mL, 0.749 mmol) was added. The reaction mixture was warmed to 40° C. and held at that temperature for 3 h. The reaction mixture was diluted with EtOAc, washed with brine, dried over sodium sulfate, and concentrated to give the product (31 mg, 91%). MS (ES): m/z=182.9 [M+H]⁺.

Step 2: 3-(5-{4-[(Azetidin-1-yl)methyl]pyridin-2-yl}-1-oxo-2,3-dihydro-1H-isoindol-2-yl)piperidine-2,6-dione A microwave vial was charged with 4-(azetidin-1-ylmethyl)-2-chloropyridine (17.4 mg, 0.095 mmol), tert-butyl (S)-5-amino-5-oxo-4-(1-oxo-5-(4,4,5,5-tetramethyl-1,3,2-dioxaborolan-2-yl)isoindolin-2-yl)pentanoate (52.9 mg, 0.119 mmol), Pd(dtbpf)Cl₂ (1.863 mg, 2.86 μmol), 1,4-dioxane (1 mL), and aqueous K₃PO₄ (0.159 mL, 0.476 mmol). The vial was sealed and the air replaced with nitrogen. The reaction mixture was heated via microwave for 10 min at 120° C. The reaction mixture was cooled, diluted with EtOAc, and washed with brine. The organics were dried over sodium sulfate and concentrated. The resulting residue was dissolved in a solution of PhSO₃H solution in acetonitrile (0.5 mL, 1.44 g in 40 mL) and heated via microwave for 10 min at 120° C. The reaction mixture was concentrated and purified by preparative HPLC to give Example 165 (8.1 mg, 18%). ¹H NMR (500 MHz, DMSO-d6) δ 8.61 (d, J=4.9 Hz, 1H), 8.29 (s, 1H), 8.21 (br d, J=7.6 Hz, 1H), 7.90 (s, 1H), 7.84 (d, J=8.1 Hz, 1H), 7.31 (br d, J=4.9 Hz, 1H), 5.17-5.08 (m, 1H), 4.60-4.39 (m, 2H), 3.65 (br s, 2H), 3.20 (t, J=7.0 Hz, 3H), 2.96-2.85 (m, 1H), 2.68-2.60 (m, 1H), 2.48-2.35 (m, 2H), 2.11-1.96 (m, 3H) LCMS (Method A): retention time 0.91 min, [M+H]⁺ 390.9.

Example 166

3-(5-{4-[(Morpholin-4-yl)methyl]pyridin-2-yl}-1-oxo-2,3-dihydro-1H-isoindol-2-yl) piperidine-2,6-dione (166)

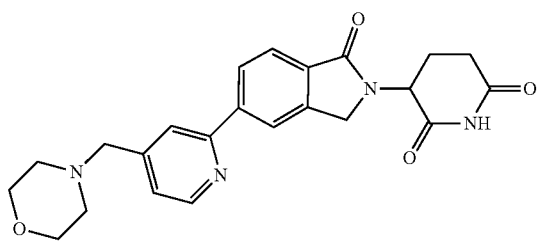

Example 166 was prepared according the general procedure used to prepare 3-(5-{4-[(azetidin-1-yl)methyl]pyridin-2-yl}-1-oxo-2,3-dihydro-1H-isoindol-2-yl)piperidine-2,6-dione. ¹H NMR (500 MHz, DMSO-d6) δ 11.01 (s, 1H), 8.64 (d, J=5.0 Hz, 1H), 8.30 (s, 1H), 8.22 (br d, J=8.0 Hz, 1H), 7.97 (s, 1H), 7.84 (d, J=8.0 Hz, 1H), 7.38 (d, J=4.5 Hz, 1H), 5.19-5.05 (m, 1H), 4.62-4.35 (m, 2H), 3.56-3.54 (m, 6H), 2.97-2.84 (m, 1H), 2.67-2.59 (m, 1H), 2.46-2.34 (m, 5H), 2.12-1.99 (m, 1H). LCMS (Method B): retention time 1.23 min, [M+H]⁺ 421.1.

Example 167

4-({2-[2-(2,6-Dioxopiperidin-3-yl)-1-oxo-2,3-dihydro-1H-isoindol-5-yl]pyridin-4-yl}methyl)-1λ6-thiomorpholine-1,1-dione (167)

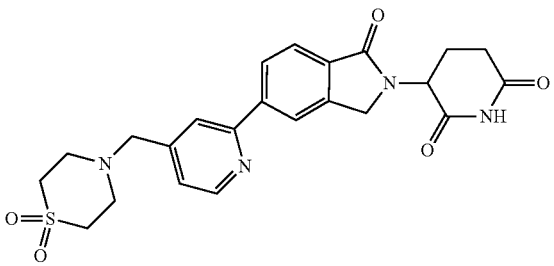

Example 167 was prepared according the general procedure used to prepare 3-(5-{4-[(azetidin-1-yl)methyl]pyridin-2-yl}-1-oxo-2,3-dihydro-1H-isoindol-2-yl)piperidine-2,6-dione. ¹H NMR (500 MHz, DMSO-d6) δ 11.01 (s, 1H), 8.66 (d, J=5.0 Hz, 1H), 8.32 (br s, 1H), 8.24 (br d, J=8.0 Hz, 1H), 8.02 (br s, 1H), 7.85 (d, J=8.0 Hz, 1H), 7.41 (d, J=4.8 Hz, 1H), 5.18-5.07 (m, 1H), 4.60-4.38 (m, 2H), 3.17 (br s, 3H), 2.94 (br s, 4H), 2.63 (br d, J=15.3 Hz, 1H), 2.51 (br s, 4H), 2.48-2.36 (m, 1H), 2.12-1.99 (m, 1H). LCMS (Method B): retention time 1.13 min, [M+H]⁺ 469.0.

Example 168

3-{5-[4-({[(6-Methoxypyridin-3-yl)methyl](methyl)amino}methyl)pyridin-2-yl]-1-oxo-2,3-dihydro-1H-isoindol-2-yl}piperidine-2,6-dione (168)

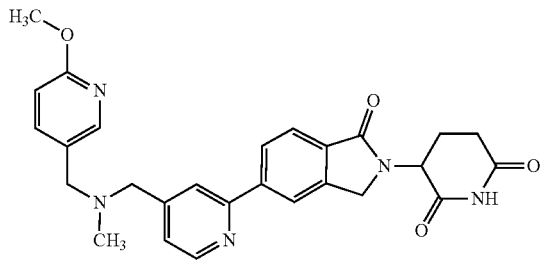

A vial was charged with 3-(5-(4-((methylamino)methyl)pyridin-2-yl)-1-oxoisoindolin-2-yl)piperidine-2,6-dione bis-hydrochloride (20 mg, 0.046 mmol), 6-methoxynicotinaldehyde (18.8 mg, 0.137 mmol), and DMF (1 mL). After stirring for 10 min at room temperature, sodium triacetoxyborohydride (29.1 mg, 0.137 mmol) was added. The reaction mixture was warmed to 50° C. and held at that temperature overnight. The reaction mixture was filtered and purified by preparative HPLC to give 2.5 mg (11%). $^1$H NMR (500 MHz, DMSO-d6) δ 11.00 (s, 1H), 8.73 (d, J=4.8 Hz, 1H), 8.27 (s, 1H), 8.22 (s, 1H), 8.19 (d, J=8.0 Hz, 1H), 8.08 (s, 1H), 7.87 (d, J=8.0 Hz, 1H), 7.79 (dd, J=8.6, 2.3 Hz, 1H), 7.49 (d, J=4.6 Hz, 1H), 6.86 (d, J=8.6 Hz, 1H), 5.09 (br dd, J=13.1, 5.1 Hz, 1H), 4.56 (d, J=17.6 Hz, 1H), 4.48-4.37 (m, 1H), 3.80-3.78 (m, 7H), 2.88 (ddd, J=18.0, 13.3, 5.1 Hz, 1H), 2.69-2.61 (m, 1H), 2.49 (br s, 3H), 2.42 (br dd, J=12.7, 4.1 Hz, 1H), 2.11-2.01 (m, 1H). LCMS (Method A): retention time 1.02 min, [M+H]$^+$ 486.3.

Examples 169-185

The compounds in Table 3 were prepared according to the general procedures described for Example 168, replacing 6-methoxynicotinaldehyde with the appropriate aldehyde or ketone:

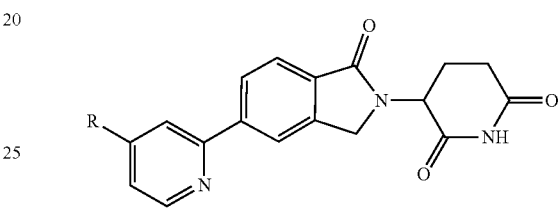

TABLE 3

| Ex. No. | R | LC/MS [M + H]$^+$ | Retention Time (min) | HPLC Method |
|---|---|---|---|---|
| 169 | | 495.3 | 0.93 | A |
| 170 | | 462.1 | 1.03 | B |
| 171 | | 469.2 | 0.85 | A |
| 172 | | 445.3 | 1.51 | B |
| 173 | | 419.1 | 0.99 | A |

TABLE 3-continued

| Ex. No. | R | LC/MS [M + H]⁺ | Retention Time (min) | HPLC Method |
|---|---|---|---|---|
| 174 | H₃C-imidazole-CH₂-N(CH₃)- | 459.1 | 1.25 | B |
| 175 | cyclopentyl-CH₂-N(CH₃)- | 447.1 | 1.90 | B |
| 176 | thiazol-2-yl-CH₂-N(CH₃)- | 462.0 | 1.00 | A |
| 177 | 4-(imidazol-1-yl)phenyl-CH₂-N(CH₃)- | 521.2 | 1.50 | B |
| 178 | cyclobutyl-CH₂-N(CH₃)- | 419.1 | 1.37 | B |
| 179 | (H₃C)₂CH-CH₂-N(CH₃)- | 421.1 | 1.78 | B |
| 180 | (H₃C)₂CH-CH₂-CH₂-N(CH₃)- | 435.2 | 0.75 | A |
| 181 | HO-CH₂-CH(CH₃)-N(CH₃)- | 423.1 | 1.08 | B |
| 182 | tetrahydrofuran-3-yl-N(CH₃)- | 449.2 | 1.36 | B |
| 183 | quinoxalin-2-yl-CH₂-N(CH₃)- | 507.3 | 1.47 | B |
| 184 | F₃C-CH₂-CH₂-N(CH₃)- | 461.4 | 0.64 | A |

TABLE 3-continued

| Ex. No. | R | LC/MS [M + H]+ | Retention Time (min) | HPLC Method |
|---|---|---|---|---|
| 185 | 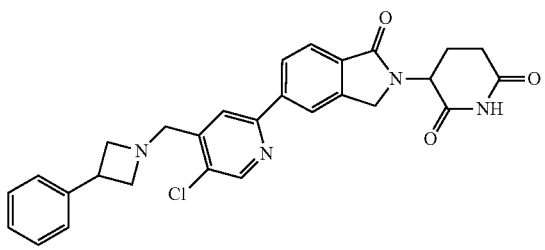 | 437.2 | 0.95 | A |

Example 186

3-(5-(5-chloro-4-((3-phenylazetidin-1-yl)methyl)pyridin-2-yl)-1-oxoisoindolin-2-yl)piperidine-2,6-dione (186)

Step 1: tert-butyl (S)-5-amino-4-(5-(5-chloro-4-(hydroxymethyl)pyridin-2-yl)-1-oxoisoindolin-2-yl)-5-oxopentanoate A 20 mL vial was charged with (2,5-dichloropyridin-4-yl)methanol (0.2 g, 1.124 mmol), tert-butyl (S)-5-amino-5-oxo-4-(1-oxo-5-(4,4,5,5-tetramethyl-1,3,2-dioxaborolan-2-yl)isoindolin-2-yl)pentanoate (0.749 g, 1.685 mmol), Pd(dtbpf)Cl$_2$ (0.022 g, 0.034 mmol), 1,4-dioxane (5.62 mL) and 3 M aqueous K$_3$PO$_4$ (1.873 mL, 5.62 mmol). The vial was sealed and the air was replaced with nitrogen. It was heated at 60° C. for 16 hrs. The reaction mixture was cooled to room temperature, diluted with EtOAc (25 mL), washed with brine, and the layers separated. The organics were dried over sodium sulfate, filtered, and concentrated. The crude product was purified using silica gel column by ISCO column chromatography (40 g Gold column, eluting with 0-100% of 20% methanolic ammonia in DCM-DCM) to give tert-butyl-5-amino-4-(5-(5-chloro-4-(hydroxymethyl)pyridin-2-yl)-1-oxoisoindolin-2-yl)-5-oxopentanoate (320 mg, 0.668 mmol, 59.4% yield) as light brown solid. The enantiomeric excess of this material and subsequent intermediates were not determined. MS (ES): m/z=460.05 [M+H]+.

Step 2: 3-(5-(5-chloro-4-(chloromethyl)pyridin-2-yl)-1-oxoisoindolin-2-yl)piperidine-2,6-dione Thionyl chloride (0.132 mL, 1.826 mmol) was added dropwise to a cooled (0° C.) solution of tert-butyl-5-amino-4-(5-(5-chloro-4-(hydroxymethyl)pyridin-2-yl)-1-oxoisoindolin-2-yl)-5-oxopentanoate (0.280 g, 0.609 mmol) in DCM (3.00 mL). After 10 minutes, the ice-bath was removed, and the reaction mixture was allowed to warm to room temperature. After 30 minutes, the reaction mixture was concentrated to dryness. The residue was dissolved in acetic acid (3 mL) and benzenesulfonic acid (0.212 g, 1.339 mmol) was added and the reaction mixture was heated at 120° C. in microwave oven for 25 minutes. The reaction mixture was concentrated to dryness, and 2 mL of 3 M HCl in MeOH was added and stirred at 0° C. (ice-water bath) until there was complete dissolution. Then 8 mL of EtOAc was added, and stirred. After 5 minutes, the reaction mixture was allowed to stay still in the ice-water bath for 30 minutes. The precipitate was filtered, washed with EtOAc, and then air-dried to give 3-(5-(5-chloro-4-(chloromethyl)pyridin-2-yl)-1-oxoisoindolin-2-yl)piperidine-2,6-dione (180 mg, 0.401 mmol, 65.8% yield) as HCl salt. MS (ES): m/z=404.3, 406.3 [M+H]+.

Step 3: 3-(5-(5-chloro-4-((3-phenylazetidin-1-yl)methyl)pyridin-2-yl)-1-oxoisoindolin-2-yl)piperidine-2,6-dione To a solution of 3-(5-(5-chloro-4-(chloromethyl)pyridin-2-yl)-1-oxoisoindolin-2-yl)piperidine-2,6-dione, HCl (40 mg, 0.091 mmol) in DMF (0.5 mL) was added 3-phenylazetidine, HCl (17.71 mg, 0.104 mmol) followed by Hunig's base (95 µL, 0.545 mmol). The resulting mixture was heated to 80° C. with stirring for 3 hours. It was then cooled and diluted further with DMF (0.5 mL). The crude material was purified via preparative LC/MS with the following conditions: Column: XBridge C18, 200 mm×19 mm, 5-µm particles; Mobile Phase A: 5:95 acetonitrile:water with ammonium acetate; Mobile Phase B: 95:5 acetonitrile:water with ammonium acetate; Gradient: a 0-minute hold at 35% B, 35-75% B over 22 minutes, then a 0-minute hold at 100% B; Flow Rate: 20 mL/min; Column Temperature: 25° C. Fraction collection was triggered by MS signals. Fractions containing the desired product were combined and dried via centrifugal evaporation to obtain 3-(5-(5-chloro-4-((3-phenylazetidin-1-yl)methyl)pyridin-2-yl)-1-oxoisoindolin-2-yl)piperidine-2,6-dione (15.5 mg, 0.030 mmol, 33.1% yield). LCMS (Method A): Retention Time 1.28 min; MS (ES): m/z=501.17 [M+H]+; $^1$H NMR (400 MHz, DMSO-d6) δ 8.89 (s, 1H), 8.82 (s, 1H), 8.33 (s, 1H), 8.24 (m, m 1H), 7.99 (s, 1H), 7.84 (d, J=8.0 Hz, 1H), 7.41-7.31 (m, 5H), 7.26-7.20 (m, 1H), 5.16 (m, 1H), 4.56 (d, J=17.4 Hz, 1H), 4.44 (d, J=17.4 Hz, 1H), 3.80-3.66 (m, 5H), 3.26-3.18 (m, 2H), 3.00-2.88 (m, 1H), 2.49-2.37 (m, 1H), 2.10-2.01 (m, 1H).

Example 187

The compound in Table 4 were prepared according to the general procedures described for Example 186, replacing 3-phenylazetidine with the appropriate amine.

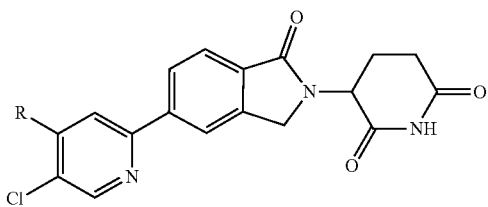

TABLE 4

| Ex. No. | R | LC/MS [M + H]+ | Retention Time (min) | HPLC Method |
|---|---|---|---|---|
| 187 | ![structure] | 501.15 | 1.15 | A |

Example 188

3-(5-(5-fluoro-4-((3-phenylazetidin-1-yl)methyl)pyridin-2-yl)-1-oxoisoindolin-2-yl) piperidine-2,6-dione

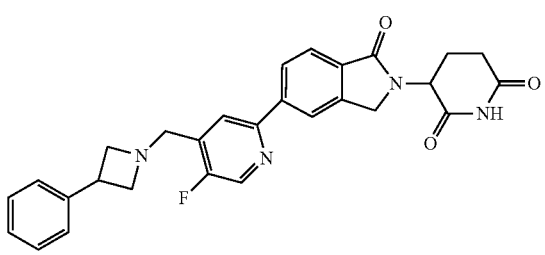

(188)

Step 1: tert-butyl 5-amino-4-(5-(5-fluoro-4-(hydroxymethyl)pyridin-2-yl)-1-oxoisoindolin-2-yl)-5-oxopentanoate A 20 mL vial was charged with (2-chloro-5-fluoropyridin-4-yl)methanol (0.4 g, 2.476 mmol), tert-butyl (S)-5-amino-5-oxo-4-(1-oxo-5-(4,4,5,5-tetramethyl-1,3,2-dioxaborolan-2-yl)isoindolin-2-yl)pentanoate (1.650 g, 3.71 mmol), Pd(dtbpf)Cl$_2$ (0.048 g, 0.074 mmol), 1,4-dioxane (12.38 mL) and 3 M aqueous solution of K$_3$PO$_4$ (4.13 mL, 12.38 mmol). The vial was sealed and the air was replaced with nitrogen. It was heated at 60° C. for 16 hrs. The reaction mixture was cooled to room temperature, diluted with EtOAc (25 mL), washed with brine, and the layers separated. The organics were dried over sodium sulfate, filtered, and concentrated. The crude product was purified using silica gel column by ISCO column chromatography (40 g Gold column, eluting with 0-100% of 20% methanolic ammonia in DCM-DCM) to give tert-butyl-5-amino-4-(5-(5-fluoro-4-(hydroxymethyl)pyridin-2-yl)-1-oxoisoindolin-2-yl)-5-oxopentanoate (650 mg, 1.466 mmol, 59.2% yield) as light brown solid. The enantiomeric excess of this material and subsequent intermediates were not determined. MS (ES): m/z=444.04 [M+H]+.

Step 2: 3-(5-(5-fluoro-4-(chloromethyl)pyridin-2-yl)-1-oxoisoindolin-2-yl)piperidine-2,6-dione Thionyl chloride (0.319 mL, 4.40 mmol) was added dropwise to a cooled (0° C.) solution of tert-butyl 5-amino-4-(5-(5-fluoro-4-(hydroxymethyl)pyridin-2-yl)-1-oxoisoindolin-2-yl)-5-oxopentanoate (0.65 g, 1.466 mmol) in DCM (7.5 mL). After 10 minutes, the ice-bath was removed, and the reaction mixture was allowed to warm to room temperature. After 30 minutes, the reaction mixture was concentrated to dryness. The residue was dissolved in acetic acid (3 mL) and benzenesulfonic acid (0.510 g, 3.22 mmol) was added and the reaction mixture was heated at 120° C. in microwave oven for 25 minutes. The reaction mixture was concentrated to dryness, and 4 mL of 3 M HCl in MeOH was added and stirred at 0° C. (ice-water bath) until there was complete dissolution. Then 12 mL of EtOAc was added, and stirred. After 5 minutes, the reaction mixture was allowed to stay still in the ice-water bath for 30 minutes. The precipitate was filtered, washed with EtOAc, and then air-dried to give 3-(5-(4-(chloromethyl)-5-fluoropyridin-2-yl)-1-oxoisoindolin-2-yl)piperidine-2,6-dione (480 mg, 1.238 mmol, 84% yield) as HCl salt. MS (ES): m/z=388.2 [M+H]+.

Step 3: 3-(5-(5-fluoro-4-((3-phenylazetidin-1-yl)methyl)pyridin-2-yl)-1-oxoisoindolin-2-yl)piperidine-2,6-dione To 3-(5-(3-(chloromethyl)-4-fluorophenyl)-1-oxoisoindolin-2-yl)piperidine-2,6-dione, HCl (55 mg, 0.130 mmol) dissolved in DMF (650 μL) was added 3-phenylazetidine, HCl (25.4 mg, 0.149 mmol) followed by Hunig's base (136 μL, 0.780 mmol). The resulting mixture was heated to 80° C. with stirring for 3 hours. It was then cooled and diluted further with DMF (0.5 mL). The crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 35% B, 35-75% B over 22 minutes, then a 0-minute hold at 100% B; Flow Rate: 20 mL/min; Column Temperature: 25° C. Fraction collection was triggered by MS signals. Fractions containing the desired product were combined and dried via centrifugal evaporation to obtain 3-(5-(5-fluoro-4-((3-phenylazetidin-1-yl)methyl)pyridin-2-yl)-1-oxoisoindolin-2-yl)piperidine-2,6-dione (7.1 mg, 0.015 mmol, 11.28% yield). LCMS (Method A): Retention Time 1.78 min; MS (ES): m/z=485.3 [M+H]+; $^1$H NMR (400 MHz, DMSO-d6) δ 9.1 (s, 1H), 8.9 (s, 1H), 8.43 (s, 1H), 8.30 (m, m 1H), 8.01 (s, 1H), 7.81 (d, J=8.0 Hz, 1H), 7.5-7.38 (m, 5H), 7.26-7.20 (m, 1H), 5.3 (m, 1H), 4.61 (d, J=17.4 Hz, 1H), 4.51 (d, J=17.4 Hz, 1H), 3.80-3.66 (m, 5H), 3.26-3.18 (m, 2H), 3.00-2.88 (m, 1H), 2.49-2.37 (m, 1H), 2.10-2.01 (m, 1H).

Examples 189-190

The compounds in Table 5 were prepared according to the procedures described herein, replacing 3-phenylazetidine with the appropriate amine:

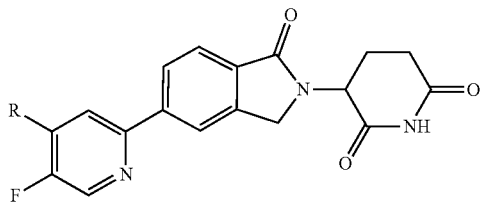

TABLE 5

| Ex. No. | R | LC/MS [M + H]+ | Retention Time (min) | HPLC Method |
|---|---|---|---|---|
| 189 | (phenylazetidinyl) | 485.06 | 1.90 | A |
| 190 | (pyridin-3-yl-azetidinyl) | 486.07 | 1.39 | A |

Example 191

3-(5-(3-fluoro-4-((3-phenylazetidin-1-yl)methyl)pyridin-2-yl)-1-oxoisoindolin-2-yl) piperidine-2,6-dione (191)

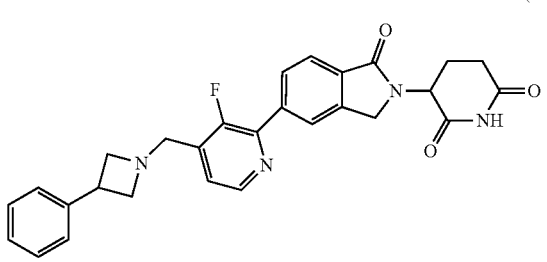

Step 1: tert-butyl 5-amino-4-(5-(3-fluoro-4-(hydroxymethyl)pyridin-2-yl)-1-oxoisoindolin-2-yl)-5-oxopentanoate A 20 mL vial was charged with (2-chloro-3-fluoropyridin-4-yl)methanol (400 mg, 2.476 mmol), tert-butyl (S)-5-amino-5-oxo-4-(1-oxo-5-(4,4,5,5-tetramethyl-1,3,2-dioxaborolan-2-yl)isoindolin-2-yl)pentanoate (1.650 g, 3.71 mmol), Pd(dtbpf)Cl$_2$ (0.048 g, 0.074 mmol), 1,4-dioxane (12.38 mL) and 3 M aqueous solution of K$_3$PO$_4$ (4.13 mL, 12.38 mmol). The vial was sealed and the air was replaced with nitrogen. It was heated at 60° C. for 16 hrs. The reaction mixture was cooled to room temperature, diluted with EtOAc (40 mL), washed with brine, and the layers separated. The organics were dried over sodium sulfate, filtered, and concentrated. The crude product was purified using silica gel column by ISCO column chromatography (40 g Gold, eluting with 0-100% of 20% methanolic ammonia in DCM-DCM) to give tert-butyl 5-amino-4-(5-(3-fluoro-4-(hydroxymethyl)pyridin-2-yl)-1-oxoisoindolin-2-yl)-5-oxopentanoate (630 mg, 1.421 mmol, 57.4% yield) as brown solid. The enantiomeric excess of this material and subsequent intermediates were not determined. MS (ES): m/z=444.4 [M+H]+.

Step 2: 3-(5-(4-(chloromethyl)-3-fluoropyridin-2-yl)-1-oxoisoindolin-2-yl)piperidine-2,6-dione Thionyl chloride (0.304 mL, 4.19 mmol) was added dropwise to a cooled (0° C.) solution of tert-butyl 5-amino-4-(5-(3-fluoro-4-(hydroxymethyl)pyridin-2-yl)-1-oxoisoindolin-2-yl)-5-oxopentanoate (0.62 g, 1.398 mmol) in DCM (7.5 mL). After 10 minutes, the ice-bath was removed, and the reaction mixture was allowed to warm to room temperature. After 30 minutes, the reaction mixture was concentrated to dryness. The residue was dissolved in acetic acid (4 mL) and benzenesulfonic acid (0.486 g, 3.08 mmol) was added and the reaction mixture was heated at 120° C. in microwave oven for 30 minutes. The reaction mixture was concentrated to dryness, and 4 mL of 3 M HCl in MeOH was added and stirred at 0° C. (ice-water bath) until there was complete dissolution. Then 12 mL of EtOAc was added, and stirred. After 5 minutes, the reaction mixture was allowed to stay still in the ice-water bath for 30 minutes. The precipitate was filtered, washed with EtOAc, and then air-dried to give 3-(5-(4-(chloromethyl)-3-fluoropyridin-2-yl)-1-oxoisoindolin-2-yl)piperidine-2,6-dione (465 mg, 1.199 mmol, 86% yield) as HCl salt. MS (ES): m/z=388.2 [M+H]+.

Step 3: 3-(5-(3-fluoro-4-((3-phenylazetidin-1-yl)methyl)pyridin-2-yl)-1-oxoisoindolin-2-yl)piperidine-2,6-dione To 3-(5-(4-(chloromethyl)-3-fluoropyridin-2-yl)-1-oxoisoindolin-2-yl)piperidine-2,6-dione, HCl (35 mg, 0.082 mmol) dissolved in DMF (30 mL) was added 3-phenylazetidine, HCl (16.10 mg, 0.095 mmol) followed by Hunig's base (0.086 mL, 0.495 mmol). The resulting mixture was heated to 80° C. with stirring for 3 hours. It was then cooled and diluted further with DMF (0.5 mL). The crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 35% B, 35-75% B over 22 minutes, then a 0-minute hold at 100% B; Flow Rate: 20 mL/min; Column Temperature: 25° C. Fraction collection was triggered by MS signals. Fractions containing the desired product were combined and dried via centrifugal evaporation to obtain 3-(5-(3-fluoro-4-((3-phenylazetidin-1-yl)methyl)pyridin-2-yl)-1-oxoisoindolin-2-yl)piperidine-2,6-dione (15.4 mg, 0.032 mmol, 38.5% yield). LCMS (Method A): Retention Time 1.12 min; MS (ES): m/z=485.1 [M+H]+; $^1$H NMR (400 MHz, DMSO-d6) δ 8.6 (s, 1H), 8.3 (s, 1H), 8.21 (m, 1H), 8.11 (m, 1H), 7.81 (s, 1H), 7.6 (m, 1H), 7.5-7.38 (m, 5H), 7.26-7.20 (m, 1H), 5.2 (m, 1H), 4.51 (d, J=17.4 Hz, 1H), 4.34 (d, J=17.4 Hz, 1H), 3.80-3.66 (m, 5H), 3.26-3.18 (m, 2H), 3.00-2.88 (m, 1H), 2.49-2.37 (m, 1H), 2.10-2.01 (m, 1H).

Examples 192-193

The compounds in Table 6 were prepared according to the general procedures described for Example 196, replacing 3-phenylazetidine with the appropriate amine:

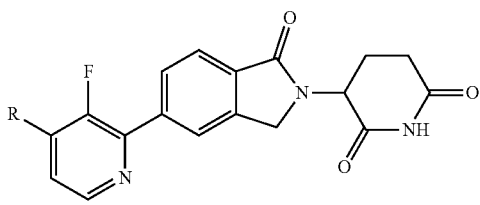

TABLE 6

| Ex. No. | R | LC/MS [M + H]+ | Retention Time (min) | HPLC Method |
|---|---|---|---|---|
| 192 | | 486.11 | 0.87 | A |
| 193 | | 485.13 | 1.71 | A |

Example 194

3-(5-(4-(((dimethylamino)methyl)pyridin-2-yl)-6-methyl-1-oxoisoindolin-2-yl)piperidine-2,6-dione

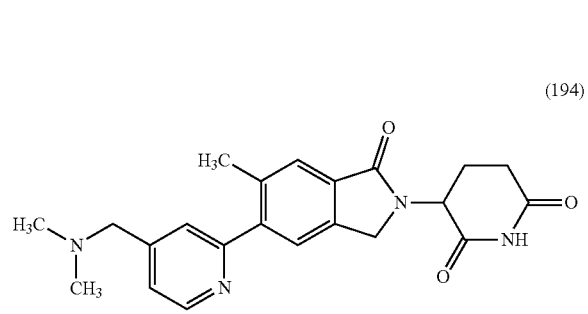 [SMILES: Cc1cc2c(cc1-c1cc(CN(C)C)ccn1)CN(C1CCC(=O)NC1=O)C2=O]

(194)

Step 1: tert-butyl (S)-5-amino-4-(6-methyl-1-oxo-5-(4,4,5,5-tetramethyl-1,3,2-dioxaborolan-2-yl)isoindolin-2-yl)-5-oxopentanoate A 40 mL pressure vial was charged with tert-butyl (S)-5-amino-4-(5-bromo-6-methyl-1-oxoisoindolin-2-yl)-5-oxopentanoate (300 mg, 0.729 mmol), 4,4,4',4',5,5,5',5'-octamethyl-2,2'-bi(1,3,2-dioxaborolane) (278 mg, 1.094 mmol), and potassium acetate (215 mg, 2.188 mmol) and then flushed with nitrogen. The solids were suspended in dioxane (10 mL) and degassed with a stream of nitrogen for about 5 min with stirring. The reaction was treated with PdCl₂(dppf)₂ (16.01 mg, 0.022 mmol) degassed again for 5 min, and heated to 95° C. for 3 h under nitrogen. The reaction mixture was diluted with EtOAc, washed with brine, and dried over MgSO₄. The filtrate was concentrated and purified by 24 gram silica gel column by ISCO and eluted using 0-40% B/DCM, (where B=15% EtOH/EtOAc+0.1% TEA) to obtain the title compound in 95% yield.

Step 2: 3-(5-(4-(((dimethylamino)methyl)pyridin-2-yl)-6-methyl-1-oxoisoindolin-2-yl) piperidine-2,6-dione A 2 mL microwave vial was charged with 1-(2-chloro-pyridin-4-yl)-N,N-dimethylmethanamine (13 mg, 0.076 mmol), tert-butyl (S)-5-amino-4-(6-methyl-1-oxo-5-(4,4,5,5-tetramethyl-1,3,2-dioxaborolan-2-yl)isoindolin-2-yl)-5-oxopentanoate (38.4 mg, 0.084 mmol), PdCl₂(dtbpf) (1.490 mg, 2.286 µmol), dioxane (1.5 mL) and 3 M aqueous K₃PO₄ (0.102 mL, 0.305 mmol). It was sealed and the air was replaced with nitrogen, and then microwaved for 10 min at 120° C. The reaction mixture was diluted with EtOAc, washed with brine, and the organic layer separated and concentrated. The crude was purified using preparative HPLC Method 1 to obtain 4.1 mg of the title compound. Analytical HPLC Method B retention time 0.89 min, [M+H]+ 393.3; ¹H NMR (500 MHz, DMSO-d6) δ 8.62 (d, J=5.0 Hz, 1H), 7.68 (s, 1H), 7.60 (s, 1H), 7.47 (s, 1H), 7.35 (d, J=4.8 Hz, 1H), 5.13 (dd, J=13.2, 5.0 Hz, 1H), 4.47 (d, J=17.2 Hz, 1H), 4.35 (d, J=17.1 Hz, 1H), 3.51 (s, 1H), 3.46-3.42 (m, 1H), 2.97-2.88 (m, 1H), 2.62 (br d, J=16.4 Hz, 1H), 2.45-2.40 (m, 1H), 2.39 (s, 3H), 2.20 (s, 6H), 2.13 (s, 1H), 2.07-1.99 (m, 1H).

Example 195

The compound in Table 7 were prepared according to the general procedures described herein, using commercial available amines.

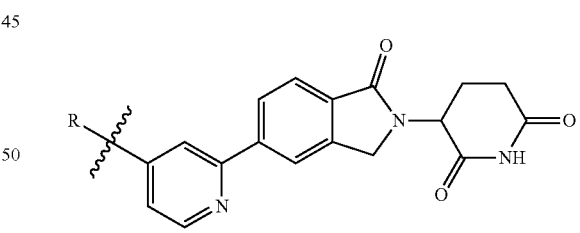

TABLE 7

| Ex. No. | R | LC/MS [M + H]+ | Retention Time (min) | HPLC Method |
|---|---|---|---|---|
| 195 | | 468.2 | 1.180 | B |

Examples 196-201

The compounds in Table 8 were prepared according to the procedures described herein, replacing tert-butyl (4-((7-azaspiro[3.5]nonan-2-yl)oxy)phenyl) carbamate with the appropriate primary or secondary amine:

Examples 202-207

The compounds in Table 9 were prepared according to the general procedures described herein:

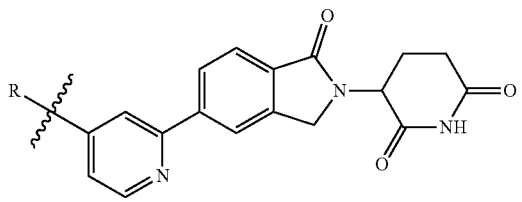

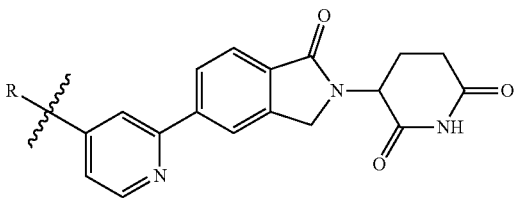

TABLE 8

| Ex. No. | R | LC/MS [M + H]+ | Retention Time (min) | HPLC Method |
|---|---|---|---|---|
| 196 | | 435.1 | 0.90 | A |
| 197 | | 420.9 | 0.91 | A |
| 198 | | 435.2 | 0.92 | A |
| 199 | | 509.2 | 1.26 | A |
| 200 | | 467.05 | 1.10 | A |
| 201 | | 391.2 | 0.95 | A |

TABLE 9

| Ex. No. | R | LC/MS [M+H]+ | Retention Time (min) | HPLC Method |
|---|---|---|---|---|
| 202 | H3C-N(CH3)-C(=O)-azetidine-N- | 462.1 | 1.10 | A |
| 203 | 3-(pyridin-3-yl)azetidin-1-yl | 468.13 | 0.89 | A |
| 204 | 2-phenylazetidin-1-yl *Isomer 1 | 467.2 | 1.25 | A |
| 205 | 2-phenylazetidin-1-yl *Isomer 2 | 467.2 | 1.07 | A |
| 206 | H2N-C(=O)-azetidine | 434.1 | 0.82 | A |
| 207 | 3,3-dimethyl-4-methoxypiperidin-1-yl | 477.3 | 1.71 | A |

*The absolute stereochemistry was not determined.

Analytical HPLC Conditions

Method A: ACQUITY UPLC® BEH C18 (3.0×50 mm) 1.7 μm; Mobile Phase A: 95:5 water:acetonitrile with 2.5 mM NH4OAc; Mobile Phase B: 5:95 water:acetonitrile with 2.5 mM NH4OAc; Temperature: 40° C.; Gradient: 20% B to 100% B over 2 min; flow: 0.7 mL/min; Detection: MS and UV (220 nm).

Method B: Column: XBridge BEH XP C18 (50×2.1) mm, 2.5 μm; Mobile Phase A: 95:5 water:acetonitrile with 10 mM NH4OAc; Mobile Phase B: 5:95 water:acetonitrile with 10 mM NH4OAc; Temperature: 50° C.; Gradient: 0% B to 100% B over 3 min; Flow: 1.1 mL/min; Detection: MS and UV (220 nm).

Method C:)(Bridge BEH XP C18 (50×2.1) mm, 2.5 μm; Mobile Phase A: 95:5 water:acetonitrile with 0.1% trifluoroacetic acid; Mobile Phase B: 5:95 water:acetonitrile with 0.1% trifluoroacetic acid; Temperature: 50° C.; Gradient: 0% B to 100% B over 3 min; Flow: 1.1 mL/min; Detection: MS and UV (220 nm).

Method D: Column-Kinetex XB-C18 (75×3 mm-2.6 μm); Mobile Phase A: 5 mM NH4COOH in water; Mobile Phase B: Acetonitrile; Gradient: 10% B to 50% B over 3 min, Flow: 1.0 mL/min; 50% B to 100% B up to 4.1 min, Flow: 1.0 mL/min; hold till 4.5 min; 4.5 min to 5.0 min 90% B Flow: 1.5 mL/min; Detection: MS and UV (220 nm).

Method E: Column-Kinetex XB-C18 (75×3 mm-2.6 μm); Mobile Phase A: 0.1% TFA in water; Mobile Phase B: Acetonitrile; Gradient: 20% B to 100% B over 4.6 min; Flow: 1.0 mL/min; Detection: MS and UV (220 nm).

Method F: Column-Kinetex XB-C18 (75×3 mm-2.6 μm); Mobile Phase A: 0.1% TFA in water; Mobile Phase B: Acetonitrile; Gradient: 5% B to 40% B over 4 min, Flow: 1.0 mL/min; 40% B to 100% B up to 4.6 min, Flow: 1.5 mL/min; hold till 4.7 min; 4.7 min to 5.0 min 5% B, Flow: 1.5 mL/min; Detection: MS and UV (220 nm).

Method G: Column-Kinetex XB-C18 (75×3 mm-2.6 μm); Mobile Phase A: 10 mM NH4COOH in water; Mobile Phase B: Acetonitrile; Gradient: 20% B to 100% B over 4 min, Flow: 1.0 mL/min; hold till 4.6 min then 4.7 to 5.0 min 20% B Flow: 0.7 mL/min; Detection: MS and UV (220 nm).

Example 208

3-(4-Fluoro-1-oxo-5-(4-((3-phenylazetidin-1-yl)methyl)pyridin-2-yl)isoindolin-2-yl)piperidine-2,6-dione

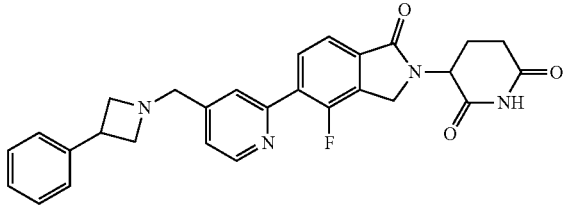

(208)

Step 1: (2-(Trimethylstannyl)pyridin-4-yl)methanol

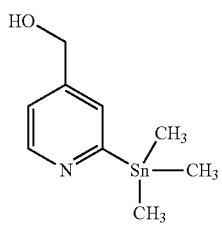

A stirred solution of (2-chloropyridin-4-yl)methanol (200 mg, 1.393 mmol) and hexamethylditin (0.433 mL, 2.090 mmol) in toluene (10 mL) was purged with argon for five minutes followed by the addition of [1,1'-bis(di-tert-butylphosphino)ferrocene] dichloropalladium(II) (45.4 mg, 0.070 mmol). The reaction mixture was stirred for 2 h at 100° C., cooled to room temperature and filtered. The filtrate was concentrated under reduced pressure to give (2-(trimethylstannyl)pyridin-4-yl)methanol (350 mg, 74% yield). LCMS (Method A): retention time 1.72 min, [M+H]+ 274.2.

Step 2: tert-Butyl (S)-5-amino-4-(4-fluoro-5-(4-(hydroxyethyl)pyridin-2-yl)-1-oxoisoindolin-2-yl)-5-oxopentanoate

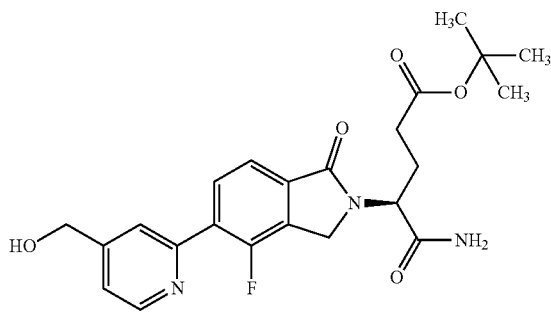 [SMILES: CC(C)(C)OC(=O)CC[C@@H](C(N)=O)N1Cc2c(ccc(-c3cc(CO)ccn3)c2F)C1=O]

A stirred solution of tert-butyl(S)-5-amino-4-(5-bromo-4-fluoro-1-oxoisoindolin-2-yl)-5-oxopentanoate (229 mg, 0.552 mmol) and (2-(trimethylstannyl)pyridin-4-yl)methanol (150 mg, 0.552 mmol) in dioxane (20 mL) was purged with argon for five minutes and bis(triphenylphosphine)palladium(II) chloride (38.7 mg, 0.055 mmol) was added. The reaction mixture was heated to 100° C. and stirred for 16 h. The reaction mixture was cooled to room temperature, filtered and the filtrate was concentrated under reduced pressure to give the crude product which was purified by flash chromatography (SiO₂, 80 g column, 0-100% B (B=15% EtOH in EtOAc, 0.5% TEA)/chloroform) to give tert-butyl(S)-5-amino-4-(4-fluoro-5-(4-(hydroxymethyl)pyridin-2-yl)-1-oxoisoindolin-2-yl)-5-oxopentanoate (180 mg, 66% yield). LCMS (Method A): retention time 1.04 min, [M+H]+ 444.3.

Step-3: tert-Butyl (S)-5-amino-4-(5-(4-(chloromethyl)pyridin-2-yl)-4-fluoro-1-oxoisoindolin-2-yl)-5-oxopentanoate

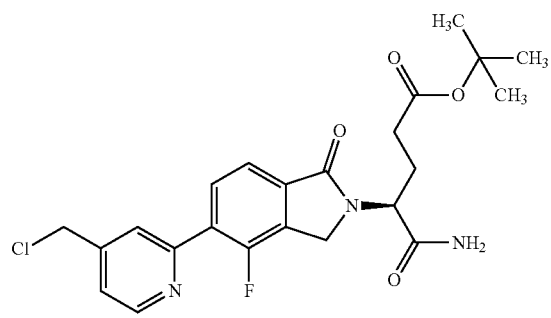 [SMILES: CC(C)(C)OC(=O)CC[C@@H](C(N)=O)N1Cc2c(ccc(-c3cc(CCl)ccn3)c2F)C1=O]

To a stirred solution of tert-butyl(S)-5-amino-4-(4-fluoro-5-(4-(hydroxymethyl)pyridin-2-yl)-1-oxoisoindolin-2-yl)-5-oxopentanoate (0.180 g, 0.406 mmol) in dichloromethane (10 mL), SOCl₂ (0.089 mL, 1.218 mmol) was added at 0° C. The reaction mixture was stirred at 25° C. for 1 h and concentrated under reduced pressure to give tert-butyl(S)-5-amino-4-(5-(4-(chloromethyl)pyridin-2-yl)-4-fluoro-1-oxoisoindolin-2-yl)-5-oxopentanoate (0.175 g, 74.7% yield). LCMS (Method A): retention time 1.48 min, [M+H]+ 462.3.

Step 4: 3-(5-(4-(Chloromethyl)pyridin-2-yl)-4-fluoro-1-oxoisoindolin-2-yl)piperidine-2,6-dione

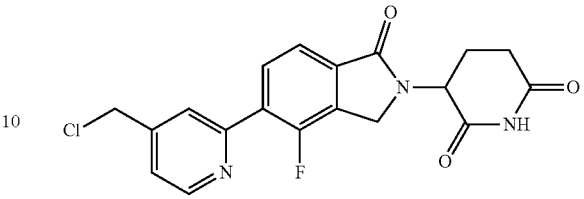

To a stirred solution of tert-butyl(S)-5-amino-4-(5-(4-(chloromethyl)pyridin-2-yl)-4-fluoro-1-oxoisoindolin-2-yl)-5-oxopentanoate (175 mg, 0.379 mmol) in acetic acid (2 mL), benzene sulfonic acid (120 mg, 0.758 mmol) was added. The reaction mixture was heated to 120° C. and stirred for 2 h. Volatiles were removed under reduced pressure to give 3-(5-(4-(chloromethyl)pyridin-2-yl)-4-fluoro-1-oxoisoindolin-2-yl)piperidine-2,6-dione (130 mg, 66% yield). LCMS (Method A): retention time 1.12 min, [M+H]+ 388.3.

Step 5: 3-(4-Fluoro-1-oxo-5-(4-((3-phenylazetidin-1-yl)methyl)pyridin-2-yl)isoindolin-2-yl)piperidine-2,6-dione To a stirred solution of 3-(5-(4-(chloromethyl)pyridin-2-yl)-4-fluoro-1-oxoisoindolin-2-yl)piperidine-2,6-dione (0.080 g, 0.206 mmol) and 3-phenylazetidine HCl (0.082 g, 0.619 mmol) in DMF (2 mL), DIPEA (0.216 mL, 1.238 mmol) was added at 25° C. The reaction mixture was heated to 80° C. and stirred for 3 h. Volatiles were removed under reduced pressure and the resulting crude product was purified via preparative HPLC with the following conditions: Column: Gemini NX C18 (250 mm×21 mm ID, 5 μm) Mobile phase A=10 mM Ammonium acetate in water pH 4.5 Mobile phase B=Acetonitrile:MeOH (1:1) Flow 19 mL/min gradient: Time: 20-70% of B over 20 minutes. The fractions were lyophilized to dryness to give the 3-(4-fluoro-1-oxo-5-(4-((3-phenylazetidin-1-yl)methyl)pyridin-2-yl)isoindolin-2-yl)piperidine-2,6-dione (23 mg, 22% yield). LCMS (Method G): retention time 1.60 min, [M+H]+ 485.1; ¹H NMR (400 MHz, DMSO-d6) δ 11.03 (br s, 1H), 8.69 (d, J=5.0 Hz, 1H), 8.09 (t, J=7.3 Hz, 1H), 7.83 (s, 1H), 7.71 (d, J=8.0 Hz, 1H), 7.44-7.28 (m, 5H), 7.25-7.20 (m, 1H), 5.16 (dd, J=13.1, 5.0 Hz, 1H), 4.76-4.38 (m, 2H), 3.79 (s, 2H), 3.75-3.63 (m, 3H), 3.22 (br t, J=5.3 Hz, 2H), 3.02-2.90 (m, 1H), 2.66-2.60 (m, 1H), 2.43 (br d, J=4.5 Hz, 1H), 2.11-2.02 (m, 1H).

Biological Assays

The pharmacological properties of the compounds of this invention may be confirmed by a number of biological assays. The exemplified biological assays, which follow, have been carried out with compounds of the invention.

Helios Cellular Degradation Assay

Jurkat cells were plated at 80,000 cells/well in 40 μL RPMI+10% FBS in a 384 well cell culture plate prior to using acoustic dispensing technology for adding compound of interest. Cell cultures were incubated for 72 h at 37° C. and 5% CO₂. In order to facilitate analysis, cell cultures were spun down at 200 rpm for 5 min and the supernatant was discarded. After shaking the plate to dislodge the cell pellet, cells were resuspended in 50 µL of Fixation Buffer (eBioScience FoxP3 buffer set 0000) for 60 min at room temperature. After centrifuging and discarding the supernatant, cells were permeabilized with 50 µL of Permeabilization buffer (eBioScience FoxP3 buffer set 00-5523-00) for 10 min at room temperature. Following permeabilization, cells were spun down and the supernatant was replaced with 20 µL fluorescently labelled antibodies against Helios and Ikaros or corresponding Isotype controls in 1× Permeabilization buffer (Ikaros-Alexa488 [Biolegend, Cat #368408, 1:50], Helios-PE [CST, Cat #29360, 1:50]) and staining reactions were incubated for 1 h at room temperature; protected from light. Subsequently, 30 µL of 1× Permeabilization buffer was added prior to centrifuging the cells and discarding the supernatant. Stained cells were resuspended in 25 µL of flow cytometry staining buffer (PBS+0.2% BSA) and analyzed using an Intellicyt Ique Plus flow cytometer.

TABLE 10

Helios and Ikaros degradation activity

| Example Number | Helios $DC_{50}$ (µM) | Helios $D_{max}$ (%) | Ikaros $DC_{50}$ (µM) | Ikaros $D_{max}$ (%) |
|---|---|---|---|---|
| 1 | 0.025 | 84 | >10 | 9 |
| 2 | 0.011 | 92 | >10 | 16 |
| 3 | 0.038 | 87 | >10 | 3 |
| 4 | 0.096 | 84 | >10 | 8 |
| 5 | 0.044 | 90 | >10 | 5 |
| 6 | 0.028 | 86 | >10 | 6 |
| 7 | 0.138 | 85 | >10 | 20 |
| 8 | 0.026 | 85 | >10 | 18 |
| 9 | 0.167 | 87 | >10 | 4 |
| 10 | 0.183 | 67 | >10 | 9 |
| 11 | 0.573 | 59 | >10 | 7 |
| 12 | >10 | 37 | >10 | 16 |
| 13 | 0.200 | 67 | >10 | 8 |
| 14 | 0.036 | 80 | >10 | 16 |
| 15 | >10 | 5 | >10 | 8 |
| 16 | 0.788 | 63 | >10 | 12 |
| 17 | >10 | 16 | >10 | 11 |
| 18 | >10 | 21 | >10 | 19 |
| 19 | 0.154 | 82 | >10 | 50 |
| 20 | 0.060 | 80 | >10 | 11 |
| 21 | >10 | 35 | >10 | 4 |
| 22 | 0.537 | 67 | >10 | 33 |
| 23 | >10 | 22 | >10 | 14 |
| 24 | >10 | 3 | >10 | 11 |
| 25 | >10 | 0 | >10 | 0 |
| 26 | >10 | 6 | >10 | 15 |
| 27 | >10 | 36 | >10 | 7 |
| 28 | >10 | 17 | >10 | 13 |
| 29 | 7.511 | 55 | >10 | 6 |
| 30 | >10 | 46 | >10 | -1 |
| 31 | 0.268 | 81 | >10 | 20 |
| 32 | >10 | 35 | >10 | 23 |
| 33 | >10 | 50 | >10 | 2 |
| 34 | >10 | 26 | >10 | 9 |
| 35 | 0.869 | 63 | >10 | 30 |
| 36 | >10 | 11 | >10 | 14 |
| 37 | >10 | 24 | >10 | 10 |
| 38 | 0.087 | 68 | >10 | 6 |
| 39 | 0.444 | 58 | >10 | 6 |
| 40 | >10 | 9 | >10 | 8 |
| 41 | 0.727 | 80 | >10 | 24 |
| 42 | >10 | 3 | >10 | 7 |
| 43 | >10 | 10 | >10 | 3 |
| 44 | >10 | 36 | >10 | 12 |
| 45 | >10 | 43 | >10 | 6 |
| 46 | 0.018 | 83 | >10 | 6 |
| 47 | 0.017 | 79 | >10 | 8 |
| 48 | 0.032 | 72 | >10 | 6 |
| 49 | >10 | 29 | >10 | 3 |
| 50 | 0.022 | 78 | >10 | 12 |
| 51 | 0.064 | 70 | >10 | 11 |
| 52 | 0.300 | 67 | >10 | 10 |
| 53 | 0.231 | 77 | >10 | 21 |
| 54 | 0.016 | 83 | >10 | 12 |
| 55 | 0.009 | 91 | >10 | 10 |
| 56 | 0.013 | 88 | >10 | 18 |
| 57 | >10 | 32 | >10 | 0 |
| 58 | 0.009 | 88 | >10 | 22 |
| 59 | 0.082 | 79 | >10 | 20 |
| 60 | 0.548 | 63 | >10 | 19 |
| 61 | 0.012 | 83 | >10 | 5 |
| 62 | 0.045 | 80 | >10 | 5 |
| 63 | 0.014 | 80 | >10 | 13 |
| 64 | 0.036 | 73 | >10 | 1 |
| 65 | 0.055 | 70 | >10 | 7 |
| 66 | >10 | 26 | >10 | 7 |
| 67 | >10 | 41 | >10 | 6 |
| 68 | 0.192 | 71 | >10 | 15 |
| 69 | 0.783 | 57 | >10 | 0 |
| 70 | 0.019 | 79 | >10 | 10 |
| 71 | >10 | 17 | >10 | 8 |
| 72 | 0.013 | 90 | >10 | 13 |
| 73 | 0.045 | 62 | >10 | 13 |
| 74 | 2.500 | 53 | >10 | 16 |
| 75 | 0.014 | 94 | >10 | 10 |
| 76 | 0.006 | 98 | >10 | 12 |
| 77 | 0.012 | 85 | >10 | 12 |
| 78 | >10 | 49 | >10 | 0 |
| 79 | >10 | 26 | >10 | 8 |
| 80 | 0.035 | 99 | >10 | 12 |
| 81 | 0.078 | 64 | >10 | 26 |
| 82 | 0.009 | 89 | >10 | 17 |
| 83 | 0.007 | 91 | >10 | 20 |
| 84 | 0.040 | 69 | >10 | 4 |
| 85 | >10 | 20 | >10 | 7 |
| 86 | 0.019 | 91 | >10 | 20 |
| 87 | 0.029 | 100 | >10 | 12 |
| 88 | 0.072 | 102 | >10 | 27 |
| 89 | 0.103 | 71 | >10 | 8 |
| 90 | 0.213 | 61 | >10 | 17 |
| 91 | 3.529 | 60 | >10 | 4 |
| 92 | 0.209 | 92 | >10 | 11 |
| 93 | 0.009 | 103 | >10 | 23 |
| 94 | 0.035 | 74 | >10 | 11 |
| 95 | 0.034 | 94 | >10 | 17 |
| 96 | 0.019 | 94 | >10 | 25 |
| 97 | 0.008 | 90 | >10 | 11 |
| 98 | 0.006 | 91 | >10 | 8 |
| 99 | 0.419 | 65 | >10 | 6 |
| 100 | 6.131 | 55 | >10 | 6 |
| 101 | 0.059 | 89 | >10 | 22 |
| 102 | 0.011 | 97 | >10 | 10 |
| 103 | 0.036 | 95 | >10 | 1 |
| 104 | >10 | 44 | >10 | 1 |
| 105 | 0.264 | 79 | >10 | 5 |
| 106 | 0.072 | 79 | >10 | 12 |
| 107 | 0.494 | 80 | >10 | 15 |
| 108 | 0.045 | 84 | >10 | 15 |
| 109 | 0.048 | 75 | >10 | 15 |
| 110 | 0.048 | 71 | >10 | 7 |
| 111 | 0.137 | 75 | >10 | 10 |
| 112 | 0.921 | 74 | >10 | 2 |
| 113 | 0.287 | 81 | >10 | 8 |
| 114 | 0.063 | 83 | >10 | 2 |
| 115 | 0.528 | 78 | >10 | 6 |
| 116 | 0.025 | 88 | >10 | 12 |
| 117 | 0.053 | 77 | >10 | 3 |
| 118 | 0.011 | 90 | >10 | 12 |
| 119 | 2.357 | 53 | >10 | 3 |
| 120 | 0.085 | 84 | >10 | 3 |
| 121 | 0.024 | 77 | >10 | 19 |
| 122 | 0.014 | 88 | >10 | 4 |
| 123 | 0.007 | 92 | >10 | 8 |

TABLE 10-continued

Helios and Ikaros degradation activity

| Example Number | Helios DC$_{50}$ (μM) | Helios D$_{max}$ (%) | Ikaros DC$_{50}$ (μM) | Ikaros D$_{max}$ (%) |
|---|---|---|---|---|
| 124 | 0.058 | 95 | >10 | 11 |
| 125 | 0.016 | 93 | >10 | 8 |
| 126 | 0.082 | 99 | >10 | 22 |
| 127 | 0.035 | 84 | >10 | 6 |
| 128 | 0.093 | 94 | >10 | 28 |
| 129 | 0.232 | 74 | >10 | 2 |
| 130 | 0.244 | 56 | >10 | 13 |
| 131 | 0.014 | 83 | >10 | 9 |
| 132 | >10 | 28 | >10 | 13 |
| 133 | 0.075 | 84 | >10 | 7 |
| 134 | 0.016 | 95 | >10 | 19 |
| 135 | 1.308 | 60 | >10 | 4 |
| 136 | 0.084 | 62 | >10 | 0 |
| 137 | 0.098 | 67 | >10 | 8 |
| 138 | 0.037 | 82 | >10 | 18 |
| 139 | 0.025 | 91 | >10 | 3 |
| 140 | 0.012 | 76 | >10 | 22 |
| 141 | 0.046 | 82 | >10 | 20 |
| 142 | 0.088 | 83 | 0.897 | 52 |
| 143 | 0.040 | 62 | >10 | 1 |
| 144 | 2.021 | 57 | >10 | 11 |
| 145 | 0.067 | 93 | >10 | 11 |
| 146 | >10 | 3 | >10 | 5 |
| 147 | 0.226 | 74 | >10 | 4 |
| 148 | 0.238 | 75 | >10 | 9 |
| 149 | >10 | 17 | >10 | 6 |
| 150 | >10 | 45 | >10 | 17 |
| 151 | >10 | 23 | >10 | 1 |
| 152 | 0.850 | 55 | >10 | 7 |
| 153 | 4.706 | 58 | >10 | 7 |
| 154 | 3.257 | 54 | >10 | 6 |
| 155 | 1.579 | 57 | >10 | 0 |
| 156 | 1.827 | 56 | >10 | 11 |
| 157 | >10 | 38 | >10 | 8 |
| 158 | 0.256 | 74 | >10 | 3 |
| 159 | 0.136 | 76 | >10 | 25 |
| 160 | 0.359 | 70 | >10 | 30 |
| 161 | 0.067 | 83 | >10 | 17 |
| 162 | 1.087 | 63 | >10 | 2 |
| 163 | 1.023 | 56 | >10 | 31 |
| 164 | 0.062 | 77 | >10 | 10 |
| 165 | 0.056 | 95 | >10 | 14 |
| 166 | 7.860 | 52 | >10 | 7 |
| 167 | >10 | 41 | >10 | 12 |
| 168 | 0.309 | 77 | >10 | 20 |
| 169 | 0.195 | 79 | >10 | 16 |
| 170 | >10 | 22 | >10 | 2 |
| 171 | 0.317 | 80 | >10 | 4 |
| 172 | 0.075 | 90 | >10 | 12 |
| 173 | 0.073 | 86 | >10 | 0 |
| 174 | 5.872 | 54 | >10 | 20 |
| 175 | 0.078 | 78 | >10 | 7 |
| 176 | 1.124 | 65 | >10 | 30 |
| 177 | >10 | 43 | >10 | 12 |
| 178 | 0.131 | 82 | >10 | 15 |
| 179 | 0.212 | 78 | >10 | 4 |
| 180 | 0.352 | 87 | >10 | 13 |
| 181 | 0.499 | 83 | >10 | 10 |
| 182 | 0.316 | 79 | >10 | 23 |
| 183 | 0.167 | 76 | >10 | 10 |
| 184 | 6.051 | 54 | >10 | 14 |
| 185 | 0.421 | 62 | >10 | 2 |
| 194 | 10.00 | 5.16 | 10.00 | 0.04 |
| 204 | 10.00 | 2.42 | 10.00 | 15.52 |
| 205 | 0.00 | 84.96 | 10.00 | 8.15 |

Biological Assays

The pharmacological properties of the compounds of this invention may be confirmed by a number of biological assays. The exemplified biological assays, which follow, have been carried out with compounds of the invention.

Helios Cellular Degradation Assay

Jurkat cells were plated at 80,000 cells/well in 40 μL RPMI+10% FBS in a 384 well cell culture plate prior to using acoustic dispensing technology for adding compound of interest. Cell cultures were incubated for 72 h at 37° C. and 5% $CO_2$. In order to facilitate analysis, cell cultures were spun down at 200 rpm for 5 min and the supernatant was discarded. After shaking the plate to dislodge the cell pellet, cells were resuspended in 50 μL of Fixation Buffer (eBioScience FoxP3 buffer set 00-5523-00) for 60 min at room temperature. After centrifuging and discarding the supernatant, cells were permeabilized with 50 μL of Permeabilization buffer (eBioScience FoxP3 buffer set 00-5523-00) for 10 min at room temperature. Following permeabilization, cells were spun down and the supernatant was replaced with 20 μL fluorescently labelled antibodies against Helios and Ikaros or corresponding Isotype controls in 1× Permeabilization buffer (Ikaros-Alexa488 [Biolegend, Cat #368408, 1:50], Helios-PE [CST, Cat #29360, 1:50]) and staining reactions were incubated for 1 h at room temperature; protected from light. Subsequently, 30 μL of 1× Permeabilization buffer was added prior to centrifuging the cells and discarding the supernatant. Stained cells were resuspended in 25 μL of flow cytometry staining buffer (PBS+0.2% BSA) and analyzed using an Intellicyt Ique Plus flow cytometer.

TABLE 4

Helios and Ikaros degradation activity

| Ex. No. | Helios DC$_{50}$ (μM) | Helios D$_{max}$ (%) | Ikaros DC$_{50}$ (μM) | Ikaros D$_{max}$ (%) |
|---|---|---|---|---|
| 1 | 0.025 | 84 | >10 | 9 |
| 2 | 0.011 | 92 | >10 | 16 |
| 3 | 0.038 | 87 | >10 | 3 |
| 4 | 0.096 | 84 | >10 | 8 |
| 5 | 0.044 | 90 | >10 | 5 |
| 6 | 0.028 | 86 | >10 | 6 |
| 7 | 0.138 | 85 | >10 | 20 |
| 8 | 0.026 | 85 | >10 | 18 |
| 9 | 0.167 | 87 | >10 | 4 |
| 10 | 0.183 | 67 | >10 | 9 |
| 11 | 0.573 | 59 | >10 | 7 |
| 12 | >10 | 37 | >10 | 16 |
| 13 | 0.200 | 67 | >10 | 8 |
| 14 | 0.036 | 80 | >10 | 16 |
| 15 | >10 | 5 | >10 | 8 |
| 16 | 0.788 | 63 | >10 | 12 |
| 17 | >10 | 16 | >10 | 11 |
| 18 | >10 | 21 | >10 | 19 |
| 19 | 0.154 | 82 | >10 | 50 |
| 20 | 0.060 | 80 | >10 | 11 |
| 21 | >10 | 35 | >10 | 4 |
| 22 | 0.537 | 67 | >10 | 33 |
| 23 | >10 | 22 | >10 | 14 |
| 24 | >10 | 3 | >10 | 11 |
| 25 | >10 | 0 | >10 | 0 |
| 26 | >10 | 6 | >10 | 15 |
| 27 | >10 | 36 | >10 | 7 |
| 28 | >10 | 17 | >10 | 13 |
| 29 | 7.511 | 55 | >10 | 6 |
| 30 | >10 | 46 | >10 | −1 |
| 31 | 0.268 | 81 | >10 | 20 |
| 32 | >10 | 35 | >10 | 23 |
| 33 | >10 | 50 | >10 | 2 |
| 34 | >10 | 26 | >10 | 9 |
| 35 | 0.869 | 63 | >10 | 30 |
| 36 | >10 | 11 | >10 | 14 |
| 37 | >10 | 24 | >10 | 10 |

TABLE 4-continued

Helios and Ikaros degradation activity

| Ex. No. | Helios DC$_{50}$ (μM) | Helios D$_{max}$ (%) | Ikaros DC$_{50}$ (μM) | Ikaros D$_{max}$ (%) |
|---|---|---|---|---|
| 38 | 0.087 | 68 | >10 | 6 |
| 39 | 0.444 | 58 | >10 | 6 |
| 40 | >10 | 9 | >10 | 8 |
| 41 | 0.727 | 80 | >10 | 24 |
| 42 | >10 | 3 | >10 | 7 |
| 43 | >10 | 10 | >10 | 3 |
| 44 | >10 | 36 | >10 | 12 |
| 45 | >10 | 43 | >10 | 6 |
| 46 | 0.018 | 83 | >10 | 6 |
| 47 | 0.017 | 79 | >10 | 8 |
| 48 | 0.032 | 72 | >10 | 6 |
| 49 | >10 | 29 | >10 | 3 |
| 50 | 0.022 | 78 | >10 | 12 |
| 51 | 0.064 | 70 | >10 | 11 |
| 52 | 0.300 | 67 | >10 | 10 |
| 53 | 0.231 | 77 | >10 | 21 |
| 54 | 0.016 | 83 | >10 | 12 |
| 55 | 0.009 | 91 | >10 | 10 |
| 56 | 0.013 | 88 | >10 | 18 |
| 57 | >10 | 32 | >10 | 0 |
| 58 | 0.009 | 88 | >10 | 22 |
| 59 | 0.082 | 79 | >10 | 20 |
| 60 | 0.548 | 63 | >10 | 19 |
| 61 | 0.012 | 83 | >10 | 5 |
| 62 | 0.045 | 80 | >10 | 5 |
| 63 | 0.014 | 80 | >10 | 13 |
| 64 | 0.036 | 73 | >10 | 1 |
| 65 | 0.055 | 70 | >10 | 7 |
| 66 | >10 | 26 | >10 | 7 |
| 67 | >10 | 41 | >10 | 6 |
| 68 | 0.192 | 71 | >10 | 15 |
| 69 | 0.783 | 57 | >10 | 0 |
| 70 | 0.019 | 79 | >10 | 10 |
| 71 | >10 | 17 | >10 | 8 |
| 72 | 0.013 | 90 | >10 | 13 |
| 73 | 0.045 | 62 | >10 | 13 |
| 74 | 2.500 | 53 | >10 | 16 |
| 75 | 0.014 | 94 | >10 | 10 |
| 76 | 0.006 | 98 | >10 | 12 |
| 77 | 0.012 | 85 | >10 | 12 |
| 78 | >10 | 49 | >10 | 0 |
| 79 | >10 | 26 | >10 | 8 |
| 80 | 0.035 | 99 | >10 | 12 |
| 81 | 0.078 | 64 | >10 | 26 |
| 82 | 0.009 | 89 | >10 | 17 |
| 83 | 0.007 | 91 | >10 | 20 |
| 84 | 0.040 | 69 | >10 | 4 |
| 85 | >10 | 20 | >10 | 7 |
| 86 | 0.019 | 91 | >10 | 20 |
| 87 | 0.029 | 100 | >10 | 12 |
| 88 | 0.072 | 102 | >10 | 27 |
| 89 | 0.103 | 71 | >10 | 8 |
| 90 | 0.213 | 61 | >10 | 17 |
| 91 | 3.529 | 60 | >10 | 4 |
| 92 | 0.209 | 92 | >10 | 11 |
| 93 | 0.009 | 103 | >10 | 23 |
| 94 | 0.035 | 74 | >10 | 11 |
| 95 | 0.034 | 94 | >10 | 17 |
| 96 | 0.019 | 94 | >10 | 25 |
| 97 | 0.008 | 90 | >10 | 11 |
| 98 | 0.006 | 91 | >10 | 8 |
| 99 | 0.419 | 65 | >10 | 6 |
| 100 | 6.131 | 55 | >10 | 6 |
| 101 | 0.059 | 89 | >10 | 22 |
| 102 | 0.011 | 97 | >10 | 10 |
| 103 | 0.036 | 95 | >10 | 1 |
| 104 | >10 | 44 | >10 | 1 |
| 105 | 0.264 | 79 | >10 | 5 |
| 106 | 0.072 | 79 | >10 | 12 |
| 107 | 0.494 | 80 | >10 | 15 |
| 108 | 0.045 | 84 | >10 | 15 |
| 109 | 0.048 | 75 | >10 | 15 |
| 110 | 0.048 | 71 | >10 | 7 |
| 111 | 0.137 | 75 | >10 | 10 |
| 112 | 0.921 | 74 | >10 | 2 |
| 113 | 0.287 | 81 | >10 | 8 |
| 114 | 0.063 | 83 | >10 | 2 |
| 115 | 0.528 | 78 | >10 | 6 |
| 116 | 0.025 | 88 | >10 | 12 |
| 117 | 0.053 | 77 | >10 | 3 |
| 118 | 0.011 | 90 | >10 | 12 |
| 119 | 2.357 | 53 | >10 | 3 |
| 120 | 0.085 | 84 | >10 | 3 |
| 121 | 0.024 | 77 | >10 | 19 |
| 122 | 0.014 | 88 | >10 | 4 |
| 123 | 0.007 | 92 | >10 | 8 |
| 124 | 0.058 | 95 | >10 | 11 |
| 125 | 0.016 | 93 | >10 | 8 |
| 126 | 0.082 | 99 | >10 | 22 |
| 127 | 0.035 | 84 | >10 | 6 |
| 128 | 0.093 | 94 | >10 | 28 |
| 129 | 0.232 | 74 | >10 | 2 |
| 130 | 0.244 | 56 | >10 | 13 |
| 131 | 0.014 | 83 | >10 | 9 |
| 132 | >10 | 28 | >10 | 13 |
| 133 | 0.075 | 84 | >10 | 7 |
| 134 | 0.016 | 95 | >10 | 19 |
| 135 | 1.308 | 60 | >10 | 4 |
| 136 | 0.084 | 62 | >10 | 0 |
| 137 | 0.098 | 67 | >10 | 8 |
| 138 | 0.037 | 82 | >10 | 18 |
| 139 | 0.025 | 91 | >10 | 3 |
| 140 | 0.012 | 76 | >10 | 22 |
| 141 | 0.046 | 82 | >10 | 20 |
| 142 | 0.088 | 83 | 0.897 | 52 |
| 143 | 0.040 | 62 | >10 | 1 |
| 144 | 2.021 | 57 | >10 | 11 |
| 145 | 0.067 | 93 | >10 | 11 |
| 146 | >10 | 3 | >10 | 5 |
| 147 | 0.226 | 74 | >10 | 4 |
| 148 | 0.238 | 75 | >10 | 9 |
| 149 | >10 | 17 | >10 | 6 |
| 150 | >10 | 45 | >10 | 17 |
| 151 | >10 | 23 | >10 | 1 |
| 152 | 0.850 | 55 | >10 | 7 |
| 153 | 4.706 | 58 | >10 | 7 |
| 154 | 3.257 | 54 | >10 | 6 |
| 155 | 1.579 | 57 | >10 | 0 |
| 156 | 1.827 | 56 | >10 | 11 |
| 157 | >10 | 38 | >10 | 8 |
| 158 | 0.256 | 74 | >10 | 3 |
| 159 | 0.136 | 76 | >10 | 25 |
| 160 | 0.359 | 70 | >10 | 30 |
| 161 | 0.067 | 83 | >10 | 17 |
| 162 | 1.087 | 63 | >10 | 2 |
| 163 | 1.023 | 56 | >10 | 31 |
| 164 | 0.062 | 77 | >10 | 10 |
| 165 | 0.056 | 95 | >10 | 14 |
| 166 | 7.860 | 52 | >10 | 7 |
| 167 | >10 | 41 | >10 | 12 |
| 168 | 0.309 | 77 | >10 | 20 |
| 169 | 0.195 | 79 | >10 | 16 |
| 170 | >10 | 22 | >10 | 2 |
| 171 | 0.317 | 80 | >10 | 4 |
| 172 | 0.075 | 90 | >10 | 12 |
| 173 | 0.073 | 86 | >10 | 0 |
| 174 | 5.872 | 54 | >10 | 20 |
| 175 | 0.078 | 78 | >10 | 7 |
| 176 | 1.124 | 65 | >10 | 30 |
| 177 | >10 | 43 | >10 | 12 |
| 178 | 0.131 | 82 | >10 | 15 |
| 179 | 0.212 | 78 | >10 | 4 |
| 180 | 0.352 | 87 | >10 | 13 |
| 181 | 0.499 | 83 | >10 | 10 |
| 182 | 0.316 | 79 | >10 | 23 |
| 183 | 0.167 | 76 | >10 | 10 |

TABLE 4-continued

Helios and Ikaros degradation activity

| Ex. No. | Helios DC$_{50}$ (μM) | Helios D$_{max}$ (%) | Ikaros DC$_{50}$ (μM) | Ikaros D$_{max}$ (%) |
|---|---|---|---|---|
| 184 | 6.051 | 54 | >10 | 14 |
| 185 | 0.421 | 62 | >10 | 2 |
| 186 | 0.23 | 62 | >10 | 8 |
| 187 | 0.024 | 84 | >10 | 6 |
| 188 | 0.027 | 76 | — | 16 |
| 189 | 0.011 | 80 | >10 | 16 |
| 190 | 0.076 | 71 | >10 | 16 |
| 191 | 3.2 | 52 | >10 | 3 |
| 192 | >10 | 41 | >10 | 16 |
| 193 | 0.12 | 60 | >10 | 14 |
| 194 | >10 | 5.2 | >10 | 3 |
| 196 | 0.045 | 78 | >10 | 7 |
| 197 | 0.042 | 75 | >10 | 20 |
| 198 | 0.042 | 75 | >10 | 18 |
| 199 | 0.13 | 60 | >10 | 3 |
| 202 | 0.19 | 69 | >10 | 22 |
| 203 | 0.44 | 69 | >10 | 20 |
| 204 | >10 | 2.4 | >10 | 4 |
| 205 | >10 | 2 | >10 | 6 |
| 206 | 0.74 | 66 | >10 | 9 |
| 208 | 0.003 | 88 | >10 | 13 |

What is claimed is:

1. A compound of Formula (I)

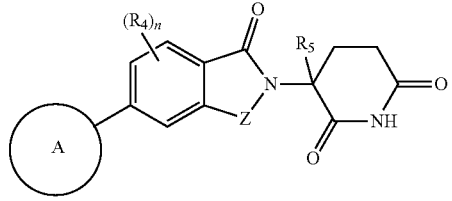

(I)

or a pharmaceutically acceptable salt thereof, wherein:
Z is $CR_6R_6$ or C=O;
Ring A is:

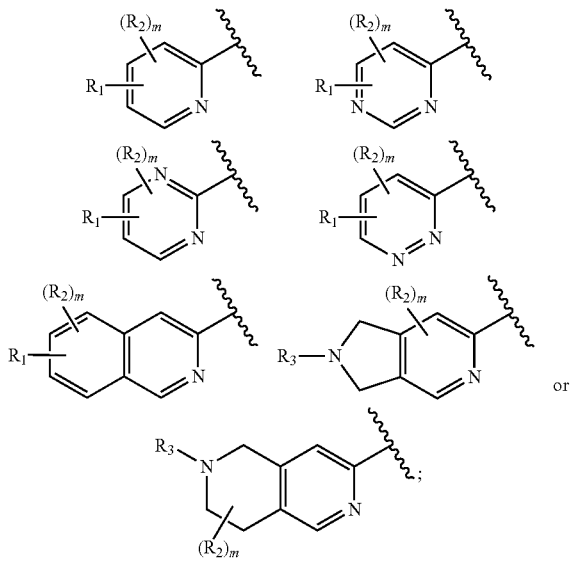

$R_1$ is $-(CR_zR_z)_{1-2}NR_{1a}R_{1b}$;
$R_{1a}$ is hydrogen, $C_{1-6}$ alkyl, $C_{1-4}$ fluoroalkyl, $C_{1-3}$ cyanoalkyl, $C_{1-6}$ hydroxyalkyl, $-(CH_2)_{1-3}O(C_{1-3}$ alkyl), $-(CH_2)_{1-3}S(O)_2(C_{1-3}$ alkyl), $-(CH_2)_{1-3}C(O)O(C_{1-3}$ alkyl), $-(CH_2)_{1-3}NR_xR_x$, $-(CH_2)_{1-3}C(O)NR_xR_x$, $-(CH_2)_{1-3}NR_xC(O)(C_{1-3}$ alkyl), $-C(O)(C_{1-3}$ alkyl), $-CH(phenyl)(C_{1-2}$ hydroxyalkyl), $-CR_xR_xCR_x(phenyl)_2$, $R_{1c}$, $-(CR_xR_x)_{1-3}R_{1c}$, $-(CR_xR_x)_{1-3}OR_{1c}$, or $-C(O)R_{1c}$;
$R_{1b}$ is hydrogen, $C_{1-3}$ alkyl, or $-CH_2$(phenyl);
or $R_{1a}$ and $R_{1b}$ along with the nitrogen atom to which they are attached, are joined together to form a cyclic group selected from azaspiro[2.5]octanyl, azepanyl, azetidinyl, azocanyl, diazepanyl, dioxidothiomorpholinyl, isoindolinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinonyl, piperidinyl, pyrrolidinyl, pyrrolidinonyl, and tetrahydroisoquinolinyl, each substituted with zero to 1 $R_{1d}$ and zero to 2 $R_{1e}$;
$R_{1c}$ is $C_{3-7}$ cycloalkyl, phenyl, oxetanyl, azetidinyl, furanyl, pyranyl, pyrrolyl, pyrrolidinyl, pyrrolidinonyl, pyrazolyl, imidazolyl, indazolyl, thiazolyl, piperidinyl, pyridinyl, tetrahydrofuranyl, tetrahydropyranyl, morpholinyl, dioxotetrahydrothiopyranyl, dioxidotetrahydrothiophenyl, benzo[d]thiazolyl, naphthalenyl, quinolinyl, or quinoxalinyl, each substituted with zero to 2 substituents independently selected from F, Cl, —CN, —OH, $C_{1-3}$ alkyl, $C_{1-3}$ fluoroalkyl, $C_{1-3}$ hydroxyalkyl, $C_{1-3}$ alkoxy, $C_{1-3}$ fluoroalkoxy, $-C(O)O(C_{1-3}$ alkyl), $-NR_yR_y$, $-S(O)_2(C_{1-3}$ alkyl), $-S(O)_2NR_xR_x$, $-CH_2$(phenyl), $-NO_2$, $C_{3-6}$ cycloalkyl, imidazolyl, and phenyl;
$R_{1d}$ is $C_{1-4}$ alkyl, $C_{1-2}$ fluoroalkyl, $C_{1-3}$ alkoxy, $-NR_yR_y$, $-NR_xC(O)(C_{1-3}$ alkyl), $-C(O)(C_{1-3}$ alkyl), $-C(O)NR_yR_y$, $-CH_2$(phenyl), $-CH_2$(methylpyrrolidinyl), $-CH_2$(benzo[d][1,3]dioxolyl), $-CH(phenyl)_2$, $-C(O)(tetrahydrofuranyl)$, $-C(O)(furanyl)$, $-S(O)_2$(methylphenyl), phenyl, methylphenyl, aminophenyl, piperidinyl, pyrazinyl, pyridinyl, pyrimidinyl, pyrrolidinyl, or dihydrobenzo[d]imidazolonyl;
$R_{1e}$ is $-CH_3$;
each $R_2$ is independently halogen, —CN, —NRR, $C_{1-3}$ alkyl, $C_{1-3}$ fluoroalkyl, $C_{1-3}$ alkoxy, $C_{1-3}$ fluoroalkoxy, or phenyl;
R is H or $C_{1-3}$ alkyl;
$R_3$ is $R_{1a}$;
each $R_4$ is independently halogen, —CN, $C_{1-3}$ alkyl, $C_{1-3}$ fluoroalkyl, $C_{1-3}$ alkoxy, or $C_{1-3}$ fluoroalkoxy;
each $R_4$ is independently halogen, —CN, —OH, $C_{1-3}$ alkyl, $C_{1-3}$ fluoroalkyl, $C_{1-3}$ alkoxy, $C_{1-3}$ fluoroalkoxy, or $-NR_yR_y$;
$R_5$ is hydrogen, F, or $C_{1-3}$ alkyl;
each $R_6$ is independently hydrogen or $C_{1-3}$ alkyl;
each $R_x$ is independently H or $-CH_3$;
each $R_y$ is independently H or $C_{1-4}$ alkyl;
each $R_z$ is independently H or $-CH_3$; or two $R_z$ attached to the same carbon atom, form a 3- to 6-membered carbocyclic ring;
m is zero, 1, or 2; and
n is zero, 1, 2, or 3.

2. The compound according to claim 1 or a pharmaceutically acceptable salt thereof, wherein:
$R_{1a}$ is hydrogen, $C_{1-6}$ alkyl, $C_{1-3}$ fluoroalkyl, $C_{1-2}$ cyanoalkyl, $C_{1-4}$ hydroxyalkyl, $-(CH_2)_{1-3}OCH_3$, —(CH$_2$)$_{1-3}$S(O)$_2$(C$_{1-2}$ alkyl), —(CH$_2$)$_{1-2}$C(O)O(C$_{1-3}$ alkyl), —(CH$_2$)$_{1-3}$NR$_x$R$_x$, —(CH$_2$)$_{1-2}$C(O)NR$_x$R$_x$, —(CH$_2$)$_{1-3}$NR$_x$C(O)(C$_{1-3}$ alkyl), —C(O)(C$_{1-3}$ alkyl), —CH(phenyl)(C$_{1-2}$ hydroxyalkyl), —CR$_x$R$_x$CR$_x$(phenyl)$_2$, R$_{1c}$, —(CR$_x$R$_x$)$_{1-3}$R$_{1c}$, —(CR$_x$R$_x$)$_{1-3}$OR$_{1c}$, or —C(O)R$_{1c}$;

or R$_{1a}$ and R$_{1b}$ along with the nitrogen atom to which they are attached, are joined together to form a cyclic group selected from azaspiro[2.5]octanyl, azepanyl, azetidinyl, azocanyl, diazepanyl, dioxidothiomorpholinyl, isoindolinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinyl, pyrrolidinyl, and tetrahydroisoquinolinyl, each substituted with zero to 1 R$_{1d}$ and zero to 2 R$_{1e}$;

R$_{1c}$ is C$_{3-6}$ cycloalkyl, phenyl, oxetanyl, furanyl, pyrrolyl, pyrrolidinyl, pyrrolidinonyl, imidazolyl, indazolyl, thiazolyl, piperidinyl, pyridinyl, tetrahydrofuranyl, tetrahydropyranyl, morpholinyl, dioxotetrahydrothiopyranyl, dioxidotetrahydrothiophenyl, benzo[d]thiazolyl, naphthalenyl, quinolinyl, or quinoxalinyl, each substituted with zero to 2 substituents independently selected from F, Cl, —CN, —OH, C$_{1-2}$ alkyl, C$_{1-2}$ fluoroalkyl, C$_{1-2}$ hydroxyalkyl, C$_{1-2}$ alkoxy, C$_{1-2}$ fluoroalkoxy, —C(O)O(C$_{1-2}$ alkyl), —NR$_x$R$_y$, —S(O)$_2$(C$_{1-2}$ alkyl), —S(O)$_2$NR$_x$R$_x$, —CH$_2$(phenyl), —NO$_2$, C$_{3-6}$ cycloalkyl, imidazolyl, and phenyl;

R$_{1d}$ is C$_{1-3}$ alkyl, C$_{1-2}$ fluoroalkyl, C$_{1-3}$ alkoxy, —NR$_x$R$_y$, —NR$_x$C(O)(C$_{1-2}$ alkyl), —C(O)(C$_{1-2}$ alkyl), —C(O)NR$_y$R$_y$, —CH$_2$(phenyl), —CH$_2$(methylpyrrolidinyl), —CH$_2$(benzo[d][1,3]dioxolyl), —CH(phenyl)$_2$, —C(O)(tetrahydrofuranyl), —C(O)(furanyl), —S(O)$_2$(methylphenyl), phenyl, methylphenyl, aminophenyl, piperidinyl, pyrazinyl, pyridinyl, pyrimidinyl, pyrrolidinyl, or dihydrobenzo[d]imidazolonyl;

each R$_4$ is independently F, Cl, —CN, —CH$_3$, —CHF$_2$, —CF$_3$, —OCH$_3$, or —OCF$_3$;

R$_5$ is hydrogen, F, or —CH$_3$;

m is zero or 1; and n is zero, 1, or 2.

3. The compound according to claim 1 or a pharmaceutically acceptable salt thereof, wherein Ring A is:

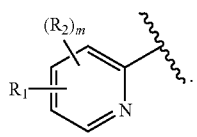

4. The compound according to claim 1 or a pharmaceutically acceptable salt thereof, having the structure:

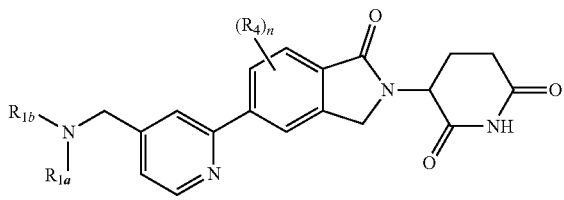

wherein:

R$_{1a}$ is hydrogen, C$_{1-6}$ alkyl, —CH$_2$CH$_2$CF$_3$, —CH$_2$CN, —CH$_2$CH$_2$OH, —CH(CH$_3$)CH$_2$OH, —CH$_2$CH$_2$CH$_2$OH, —CH(CH$_3$)CH$_2$CH$_2$OH, —CH$_2$CH$_2$OCH$_3$, —CH$_2$CH$_2$C(O)OCH$_3$, —CH$_2$CH$_2$N(CH$_3$)$_2$, —CH$_2$C(O)NH$_2$, —CH$_2$C(O)N(CH$_3$)$_2$, —CH$_2$CH$_2$C(O)NH$_2$, —CH$_2$CH$_2$NHC(O)CH$_3$, —CH(phenyl)(CH$_2$CH$_2$OH), —CH$_2$CH(phenyl)$_2$, R$_{1c}$, —CR$_x$R$_x$R$_{1c}$, —CH$_2$CH$_2$R$_{1c}$, —CH$_2$CH$_2$CH$_2$R$_{1c}$, or —CH$_2$CH$_2$OR$_{1c}$;

or R$_{1a}$ and R$_{1b}$ along with the nitrogen atom to which they are attached, are joined together to form a cyclic group selected from azaspiro[2.5]octanyl, azepanyl, azetidinyl, diazepanyl, dioxidothiomorpholinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinyl, pyrrolidinyl, and tetrahydroisoquinolinyl, each substituted with zero to 1 R$_{1d}$ and zero to 1 R$_{1e}$;

R$_{1c}$ is C$_{3-6}$ cycloalkyl, phenyl, oxetanyl, furanyl, pyrrolidinyl, pyrrolidinonyl, imidazolyl, indazolyl, thiazolyl, piperidinyl, pyridinyl, tetrahydrofuranyl, tetrahydropyranyl, morpholinyl, benzo[d]thiazolyl, naphthalenyl, quinolinyl, or quinoxalinyl, each substituted with zero to 2 substituents independently selected from F, Cl, —CN, —OH, —CH$_3$, —CF$_3$, —OCH$_3$, —OCF$_3$, —C(O)OCH$_3$, —NH(CH$_3$), —N(CH$_3$)$_2$, —S(O)$_2$CH$_3$, —S(O)$_2$N(CH$_3$)$_2$, —CH$_2$(phenyl), —NO$_2$, cyclopropyl, imidazolyl, and phenyl;

R$_{1d}$ is —CH$_3$, —CH(CH$_3$)$_2$, —OCH$_3$, —OCH$_2$CH$_3$, —OCH(CH$_3$)$_2$, —N(CH$_3$)$_2$, —NHC(O)CH$_3$, —C(O)CH$_3$, —C(O)NH$_2$, —C(O)N(CH$_3$)$_2$, —C(O)N(CH$_2$CH$_3$)$_2$, —CH$_2$(phenyl), —CH$_2$(methylpyrrolidinyl), —CH$_2$(benzo[d][1,3]dioxolyl), —CH(phenyl)$_2$, —C(O)(tetrahydrofuranyl), —C(O)(furanyl), —S(O)$_2$(methylphenyl), phenyl, methylphenyl, aminophenyl, piperidinyl, pyrazinyl, pyridinyl, pyrimidinyl, pyrrolidinyl, or dihydrobenzo[d]imidazolonyl; and R$_{1e}$ is —CH$_3$;

R$_4$ is —CH$_3$; and n is zero or 1.

5. The compound according to claim 1 or a pharmaceutically acceptable salt thereof, wherein Z is CR$_6$R$_6$.

6. The compound according to claim 1 or a pharmaceutically acceptable salt thereof, wherein R$_{1a}$ is hydrogen, C$_{1-6}$ alkyl, C$_{1-4}$ fluoroalkyl, C$_{1-3}$ cyanoalkyl, C$_{1-6}$ hydroxyalkyl, —(CH$_2$)$_{1-3}$O(C$_{1-3}$ alkyl), —(CH$_2$)$_{1-3}$S(O)$_2$(C$_{1-3}$ alkyl), —(CH$_2$)$_{1-3}$C(O)O(C$_{1-3}$ alkyl), —(CH$_2$)$_{1-3}$NR$_x$R$_x$, —(CH$_2$)$_{1-3}$C(O)NR$_x$R$_x$, —(CH$_2$)$_{1-3}$NR$_x$C(O)(C$_{1-3}$ alkyl), —C(O)(C$_{1-3}$ alkyl), —CH(phenyl)(C$_{1-2}$ hydroxyalkyl), —CR$_x$R$_x$CR$_x$(phenyl)$_2$, R$_{1c}$, —(CR$_x$R$_x$)$_{1-3}$R$_{1c}$, —(CR$_x$R$_x$)$_{1-3}$OR$_{1c}$, or —C(O)R$_{1c}$.

7. The compound according to claim 1 or a pharmaceutically acceptable salt thereof, wherein R$_{1a}$ is hydrogen, C$_{1-6}$ alkyl, —CH$_2$CH$_2$CF$_3$, —CH$_2$CN, —CH$_2$CH$_2$OH, —CH(CH$_3$)CH$_2$OH, —CH$_2$CH$_2$CH$_2$OH, —CH(CH$_3$)CH$_2$CH$_2$OH, —CH$_2$CH$_2$OCH$_3$, —CH$_2$CH$_2$C(O)OCH$_3$, —CH$_2$CH$_2$N(CH$_3$)$_2$, —CH$_2$C(O)NH$_2$, —CH$_2$C(O)N(CH$_3$)$_2$, —CH$_2$CH$_2$C(O)NH$_2$, —CH$_2$CH$_2$NHC(O)CH$_3$, —CH(phenyl)(CH$_2$CH$_2$OH), —CH$_2$CH(phenyl)$_2$, R$_{1c}$, —CR$_x$R$_x$R$_{1c}$, —CH$_2$CH$_2$R$_{1c}$, —CH$_2$CH$_2$CH$_2$R$_{1c}$, or —CH$_2$CH$_2$OR$_{1c}$.

8. The compound according to claim 1 or a pharmaceutically acceptable salt thereof, wherein R$_{1a}$ and R$_{1b}$ along with the nitrogen atom to which they are attached, are joined together to form a cyclic group selected from azaspiro[2.5]octanyl, azepanyl, azetidinyl, diazepanyl, dioxidothiomorpholinyl, morpholinyl, octahydrocyclopenta[b]pyrrolyl, octahydropyrrolo[3,4-c]pyrrolyl, oxaazabicyclo[2.2.1]heptanyl, piperazinonyl, piperazinyl, piperidinyl, pyrrolidinyl, and tetrahydroisoquinolinyl, each substituted with zero to 1 $R_{1d}$ and zero to 1 $R_{1e}$.

9. The compound according to claim 1 or a pharmaceutically acceptable salt thereof, wherein Ring A is:

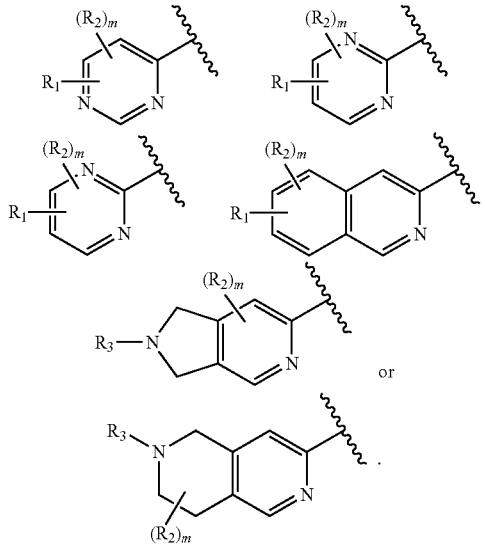

10. The compound according to claim 1 or a pharmaceutically acceptable salt thereof, wherein said compound is:
- 3-(5-{4-[(dimethylamino)methyl]pyridin-2-yl}-1-oxo-2,3-dihydro-1H-isoindol-2-yl) piperidine-2,6-dione (1);
- 3-(5-(4-((benzylamino)methyl)pyridin-2-yl)-1-oxoisoindolin-2-yl)piperidine-2,6-dione (2);
- 3-(5-(4-((methyl(propyl)amino)methyl)pyridin-2-yl)-1-oxoisoindolin-2-yl)piperidine-2,6-dione (3);
- 3-(5-(4-((ethyl(methyl)amino)methyl)pyridin-2-yl)-1-oxoisoindolin-2-yl)piperidine-2,6-dione (4);
- 3-(5-(4-((ethyl(methyl)amino)methyl)pyridin-2-yl)-1-oxoisoindolin-2-yl)piperidine-2,6-dione (5);
- 3-(5-(4-(((2-methoxyethyl)(methyl)amino)methyl)pyridin-2-yl)-1-oxoisoindolin-2-yl) piperidine-2,6-dione (7);
- 3-(5-(4-((butyl(methyl)amino)methyl)pyridin-2-yl)-1-oxoisoindolin-2-yl)piperidine-2,6-dione (9);
- 3-(5-(4-(((cyclopropylmethyl)(propyl)amino)methyl) pyridin-2-yl)-1-oxoisoindolin-2-yl)piperidine-2,6-dione (10);
- 3-(5-(4-((methyl(2-(pyridin-2-yl)ethyl)amino)methyl) pyridin-2-yl)-1-oxoisoindolin-2-yl)piperidine-2,6-dione (16);
- 3-(5-(4-((benzyl(isopropyl)amino)methyl)pyridin-2-yl)-1-oxoisoindolin-2-yl) piperidine-2,6-dione (19);
- 3-(5-(4-(((2-(dimethylamino)ethyl)(methyl)amino) methyl)pyridin-2-yl)-1-oxoisoindolin-2-yl)piperidine-2,6-dione (21);
- 3-(5-(4-((ethyl(pyridin-4-ylmethyl)amino)methyl)pyridin-2-yl)-1-oxoisoindolin-2-yl) piperidine-2,6-dione (22);
- 3-(5-(4-((methyl(1-methylpyrrolidin-3-yl)amino)methyl) pyridin-2-yl)-1-oxoisoindolin-2-yl)piperidine-2,6-dione (29);
- 2-(((2-(2-(2,6-dioxopiperidin-3-yl)-1-oxoisoindolin-5-yl) pyridin-4-yl)methyl) (methyl)amino)-N,N-dimethylacetamide (34);
- 3-(5-(4-((methyl(1-methylpyrrolidin-3-yl)amino)methyl) pyridin-2-yl)-1-oxoisoindolin-2-yl)piperidine-2,6-dione (49);
- 3-(5-(4-((diethylamino)methyl)pyridin-2-yl)-1-oxoisoindolin-2-yl)piperidine-2,6-dione (50);
- 3-(5-(4-(((cyclohexylmethyl)amino)methyl)pyridin-2-yl)-1-oxoisoindolin-2-yl) piperidine-2,6-dione (54);
- 3-(1-oxo-5-(4-(((1-phenylethyl)amino)methyl)pyridin-2-yl)isoindolin-2-yl)piperidine-2,6-dione (55);
- 3-(5-(4-(((2-methylbenzyl)amino)methyl)pyridin-2-yl)-1-oxoisoindolin-2-yl) piperidine-2,6-dione (56);
- 3-(5-(4-(((3-methylbenzyl)amino)methyl)pyridin-2-yl)-1-oxoisoindolin-2-yl) piperidine-2,6-dione (57);
- 3-(5-(4-(((4-methylbenzyl)amino)methyl)pyridin-2-yl)-1-oxoisoindolin-2-yl) piperidine-2,6-dione (58);
- 3-(5-(4-(((cyclohexylmethyl)(methyl)amino)methyl)pyridin-2-yl)-1-oxoisoindolin-2-yl)piperidine-2,6-dione (59);
- 3-(5-(4-((butylamino)methyl)pyridin-2-yl)-1-oxoisoindolin-2-yl)piperidine-2,6-dione (61);
- 3-(1-oxo-5-(4-((propylamino)methyl)pyridin-2-yl)isoindolin-2-yl)piperidine-2,6-dione (62);
- 3-(1-oxo-5-(4-((phenethylamino)methyl)pyridin-2-yl) isoindolin-2-yl)piperidine-2,6-dione (63);
- 3-(5-(4-(((cyclopropylmethyl)amino)methyl)pyridin-2-yl)-1-oxoisoindolin-2-yl) piperidine-2,6-dione (64);
- 3-(5-(4-((neopentylamino)methyl)pyridin-2-yl)-1-oxoisoindolin-2-yl)piperidine-2,6-dione (65);
- 3-(1-oxo-5-(4-((((tetrahydrofuran-2-yl)methyl)amino) methyl)pyridin-2-yl)isoindolin-2-yl)piperidine-2,6-dione (66);
- 3-(5-(4-(((4-methoxybenzyl)amino)methyl)pyridin-2-yl)-1-oxoisoindolin-2-yl) piperidine-2,6-dione (67);
- 3-(5-(4-(((2-methoxyethyl)amino)methyl)pyridin-2-yl)-1-oxoisoindolin-2-yl) piperidine-2,6-dione (68);
- 3-(5-(4-(((1-cyclopropylcyclobutyl)amino)methyl)pyridin-2-yl)-1-oxoisoindolin-2-yl) piperidine-2,6-dione (77);
- 3-(5-(4-(((2-methyltetrahydro-2H-pyran-4-yl)amino) methyl)pyridin-2-yl)-1-oxoisoindolin-2-yl)piperidine-2,6-dione (80);
- 3-(1-oxo-5-(4-(((((1R,2R)-2-phenylcyclopentyl)amino) methyl)pyridin-2-yl)isoindolin-2-yl)piperidine-2,6-dione (84);
- 3-(5-(4-((cyclopentylamino)methyl)pyridin-2-yl)-1-oxoisoindolin-2-yl)piperidine-2,6-dione (86);
- 3-(5-(4-((cyclohexylamino)methyl)pyridin-2-yl)-1-oxoisoindolin-2-yl)piperidine-2,6-dione (87);
- 3-(5-(4-(((2-morpholinoethyl)amino)methyl)pyridin-2-yl)-1-oxoisoindolin-2-yl) piperidine-2,6-dione (88);
- 3-(5-(4-((tert-butylamino)methyl)pyridin-2-yl)-1-oxoisoindolin-2-yl)piperidine-2,6-dione (89);
- 3-(5-(4-(((2,2-diphenylethyl)amino)methyl)pyridin-2-yl)-1-oxoisoindolin-2-yl)piperidine-2,6-dione (90);
- N-(2-(((2-(2-(2,6-dioxopiperidin-3-yl)-1-oxoisoindolin-5-yl)pyridin-4-yl)methyl) amino)ethyl)acetamide (91);
- 3-(5-(4-(((2-hydroxyethyl)amino)methyl)pyridin-2-yl)-1-oxoisoindolin-2-yl) piperidine-2,6-dione (92);
- 3-(5-(4-(((2-chlorophenethyl)amino)methyl)pyridin-2-yl)-1-oxoisoindolin-2-yl) piperidine-2,6-dione (93);
- 3-(5-(4-(((4-chlorophenethyl)amino)methyl)pyridin-2-yl)-1-oxoisoindolin-2-yl) piperidine-2,6-dione (94);
- 3-(5-(4-(((4-methoxyphenethyl)amino)methyl)pyridin-2-yl)-1-oxoisoindolin-2-yl) piperidine-2,6-dione (95);
- 3-(5-(4-(((4-hydroxyphenethyl)amino)methyl)pyridin-2-yl)-1-oxoisoindolin-2-yl) piperidine-2,6-dione (96);

3-(5-(4-((isopentylamino)methyl)pyridin-2-yl)-1-oxoisoindolin-2-yl)piperidine-2,6-dione (97);
3-(1-oxo-5-(4-(((3-phenylpropyl)amino)methyl)pyridin-2-yl)isoindolin-2-yl) piperidine-2,6-dione (98);
2-(((2-(2-(2,6-dioxopiperidin-3-yl)-1-oxoisoindolin-5-yl) pyridin-4-yl)methyl)amino) acetonitrile (99);
2-(((2-(2-(2,6-dioxopiperidin-3-yl)-1-oxoisoindolin-5-yl) pyridin-4-yl)methyl)amino) acetamide (100);
3-(5-(4-(((4-hydroxycyclohexyl)amino)methyl)pyridin-2-yl)-1-oxoisoindolin-2-yl) piperidine-2,6-dione (101);
3-(5-(4-(((3-chlorophenethyl)amino)methyl)pyridin-2-yl)-1-oxoisoindolin-2-yl) piperidine-2,6-dione (102);
3-(1-oxo-5-(4-(((2-phenoxyethyl)amino)methyl)pyridin-2-yl)isoindolin-2-yl) piperidine-2,6-dione (103);
3-(5-(4-(((1-benzylpyrrolidin-3-yl)amino)methyl)pyridin-2-yl)-1-oxoisoindolin-2-yl) piperidine-2,6-dione (104);
3-(((2-(2-(2,6-dioxopiperidin-3-yl)-1-oxoisoindolin-5-yl) pyridin-4-yl)methyl)amino) propanamide (105);
3-(5-(4-(((2-(benzo[d]thiazol-2-yl)ethyl)amino)methyl) pyridin-2-yl)-1-oxoisoindolin-2-yl)piperidine-2,6-dione (106);
3-(5-(4-(((4-(dimethylamino)cyclohexyl)amino)methyl) pyridin-2-yl)-1-oxoisoindolin-2-yl)piperidine-2,6-dione (107);
3-(5-(4-((cyclobutylamino)methyl)pyridin-2-yl)-1-oxoisoindolin-2-yl)piperidine-2,6-dione (108);
3-(5-(4-((cyclopropylamino)methyl)pyridin-2-yl)-1-oxoisoindolin-2-yl)piperidine-2,6-dione (109);
3-(1-oxo-5-(4-((((2-phenylthiazol-4-yl)methyl)amino) methyl)pyridin-2-yl)isoindolin-2-yl)piperidine-2,6-dione (110);
3-(1-oxo-5-(4-(((((1R,2S)-2-phenylcyclopropyl)amino) methyl)pyridin-2-yl)isoindolin-2-yl)piperidine-2,6-dione (111);
methyl 3-(((2-(2-(2,6-dioxopiperidin-3-yl)-1-oxoisoindolin-5-yl)pyridin-4-yl)methyl) amino)propanoate (112);
3-(5-(4-(((3-(1H-imidazol-1-yl)propyl)amino)methyl) pyridin-2-yl)-1-oxoisoindolin-2-yl)piperidine-2,6-dione (113);
3-(5-(4-(((3-morpholinopropyl)amino)methyl)pyridin-2-yl)-1-oxoisoindolin-2-yl) piperidine-2,6-dione (114);
3-(1-oxo-5-(4-(((3-(2-oxopyrrolidin-1-yl)propyl)amino) methyl)pyridin-2-yl) isoindolin-2-yl)piperidine-2,6-dione (115);
3-(5-(4-((ethylamino)methyl)pyridin-2-yl)-1-oxoisoindolin-2-yl)piperidine-2,6-dione (116);
3-(1-oxo-5-(4-((((R)-1-phenylethyl)amino)methyl)pyridin-2-yl)isoindolin-2-yl) piperidine-2,6-dione (122);
3-(1-oxo-5-(4-((((S)-1-phenylethyl)amino)methyl)pyridin-2-yl)isoindolin-2-yl) piperidine-2,6-dione (123);
3-(5-(4-((((1-hydroxycyclohexyl)methyl)amino)methyl) pyridin-2-yl)-1-oxoisoindolin-2-yl)piperidine-2,6-dione (124);
3-(5-(4-(((2-methyltetrahydro-2H-pyran-4-yl)amino) methyl)pyridin-2-yl)-1-oxoisoindolin-2-yl)piperidine-2,6-dione (126);
3-(5-(4-(((4-hydroxybutyl)amino)methyl)pyridin-2-yl)-1-oxoisoindolin-2-yl) piperidine-2,6-dione (128);
3-(5-(4-(((oxetan-2-ylmethyl)amino)methyl)pyridin-2-yl)-1-oxoisoindolin-2-yl) piperidine-2,6-dione (129);
3-(5-(4-(((((R)-3-hydroxy-1-phenylpropyl)amino)methyl) pyridin-2-yl)-1-oxoisoindolin-2-yl)piperidine-2,6-dione (131);
3-(5-(4-((methyl((S)-1-phenylethyl)amino)methyl)pyridin-2-yl)-1-oxoisoindolin-2-yl) piperidine-2,6-dione (136);
3-(5-(4-((methyl((R)-1-phenylethyl)amino)methyl)pyridin-2-yl)-1-oxoisoindolin-2-yl)piperidine-2,6-dione (137);
3-(5-(4-((methyl((1R,2R)-2-(methylamino)cyclohexyl) amino)methyl)pyridin-2-yl)-1-oxoisoindolin-2-yl)piperidine-2,6-dione (140);
3-(5-(4-((methyl(2-phenylpropan-2-yl)amino)methyl) pyridin-2-yl)-1-oxoisoindolin-2-yl)piperidine-2,6-dione (142);
3-(1-oxo-5-(4-((3-phenylpiperidin-1-yl)methyl)pyridin-2-yl)isoindolin-2-yl) piperidine-2,6-dione (144);
3-(5-{4-[(methylamino)methyl]pyridin-2-yl}-1-oxo-2,3-dihydro-1H-isoindol-2-yl) piperidine-2,6-dione (145);
4-{[({2-[2-(2,6-dioxopiperidin-3-yl)-1-oxo-2,3-dihydro-1H-isoindol-5-yl]pyridin-4-yl}methyl)(methyl)amino] methyl}-N,N-dimethylbenzene-1-sulfonamide (146);
3-(5-(4-(((4-fluorobenzyl)(methyl)amino)methyl)pyridin-2-yl)-1-oxoisoindolin-2-yl) piperidine-2,6-dione (147);
3-(5-(4-((methyl(3-(trifluoromethyl)benzyl)amino) methyl)pyridin-2-yl)-1-oxoisoindolin-2-yl)piperidine-2,6-dione (148);
3-(5-(4-((methyl(4-(trifluoromethyl)benzyl)amino) methyl)pyridin-2-yl)-1-oxoisoindolin-2-yl)piperidine-2,6-dione (149);
4-((((2-(2-(2,6-dioxopiperidin-3-yl)-1-oxoisoindolin-5-yl)pyridin-4-yl)methyl) (methyl)amino)methyl)benzonitrile (150);
3-(5-(4-((methyl(4-nitrobenzyl)amino)methyl)pyridin-2-yl)-1-oxoisoindolin-2-yl) piperidine-2,6-dione (151);
3-(5-(4-(((3,4-difluorobenzyl)(methyl)amino)methyl) pyridin-2-yl)-1-oxoisoindolin-2-yl)piperidine-2,6-dione (152);
methyl 4-((((2-(2-(2,6-dioxopiperidin-3-yl)-1-oxoisoindolin-5-yl)pyridin-4-yl)methyl) (methyl)amino) methyl)benzoate (153);
3-(5-(4-(((4-chlorobenzyl)(methyl)amino)methyl)pyridin-2-yl)-1-oxoisoindolin-2-yl) piperidine-2,6-dione (154);
3-(5-(4-((methyl(quinolin-8-ylmethyl)amino)methyl) pyridin-2-yl)-1-oxoisoindolin-2-yl)piperidine-2,6-dione (155);
3-(5-(4-((methyl(3-(trifluoromethoxy)benzyl)amino) methyl)pyridin-2-yl)-1-oxoisoindolin-2-yl)piperidine-2,6-dione (156);
3-(5-(4-((methyl(4-(methylsulfonyl)benzyl)amino) methyl)pyridin-2-yl)-1-oxoisoindolin-2-yl)piperidine-2,6-dione (157);
3-(5-(4-(((3-methoxybenzyl)(methyl)amino)methyl)pyridin-2-yl)-1-oxoisoindolin-2-yl) piperidine-2,6-dione (158);
3-(5-(4-((methyl(pyridin-3-ylmethyl)amino)methyl)pyridin-2-yl)-1-oxoisoindolin-2-yl) piperidine-2,6-dione (159);
3-(5-(4-((methyl(pyridin-4-ylmethyl)amino)methyl)pyridin-2-yl)-1-oxoisoindolin-2-yl) piperidine-2,6-dione (160);
3-(5-(4-((methyl(4-methylbenzyl)amino)methyl)pyridin-2-yl)-1-oxoisoindolin-2-yl) piperidine-2,6-dione (161);
3-(5-(4-((methyl(naphthalen-2-ylmethyl)amino)methyl) pyridin-2-yl)-1-oxoisoindolin-2-yl)piperidine-2,6-dione (162);
3-(5-{4-[(dibenzylamino)methyl]pyridin-2-yl}-1-oxo-2,3-dihydro-1H-isoindol-2-yl) piperidine-2,6-dione (163);

3-[5-(4-{[benzyl(methyl)amino]methyl}pyridin-2-yl)-1-oxo-2,3-dihydro-1H-isoindol-2-yl]piperidine-2,6-dione (164);

3-{5-[4-({[(6-methoxypyridin-3-yl)methyl](methyl) amino}methyl)pyridin-2-yl]-1-oxo-2,3-dihydro-1H-isoindol-2-yl}piperidine-2,6-dione (168);

3-(5-(4-(((((1H-indazol-4-yl)methyl)(methyl)amino) methyl)pyridin-2-yl)-1-oxoisoindolin-2-yl)piperidine-2,6-dione (169);

3-(5-(4-((methyl(1-methylpiperidin-4-yl)amino)methyl) pyridin-2-yl)-1-oxoisoindolin-2-yl)piperidine-2,6-dione (170);

3-(5-(4-((methyl(phenethyl)amino)methyl)pyridin-2-yl)-1-oxoisoindolin-2-yl) piperidine-2,6-dione (171);

3-(5-(4-(((furan-3-ylmethyl)(methyl)amino)methyl)pyridin-2-yl)-1-oxoisoindolin-2-yl)piperidine-2,6-dione (172);

3-(5-(4-(((cyclopropylmethyl)(methyl)amino)methyl) pyridin-2-yl)-1-oxoisoindolin-2-yl)piperidine-2,6-dione (173);

3-(5-(4-((methyl((1-methyl-1H-imidazol-5-yl)methyl) amino)methyl)pyridin-2-yl)-1-oxoisoindolin-2-yl)piperidine-2,6-dione (174);

3-(5-(4-(((cyclopentylmethyl)(methyl)amino)methyl) pyridin-2-yl)-1-oxoisoindolin-2-yl)piperidine-2,6-dione (175);

3-(5-(4-((methyl(thiazol-2-ylmethyl)amino)methyl)pyridin-2-yl)-1-oxoisoindolin-2-yl)piperidine-2,6-dione (176);

3-(5-(4-(((4-(1H-imidazol-1-yl)benzyl)(methyl)amino) methyl)pyridin-2-yl)-1-oxoisoindolin-2-yl)piperidine-2,6-dione (177);

3-(5-(4-(((cyclobutylmethyl)(methyl)amino)methyl)pyridin-2-yl)-1-oxoisoindolin-2-yl)piperidine-2,6-dione (178);

3-(5-(4-((isobutyl(methyl)amino)methyl)pyridin-2-yl)-1-oxoisoindolin-2-yl) piperidine-2,6-dione (179);

3-(5-(4-((isopentyl(methyl)amino)methyl)pyridin-2-yl)-1-oxoisoindolin-2-yl) piperidine-2,6-dione (180);

3-(5-(4-(((1-hydroxypropan-2-yl)(methyl)amino)methyl) pyridin-2-yl)-1-oxoisoindolin-2-yl)piperidine-2,6-dione (181);

3-(5-(4-((methyl((tetrahydrofuran-3-yl)methyl)amino) methyl)pyridin-2-yl)-1-oxoisoindolin-2-yl)piperidine-2,6-dione (182);

3-(5-(4-((methyl(quinoxalin-2-ylmethyl)amino)methyl) pyridin-2-yl)-1-oxoisoindolin-2-yl)piperidine-2,6-dione (183);

3-(5-(4-((methyl(3,3,3-trifluoropropyl)amino)methyl) pyridin-2-yl)-1-oxoisoindolin-2-yl)piperidine-2,6-dione (184);

3-(5-(4-(((4-hydroxybutan-2-yl)(methyl)amino)methyl) pyridin-2-yl)-1-oxoisoindolin-2-yl)piperidine-2,6-dione (185); or 3-(5-(4-((dimethylamino)methyl)pyridin-2-yl)-6-methyl-1-oxoisoindolin-2-yl) piperidine-2,6-dione (194).

11. The compound according to claim 1 or a pharmaceutically acceptable salt thereof, wherein said compound is selected from a compound of 3-(5-(4-((ethyl(methyl)amino)methyl)pyridin-2-yl)-1-oxoisoindolin-2-yl)piperidine-2,6-dione (6);

3-(1-oxo-5-(4-(pyrrolidin-1-ylmethyl)pyridin-2-yl)isoindolin-2-yl)piperidine-2,6-dione (8);

3-(1-oxo-5-(4-((4-(2-oxo-2,3-dihydro-1H-benzo[d]imidazol-1-yl)piperidin-1-yl) methyl)pyridin-2-yl)isoindolin-2-yl)piperidine-2,6-dione (11);

3-(5-(4-((4-(benzo[d][1,3]dioxol-5-ylmethyl)piperazin-1-yl)methyl)pyridin-2-yl)-1-oxoisoindolin-2-yl)piperidine-2,6-dione (12);

1-((2-(2-(2,6-dioxopiperidin-3-yl)-1-oxoisoindolin-5-yl) pyridin-4-yl)methyl)-N,N-diethylpiperidine-3-carboxamide (13);

3-(5-(4-((4-methylpiperidin-1-yl)methyl)pyridin-2-yl)-1-oxoisoindolin-2-yl) piperidine-2,6-dione (14);

3-(1-oxo-5-(4-((4-(pyridin-2-yl)piperidin-1-yl)methyl) pyridin-2-yl)isoindolin-2-yl) piperidine-2,6-dione (15);

3-(5-(4-([1,4'-bipiperidin]-1'-ylmethyl)pyridin-2-yl)-1-oxoisoindolin-2-yl)piperidine-2,6-dione (17);

3-(1-oxo-5-(4-((4-(pyrimidin-2-yl)piperidin-1-yl)methyl) pyridin-2-yl)isoindolin-2-yl) piperidine-2,6-dione (18);

3-(5-(4-((2-methylpyrrolidin-1-yl)methyl)pyridin-2-yl)-1-oxoisoindolin-2-yl) piperidine-2,6-dione (20);

3-(1-oxo-5-(4-((4-(pyrrolidin-1-yl)piperidin-1-yl)methyl) pyridin-2-yl)isoindolin-2-yl) piperidine-2,6-dione (23);

3-(5-(4-((4-(furan-2-carbonyl)piperazin-1-yl)methyl) pyridin-2-yl)-1-oxoisoindolin-2-yl)piperidine-2,6-dione (24);

3-(1-oxo-5-(4-((4-(pyridin-4-yl)piperazin-1-yl)methyl) pyridin-2-yl)isoindolin-2-yl) piperidine-2,6-dione (25);

3-(1-oxo-5-(4-((4-(pyrazin-2-yl)piperazin-1-yl)methyl) pyridin-2-yl)isoindolin-2-yl) piperidine-2,6-dione (26);

3-(5-(4-((3-methyl-4-(m-tolyl)piperazin-1-yl)methyl) pyridin-2-yl)-1-oxoisoindolin-2-yl)piperidine-2,6-dione (27);

3-(5-(4-((4-acetylpiperazin-1-yl)methyl)pyridin-2-yl)-1-oxoisoindolin-2-yl) piperidine-2,6-dione (28);

3-(5-(4-((2-(((S)-1-methylpyrrolidin-2-yl)methyl)piperidin-1-yl)methyl)pyridin-2-yl)-1-oxoisoindolin-2-yl)piperidine-2,6-dione (30);

N-((3S)-1-((2-(2-(2,6-dioxopiperidin-3-yl)-1-oxoisoindolin-5-yl)pyridin-4-yl)methyl) pyrrolidin-3-yl)acetamide (31);

3-(1-oxo-5-(4-((4-(tetrahydrofuran-2-carbonyl)piperazin-1-yl)methyl)pyridin-2-yl) isoindolin-2-yl)piperidine-2, 6-dione (32);

3-(5-(4-(((S)-3-(dimethylamino)pyrrolidin-1-yl)methyl) pyridin-2-yl)-1-oxoisoindolin-2-yl)piperidine-2,6-dione (33);

3-(5-(4-((4-methylpiperazin-1-yl)methyl)pyridin-2-yl)-1-oxoisoindolin-2-yl) piperidine-2,6-dione (35);

3-(5-(4-(((4-benzylpiperazin-1-yl)methyl)pyridin-2-yl)-1-oxoisoindolin-2-yl) piperidine-2,6-dione (36);

3-(1-oxo-5-(4-((3-oxopiperazin-1-yl)methyl)pyridin-2-yl)isoindolin-2-yl)piperidine-2,6-dione (37);

3-(5-(4-((4-benzylpiperidin-1-yl)methyl)pyridin-2-yl)-1-oxoisoindolin-2-yl) piperidine-2,6-dione (38);

3-(5-(4-((3,4-dihydroisoquinolin-2(1H)-yl)methyl)pyridin-2-yl)-1-oxoisoindolin-2-yl) piperidine-2,6-dione (39);

3-(5-(4-((4-(dimethylamino)piperidin-1-yl)methyl)pyridin-2-yl)-1-oxoisoindolin-2-yl) piperidine-2,6-dione (40);

1-((2-(2-(2,6-dioxopiperidin-3-yl)-1-oxoisoindolin-5-yl) pyridin-4-yl)methyl) piperidine-4-carboxamide (41);

3-(5-(4-((4-benzhydrylpiperidin-1-yl)methyl)pyridin-2-yl)-1-oxoisoindolin-2-yl) piperidine-2,6-dione (42);

3-(5-(4-((4-methyl-1,4-diazepan-1-yl)methyl)pyridin-2-yl)-1-oxoisoindolin-2-yl) piperidine-2,6-dione (43);

3-(5-(4-((4-isopropylpiperazin-1-yl)methyl)pyridin-2-yl)-1-oxoisoindolin-2-yl) piperidine-2,6-dione (44);

3-(5-(4-(((R)-3-(dimethylamino)pyrrolidin-1-yl)methyl) pyridin-2-yl)-1-oxoisoindolin-2-yl)piperidine-2,6-dione (45);

3-(5-(4-((2-methylazetidin-1-yl)methyl)pyridin-2-yl)-1-oxoisoindolin-2-yl)piperidine-2,6-dione (46);
3-(5-(4-((3-methylazetidin-1-yl)methyl)pyridin-2-yl)-1-oxoisoindolin-2-yl)piperidine-2,6-dione (47);
3-(5-(4-(azepan-1-ylmethyl)pyridin-2-yl)-1-oxoisoindolin-2-yl)piperidine-2,6-dione (48);
3-(5-(4-((3,3-dimethylazetidin-1-yl)methyl)pyridin-2-yl)-1-oxoisoindolin-2-yl) piperidine-2,6-dione (51);
3-(5-(4-((2,2-dimethylazetidin-1-yl)methyl)pyridin-2-yl)-1-oxoisoindolin-2-yl) piperidine-2,6-dione (52);
3-(5-(4-((2,6-dimethylpiperidin-1-yl)methyl)pyridin-2-yl)-1-oxoisoindolin-2-yl) piperidine-2,6-dione (53);
3-(5-(4-((hexahydrocyclopenta[b]pyrrol-1(2H)-yl)methyl)pyridin-2-yl)-1-oxoisoindolin-2-yl)piperidine-2,6-dione (60);
3-(5-(4-(((S)-2-methylpyrrolidin-1-yl)methyl)pyridin-2-yl)-1-oxoisoindolin-2-yl)piperidine-2,6-dione (69);
3-(5-(4-(((R)-3-methylpyrrolidin-1-yl)methyl)pyridin-2-yl)-1-oxoisoindolin-2-yl)piperidine-2,6-dione (70);
3-(5-(4-(((R)-2-methylpiperidin-1-yl)methyl)pyridin-2-yl)-1-oxoisoindolin-2-yl)piperidine-2,6-dione (71);
3-(5-(4-(((S)-3-methylpyrrolidin-1-yl)methyl)pyridin-2-yl)-1-oxoisoindolin-2-yl) piperidine-2,6-dione (72);
3-(5-(4-(((S)-3-methylpiperidin-1-yl)methyl)pyridin-2-yl)-1-oxoisoindolin-2-yl) piperidine-2,6-dione (73);
3-(5-(4-(((S)-2-methylpiperidin-1-yl)methyl)pyridin-2-yl)-1-oxoisoindolin-2-yl) piperidine-2,6-dione (74);
3-(5-(4-(((R)-3-methylpiperidin-1-yl)methyl)pyridin-2-yl)-1-oxoisoindolin-2-yl) piperidine-2,6-dione (75);
3-(1-oxo-5-(4-((2-phenylazetidin-1-yl)methyl)pyridin-2-yl)isoindolin-2-yl)piperidine-2,6-dione (76);
3-(5-(4-(((3aR,6aS)-5-methylhexahydropyrrolo[3,4-c]pyrrol-2(1H)-yl)methyl)pyridin-2-yl)-1-oxoisoindolin-2-yl)piperidine-2,6-dione (78);
3-(5-(4-((2-oxa-5-azabicyclo[2.2.1]heptan-5-yl)methyl)pyridin-2-yl)-1-oxoisoindolin-2-yl)piperidine-2,6-dione (79);
3-(5-(4-(((3S,5R)-3,5-dimethylpiperidin-1-yl)methyl)pyridin-2-yl)-1-oxoisoindolin-2-yl)piperidine-2,6-dione (81);
3-(5-(4-((4,4-dimethylpiperidin-1-yl)methyl)pyridin-2-yl)-1-oxoisoindolin-2-yl) piperidine-2,6-dione (82);
3-(1-oxo-5-(4-((3-phenylazetidin-1-yl)methyl)pyridin-2-yl)isoindolin-2-yl)piperidine-2,6-dione (83);
3-(5-(4-((3,3-dimethylpiperidin-1-yl)methyl)pyridin-2-yl)-1-oxoisoindolin-2-yl) piperidine-2,6-dione (85);
3-(5-(4-((2,2-dimethylpyrrolidin-1-yl)methyl)pyridin-2-yl)-1-oxoisoindolin-2-yl) piperidine-2,6-dione (117);
3-(5-(4-((3,3-dimethylpyrrolidin-1-yl)methyl)pyridin-2-yl)-1-oxoisoindolin-2-yl) piperidine-2,6-dione (118);
3-(5-(4-((2,5-dimethylpyrrolidin-1-yl)methyl)pyridin-2-yl)-1-oxoisoindolin-2-yl) piperidine-2,6-dione (119);
3-(5-(4-(((2R,6S)-2,6-dimethylpiperidin-1-yl)methyl)pyridin-2-yl)-1-oxoisoindolin-2-yl)piperidine-2,6-dione (120);
3-(5-(4-((4-(4-aminophenyl)-4-methylpiperidin-1-yl)methyl)pyridin-2-yl)-1-oxoisoindolin-2-yl)piperidine-2,6-dione (121);
3-(5-(4-(((R)-2-methylpyrrolidin-1-yl)methyl)pyridin-2-yl)-1-oxoisoindolin-2-yl) piperidine-2,6-dione (125);
3-(5-(4-((6-azaspiro[2.5]octan-6-yl)methyl)pyridin-2-yl)-1-oxoisoindolin-2-yl) piperidine-2,6-dione (127);
3-(5-(4-((3-isopropoxyazetidin-1-yl)methyl)pyridin-2-yl)-1-oxoisoindolin-2-yl) piperidine-2,6-dione (130);
3-(1-oxo-5-(4-((4-tosylpiperidin-1-yl)methyl)pyridin-2-yl)isoindolin-2-yl)piperidine-2,6-dione (132);
3-(1-oxo-5-(4-(((S)-2-phenylpyrrolidin-1-yl)methyl)pyridin-2-yl)isoindolin-2-yl) piperidine-2,6-dione (133);
3-(1-oxo-5-(4-(((R)-2-phenylpyrrolidin-1-yl)methyl)pyridin-2-yl)isoindolin-2-yl) piperidine-2,6-dione (134);
3-(1-oxo-5-(4-(((S)-3-phenylpiperidin-1-yl)methyl)pyridin-2-yl)isoindolin-2-yl) piperidine-2,6-dione (135);
3-(1-oxo-5-(4-(((R)-3-phenylpyrrolidin-1-yl)methyl)pyridin-2-yl)isoindolin-2-yl) piperidine-2,6-dione (138);
3-(1-oxo-5-(4-(((S)-3-phenylpyrrolidin-1-yl)methyl)pyridin-2-yl)isoindolin-2-yl) piperidine-2,6-dione (139);
3-(1-oxo-5-(4-((4-phenylpiperidin-1-yl)methyl)pyridin-2-yl)isoindolin-2-yl) piperidine-2,6-dione (141);
3-(1-oxo-5-(4-((3-phenylpiperidin-1-yl)methyl)pyridin-2-yl)isoindolin-2-yl) piperidine-2,6-dione (143);
3-(5-{4-[(azetidin-1-yl)methyl]pyridin-2-yl}-1-oxo-2,3-dihydro-1H-isoindol-2-yl) piperidine-2,6-dione (165);
3-(5-{4-[(morpholin-4-yl)methyl]pyridin-2-yl}-1-oxo-2,3-dihydro-1H-isoindol-2-yl) piperidine-2,6-dione (166);
4-({2-[2-(2,6-dioxopiperidin-3-yl)-1-oxo-2,3-dihydro-1H-isoindol-5-yl]pyridin-4-yl}methyl)-1λ6-thiomorpholine-1,1-dione (167);
3-(5-(5-chloro-4-((3-phenylazetidin-1-yl)methyl)pyridin-2-yl)-1-oxoisoindolin-2-yl) piperidine-2,6-dione (186);
3-(5-(5-chloro-4-((2-phenylazetidin-1-yl)methyl)pyridin-2-yl)-1-oxoisoindolin-2-yl) piperidine-2,6-dione (187);
3-(5-(5-fluoro-4-((3-phenylazetidin-1-yl)methyl)pyridin-2-yl)-1-oxoisoindolin-2-yl) piperidine-2,6-dione (188);
3-(5-(5-fluoro-4-((2-phenylazetidin-1-yl)methyl)pyridin-2-yl)-1-oxoisoindolin-2-yl) piperidine-2,6-dione (189);
3-(5-(5-fluoro-4-((3-(pyridin-3-yl)azetidin-1-yl)methyl)pyridin-2-yl)-1-oxoisoindolin-2-yl) piperidine-2,6-dione (190);
3-(5-(3-fluoro-4-((3-phenylazetidin-1-yl)methyl)pyridin-2-yl)-1-oxoisoindolin-2-yl) piperidine-2,6-dione (191);
3-(5-(3-fluoro-4-((3-(pyridin-3-yl)azetidin-1-yl)methyl)pyridin-2-yl)-1-oxoisoindolin-2-yl)piperidine-2,6-dione (192);
3-(5-(3-fluoro-4-((2-phenylazetidin-1-yl)methyl)pyridin-2-yl)-1-oxoisoindolin-2-yl) piperidine-2,6-dione (193);
3-(1-oxo-5-(4-((3-(pyridin-4-yl)azetidin-1-yl)methyl)pyridin-2-yl)isoindolin-2-yl) piperidine-2,6-dione (195);
3-(5-(4-((3-methoxy-3-methylazetidin-1-yl)methyl)pyridin-2-yl)-1-oxoisoindolin-2-yl)piperidine-2,6-dione (196);
3-(5-(4-((3-methoxyazetidin-1-yl)methyl)pyridin-2-yl)-1-oxoisoindolin-2-yl) piperidine-2,6-dione (197);
3-(5-(4-((3-ethoxyazetidin-1-yl)methyl)pyridin-2-yl)-1-oxoisoindolin-2-yl)piperidine-2,6-dione (198);
3-(1-oxo-5-(4-((4-(p-tolyl)piperidin-1-yl)methyl)pyridin-2-yl)isoindolin-2-yl) piperidine-2,6-dione (199);
3-(5-(4-(((S)-2-benzylaziridin-1-yl)methyl)pyridin-2-yl)-1-oxoisoindolin-2-yl)piperidine-2,6-dione (200);
3-(5-(4-((2-methylaziridin-1-yl)methyl)pyridin-2-yl)-1-oxoisoindolin-2-yl)piperidine-2,6-dione (201);
1-((2-(2-(2,6-dioxopiperidin-3-yl)-1-oxoisoindolin-5-yl)pyridin-4-yl)methyl)-N,N-dimethylazetidine-3-carboxamide (202);
3-(1-oxo-5-(4-((3-(pyridin-3-yl)azetidin-1-yl)methyl)pyridin-2-yl)isoindolin-2-yl) piperidine-2,6-dione (203);
3-(1-oxo-5-(4-((2-phenylazetidin-1-yl)methyl)pyridin-2-yl)isoindolin-2-yl)piperidine-2,6-dione (204-205);

1-((2-(2-(2,6-dioxopiperidin-3-yl)-1-oxoisoindolin-5-yl) pyridin-4-yl)methyl) azetidine-2-carboxamide (206);

3-(5-(4-((4-methoxy-3,3-dimethylpiperidin-1-yl)methyl) pyridin-2-yl)-1-oxoisoindolin-2-yl)piperidine-2,6-dione (207); or 3-(4-fluoro-1-oxo-5-(4-((3-phenylazetidin-1-yl)methyl) pyridin-2-yl)isoindolin-2-yl) piperidine-2,6-dione (208).

12. A pharmaceutical composition comprising a compound according to claim 1 or a pharmaceutically-acceptable salt thereof; and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 11,548,870 B2 | Page 1 of 1 |
| APPLICATION NO. | : 16/950978 | |
| DATED | : January 10, 2023 | |
| INVENTOR(S) | : Andrew Degnan et al. | |

It is certified that error appears in the above-identified patent and that said Letters Patent is hereby corrected as shown below:

In the Claims

Claim 11, Column 144, Line 45, delete "-(((4-" and insert -- -((4- --.

Signed and Sealed this
Twenty-third Day of September, 2025

John A. Squires
*Director of the United States Patent and Trademark Office*